(12) United States Patent
Nakazato et al.

(10) Patent No.: US 7,157,594 B2
(45) Date of Patent: Jan. 2, 2007

(54) 6-FLUOROBICYCLO[3.1.0]HEXANE DERIVATIVES

(75) Inventors: Atsuro Nakazato, Tokyo (JP); Shigeyuki Chaki, Tokyo (JP); Kazunari Sakagami, Tokyo (JP); Ryoko Dean, Tokyo (JP); Hiroshi Ohta, Tokyo (JP); Shiho Hirota, Tokyo (JP); Akito Yasuhara, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 16 days.

(21) Appl. No.: 10/500,101

(22) PCT Filed: Dec. 26, 2002

(86) PCT No.: PCT/JP02/13693

§ 371 (c)(1),
(2), (4) Date: Feb. 4, 2005

(87) PCT Pub. No.: WO03/061698

PCT Pub. Date: Jul. 31, 2003

(65) Prior Publication Data

US 2005/0119345 A1 Jun. 2, 2005

(30) Foreign Application Priority Data

Dec. 27, 2001 (JP) ............................. 2001-395797

(51) Int. Cl.
C07C 69/74 (2006.01)
C07C 61/113 (2006.01)
(52) U.S. Cl. ...................................... 560/119; 562/501
(58) Field of Classification Search ................. 560/119
See application file for complete search history.

(56) References Cited

U.S. PATENT DOCUMENTS

| | | | |
|---|---|---|---|
| 5,916,920 A | 6/1999 | Fernandez et al. | |
| 5,958,960 A | 9/1999 | Massey et al. | |
| 6,107,342 A | 8/2000 | Adam et al. | |
| 6,333,428 B1 | 12/2001 | Nakazato et al. | |
| 2002/0193367 A1 | 12/2002 | Geo et al. | |

FOREIGN PATENT DOCUMENTS

| | | |
|---|---|---|
| AU | 9677310 A1 | 6/1997 |
| AU | 703093 B2 | 3/1999 |
| AU | 9947327 A1 | 3/2000 |
| AU | 9948007 A1 | 3/2000 |
| AU | 2001067854 A5 | 1/2002 |
| AU | 746806 B2 | 5/2002 |
| BR | 9611521 A | 6/1999 |
| CA | 2237598 A | 5/1997 |
| CA | 2341865 A | 3/2000 |
| CN | 1202103 A | 12/1998 |
| DE | 19941675 A1 | 3/2000 |
| EP | 774455 A1 | 5/1997 |
| EP | 1110943 A1 | 6/2001 |
| EP | 1295865 A1 | 3/2003 |
| FR | 2786768 A1 | 6/2000 |
| GB | 2341179 A1 | 3/2000 |
| JP | 2000-500752 A | 1/2000 |
| JP | 2000-086597 A2 | 3/2000 |
| JP | 2000-336071 A | 12/2000 |
| JP | 3340409 B2 | 11/2002 |
| NL | 1012963 A1 | 3/2000 |
| SE | 9903088 A | 3/2000 |
| TW | 427973 B | 4/2001 |
| WO | WO 97/17950 A | 5/1997 |
| WO | WO 00/12464 A1 | 3/2000 |
| WO | WO 01/02342 A | 1/2001 |
| WO | WO 01/85669 A1 | 11/2001 |
| WO | WO 02/00605 A1 | 1/2002 |
| ZA | 9609485 A | 5/1998 |

OTHER PUBLICATIONS

Shigetada Nakanishi, et al. "Molecular Diversity of Glutamate Receptors and Implications for Brain Function", *Science*, Oct. 23, 1992, vol. 258, pp. 597-603.

(Continued)

*Primary Examiner*—Paul A. Zucker
(74) *Attorney, Agent, or Firm*—Sughrue Mion, PLLC

(57) ABSTRACT

An antidepressant comprising, as an active ingredient, a compound having an antagonistic effect on group II metabotropic glutamate receptors, as well as a 2-amino-3-alkoxy-6-fluoro-bicyclo[3.1.0]hexane-2,6-dicarboxylic acid derivative of Formula [I]:

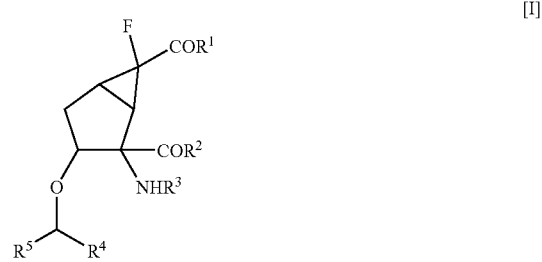

[wherein $R^1$ and $R^2$, which may be the same or different, each represent a hydroxyl group, a $C_{1-10}$ alkoxy group, etc.; $R^3$ represents a $C_{1-10}$ acyl group, a $C_{1-6}$ alkoxy-$C_{1-6}$ acyl group, etc.; and $R^4$ and $R^5$, which may be the same or different, each represent a hydrogen atom, a $C_{1-10}$ alkyl group, etc.] or a pharmaceutically acceptable salt or hydrate thereof.

28 Claims, 2 Drawing Sheets

OTHER PUBLICATIONS

Yasuto Tanabe, et al. "Signal Transduction, Pharmacological Properties, and Expression Patterns of Two Rat Metabotropic Glutamate Receptors, mGluR3 and mGluR4", *The Journal of Neuroscience*, Apr. 1993, 13(4): 1372-1378.

J.P. Pin, et al. "Review: Neurotransmitter receptors 1 The Metabotropic Glutamate Receptors: Structure and Functions", *Neuropharmacology*, 1995, vol. 34, No. 1, pp. 1-26.

Darryle D. Schoepp, et al. "Metabotropic glutamate receptors in brain function and pathology", *Trends Pharmacol.* Jan. 1993, vol. 14, pp. 13-20.

Otani, S., et al., Dopamine receptors and groups I and II mGluRs cooperate for long-term depression induction in rat prefrontal cortex through converging postsynaptic activation of MAP kinases., Journal of Neuroscience, 1999, vol. 19, No. 22, pp. 9788-9802.

6-FLUOROBICYCLO[3.1.0]HEXANE DERIVATIVES

TECHNICAL FIELD

The present invention relates to pharmaceutically useful 2-amino-3-alkoxy-6-fluorobicyclo[3.1.0]hexane-2,6-dicarboxylic acid derivatives. More specifically, the present invention relates to novel 2-amino-3-alkoxy-6-fluorobicyclo-[3.1.0]hexane-2,6-dicarboxylic acid derivatives effective for treating and preventing psychiatric disorders such as schizophrenia, anxiety and its associated diseases, bipolar disorder and epilepsy, as well as neurological diseases such as drug dependence, cognitive disorders, Alzheimer's disease, Huntington's chorea, Parkinson's disease, dyskinesia associated with muscular stiffness, cerebral ischemia, cerebral failure, myelopathy and head trauma.

The present invention also relates to the finding that compounds acting as antagonists of mGluR2 and mGluR3, which belong to subgroup II of metabotropic glutamate receptors (mGluR), have therapeutic and prophylactic effects on depressive symptoms.

BACKGROUND ART

In recent years, successive cloning studies of the glutamate receptor gene have been conducted, with the finding that glutamate receptors have a surprisingly large number of subtypes. At present, glutamate receptors are generally divided into two categories: "ionotropic receptors having an ionic channel structure" and "metabotropic receptors coupled with G-protein" (Science, 258, 597–603, 1992). Further, ionotropic receptors are divided into the following three pharmacological groups: N-methyl-D-aspartic acid (NMDA), α-amino-3-hydroxy-5-methylisoxazole-4-propionate (AMPA) and kainate (Science, 258, 597–603, 1992), while metabotropic receptors are divided into 8 groups (type 1 to type 8) (J. Neurosci., 13, 1372–1378, 1993; Neuropharmacol., 34, 1–26, 1995).

Also, metabotropic glutamate receptors are divided into three pharmacological groups. Among them, group II receptors (mGluR2/mGluR3) bind to adenylate cyclase and inhibit forskolin-stimulated accumulation of cyclic adenosine monophosphate (cAMP) (Trends Pharmacol. Sci., 14, 13 (1993)). Thus, it can be concluded that compounds acting as antagonists of group II metabotropic glutamate receptors would be effective for treating or preventing acute and chronic psychiatric and neurological diseases.

An object of the present invention is to provide a drug that is effective for treating and preventing psychiatric disorders such as schizophrenia, anxiety and its associated diseases, bipolar disorder and epilepsy, as well as neurological diseases such as drug dependence, cognitive disorders, Alzheimer's disease, Huntington's chorea, Parkinson's disease, dyskinesia associated with muscular stiffness, cerebral ischemia, cerebral failure, myelopathy and head trauma, wherein the drug acts as an antagonist of group II metabotropic glutamate receptors.

On the other hand, selective serotonin reuptake inhibitors (SSRI), noradrenaline reuptake inhibitors and the like are known as antidepressants, but these inhibitors are not designed based on etiological considerations. Consequently, patients for whom such drugs are not effective are likely to continue to suffer symptoms of depression and experience a reduced quality of life. Thus, there exists a need to develop a drug that is based on etiological considerations, and that addresses a root cause of depressive symptoms.

Another object of the present invention is to provide a new type of antidepressant that is effective for treating and preventing depressive symptoms for which existing drugs are not effective.

DISCLOSURE OF THE INVENTION

As a result of extensive and intensive efforts directed to 2-amino-3-alkoxy-6-fluorobicyclo[3.1.0]hexane-2,6-dicarboxylic acid derivatives, the inventors of the present invention have discovered novel 2-amino-3-alkoxy-6-fluorobicyclo[3.1.0]hexane-2,6-dicarboxylic acid derivatives that have an antagonistic effect on group II metabotropic glutamate receptors. Also, they have conducted animal experiments to test compounds having an antagonistic effect on group II metabotropic glutamate receptors, finding that such compounds are highly effective for treating depressive symptoms.

Namely, the present invention relates to an antidepressant comprising, as an active ingredient, a compound having an antagonistic effect on group II metabotropic glutamate receptors, as well as a novel 2-amino-3-alkoxy-6-fluorobicyclo[3.1.0]hexane-2,6-dicarboxylic acid derivative having an antagonistic effect on group II metabotropic glutamate receptors.

An embodiment of the present invention is directed to an antidepressant comprising, as an active ingredient, a compound having an antagonistic effect on group II metabotropic glutamate receptors.

Another embodiment of the present invention is directed to a 2-amino-3-alkoxy-6-fluorobicyclo[3.1.0]hexane-2,6-dicarboxylic acid derivative of Formula [I]:

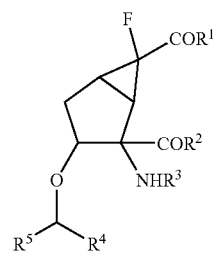

[I]

[wherein $R^1$ and $R^2$, which may be the same or different, each represent a hydroxyl group, a $C_{1-10}$ alkoxy group, a phenoxy group, a naphthyloxy group, a $C_{1-6}$ alkoxy group which is substituted with one or two phenyl groups, a $C_{1-6}$ alkoxy-$C_{1-6}$ alkoxy group, a hydroxy-$C_{2-6}$ alkoxy group, an amino group, an amino group which is substituted with the same or different one or two $C_{1-6}$ alkyl groups, an amino group which is substituted with the same or different one or two $C_{1-6}$ alkoxy-$C_{1-6}$ alkyl groups, an amino group which is substituted with the same or different one or two hydroxy-$C_{2-6}$ alkyl groups, an amino group which is substituted with the same or different one or two $C_{1-6}$ alkoxycarbonyl-$C_{1-6}$ alkyl groups, or a native or non-native amino acid residue represented by $NR^6$—$CHR^7$-A-$CO_2R^8$ (wherein $R^6$ and $R^7$, which may be the same or different, each represent a hydrogen atom, a hydroxy-$C_{1-6}$ alkyl group, a hydroxycarbonyl-$C_{1-6}$ alkyl group, a $C_{1-10}$ alkyl group, a phenyl group, a phenyl-$C_{1-6}$ alkyl group, a hydroxyphenyl group, a hydroxyphenyl-$C_{1-6}$ alkyl group, a naphthyl group, a naphthyl-$C_{1-6}$ alkyl group, an aromatic heterocyclic $C_{1-6}$ alkyl group, a $C_{1-6}$ alkoxy-$C_{1-6}$ alkyl group, an amino-$C_{2-6}$ alkyl group, a guanidino-$C_{2-6}$ alkyl group, a mercapto-$C_{2-6}$ alkyl group, a $C_{1-6}$ alkylthio-$C_{1-6}$ alkyl group or an aminocarbonyl-$C_{1-6}$ alkyl group, or $R^6$ and $R^7$ may together represent a group capable of forming a methylene group, an ethylene group or a propylene group, or may together form a cyclic amino group; $R^8$ represents a hydrogen atom or a protecting group for a carboxyl group; and A represents a single bond, a methylene group, an ethylene group or a propylene group);

$R^3$ represents a $C_{1-10}$ acyl group, a $C_{1-6}$ alkoxy-$C_{1-6}$ acyl group, a hydroxy-$C_{2-10}$ acyl group, a $C_{1-6}$ alkoxycarbonyl-$C_{1-6}$ acyl group, a hydroxycarbonyl-$C_{1-6}$ acyl group, or an amino acid residue represented by $R^9$—NH-A-$CHR^7$—CO (wherein $R^7$ and A are as defined above, and $R^9$ represents a hydrogen atom or a protecting group for an amino group); and $R^4$ and $R^5$, which may be the same or different, each represent a hydrogen atom, a $C_{1-10}$ alkyl group, a $C_{2-10}$ alkenyl group; a phenyl group, a naphthyl group, a 5-membered heteroaromatic ring containing one or more heteroatoms, or a phenyl group substituted with 1 to 5 substituents selected from the group consisting of a halogen atom, a $C_{1-10}$ alkyl group, a $C_{1-10}$ alkoxy group, a trifluoromethyl group, a phenyl group, a hydroxycarbonyl group, an amino group, a nitro group, a cyano group and a phenoxy group, or $R^4$ and $R^5$ may together form a cyclic structure]

or a pharmaceutically acceptable salt or hydrate thereof.

The terms and phrases used herein are defined as follows.

The term "$C_{1-10}$ alkoxy group" refers to a linear or branched alkoxy group containing 1 to 10 carbon atoms. Examples include a methoxy group, an ethoxy group, a propoxy group, an isopropoxy group, a butoxy group, an isobutoxy group, a t-butoxy group, a pentyloxy group and an isopentyloxy group.

The phrase "$C_{1-6}$ alkoxy group which is substituted with one or two phenyl groups" is intended to mean a linear alkyl group containing 1 to 6 carbon atoms or a branched alkyl group containing 3 to 6 carbon atoms, each of which alkyl groups is substituted with one or two phenyl groups. Examples include a benzyl group, a diphenylmethyl group, a 1-phenylethyl group and a 2-phenylethyl group.

The term "$C_{1-6}$ alkoxy-$C_{1-6}$ alkoxy group" is intended to mean a $C_{1-6}$ alkoxy group which is substituted with a $C_{1-6}$ alkoxy group. Examples include a methoxyethoxy group, an ethoxyethoxy group, a propoxyethoxy group, an isopropoxyethoxy group, a butoxyethoxy group, an isobutoxyethoxy group, a t-butoxyethoxy group, a pentyloxyethoxy group, an isopentyloxyethoxy group, a methoxypropoxy group, an ethoxypropoxy group, a propoxypropoxy group, an isopropoxypropoxy group, a butoxypropoxy group, an isobutoxypropoxy group, a t-butoxypropoxy group, a pentyloxypropoxy group and an isopentyloxypropoxy group.

The term "hydroxy-$C_{2-6}$ alkoxy group" is intended to mean a $C_{2-6}$ alkoxy group which is substituted with at least one hydroxyl group. Examples include a 2-hydroxyethoxy group, a 3-hydroxypropoxy group and a 2,3-dihydroxypropoxy group.

The phrase "amino group which is substituted with the same or different one or two $C_{1-6}$ alkyl groups" includes, for example, an N-methylamino group, an N,N-diethylamino group or an N-butyl-N-isopropylamino group.

The phrase "amino group which is substituted with the same or different one or two $C_{1-6}$ alkoxy-$C_{1-6}$ alkyl groups" includes, for example, an N-3-methoxypropylamino group, an N,N-bis(2-ethoxybutyl)amino group or an N-(2-butoxyethyl)-N-(1-ethoxypropyl)amino group.

The phrase "amino group which is substituted with the same or different one or two hydroxy-$C_{2-6}$ alkyl groups" includes, for example, an N-4-hydroxybutylamino group, an N,N-bis(3-hydroxypentyl)amino group or an N-(2-hydroxyethyl)-N-(1-hydroxypentyl)amino group.

The phrase "amino group which is substituted with the same or different one or two $C_{1-6}$ alkoxycarbonyl-$C_{1-6}$ alkyl groups" includes, for example, an N-(3-ethoxycarbonylpropyl)amino group, an N,N-bis(2-methoxycarbonylethyl) amino group or an N-(3-propoxycarbonylpropyl)-N-(2-methoxybutyl)amino group.

The term "hydroxy-$C_{1-6}$ alkyl group" is intended to mean a $C_{1-6}$ alkyl group which is substituted with at least one hydroxyl group. Examples include a hydroxymethyl group, a 1-hydroxyethyl group, a 2-hydroxyethyl group, a 3-hydroxypentyl group and a 2-hydroxy-2-methylbutyl group.

The term "hydroxycarbonyl-$C_{1-6}$ alkyl group" is intended to mean a $C_{1-6}$ alkyl group which is substituted with at least one hydroxycarbonyl group. Examples include a hydroxycarbonylmethyl group, a 4-hydroxycarbonylbutyl group, a 2-hydroxycarbonylethyl group and a 3-hydroxycatbonylpropyl group.

The term "$C_{1-10}$ alkyl group" refers to a linear alkyl group containing 1 to 10 carbon atoms, a branched alkyl group containing 3 to 10 carbon atoms or a cyclic alkyl group containing 3 to 10 carbon atoms. Examples of a linear alkyl group include a methyl group, an ethyl group, a propyl group, a butyl group, a pentyl group, a hexyl group, a heptyl group, an octyl group, a nonyl group and a decyl group. Examples of a branched alkyl group include an isopropyl group, an isobutyl group, a t-butyl group, an isopentyl group, a 1-ethylpropyl group, an isohexyl group, a 2-ethylbutyl group, an isoheptyl group, an isooctyl group, an isononyl group, an isodecyl group, a cyclopropylmethyl group, a 2-(cyclopropyl)ethyl group, a cyclobutylmethyl group and a cyclopentylmethyl group. Examples of a cyclic alkyl group include a cyclopropyl group, a cyclobutyl group, a cyclopentyl group and a cyclohexyl group.

The term "phenyl-$C_{1-6}$ alkyl group" includes, for example, a benzyl group, a 2-phenylethyl group, a 2-phenylpropyl group or a 1-methyl-2-phenylpentyl group.

The term "hydroxyphenyl-$C_{1-6}$ alkyl group" includes, for example, a 4-hydroxybenzyl group, a 2-(4-hydroxy-phenyl) ethyl group, a 3-(4-hydroxyphenyl)propyl group or a 4-(4-hydroxyphenyl)butyl group.

The term "naphthyl-$C_{1-6}$ alkyl group" includes, for example, a 1-naphthylmethyl group, a 2-naphthylmethyl group, a 2-(1-naphthyl)ethyl group or a 2-(2-naphthyl)ethyl group.

The term "naromatic heterocyclic $C_{1-6}$ alkyl group" is intended to mean a $C_{1-6}$ alkyl group attached to an aromatic heterocyclic ring such as an indole ring or an imidazole ring. Examples include an indole-3-ylmethyl group and a 1H-imidazole-4-ylmethyl group.

The term "$C_{1-6}$ alkoxy-$C_{1-6}$ alkyl group" is intended to mean a $C_{1-6}$ alkyl group which is substituted with at least one $C_{1-6}$ alkoxy group. Examples include a 2-methoxyethyl group, a 3-ethoxypentyl group and a 3-propoxybutyl group.

The term "amino-$C_{2-6}$ alkyl group" includes, for example, a 2-aminoethyl group, a 3-aminopropyl group, a 4-aminobutyl group, a 5-aminopentyl group or a 6-aminohexyl group.

The term "guanidino-$C_{2-6}$ alkyl group" includes, for example, a 2-guanidinoethyl group, a 3-guanidinopropyl group, a 4-guanidinobutyl group, a 5-guanidinopentyl group or a 6-guanidinohexyl group.

The term "mercapto-$C_{2-6}$ alkyl group" includes, for example, a mercaptomethyl group, a 2-mercaptoethyl group or a 3-mercaptopropyl group.

The term "$C_{1-6}$ alkylthio-$C_{1-6}$ alkyl group" includes, for example, a methylthiomethyl group, a 2-methylthioethyl group, a 3-methylthiopropyl group, a 4-methylthiobutyl group, a 5-methylthiopentyl group or a 6-methylthiohexyl group.

The term "aminocarbonyl-$C_{1-6}$ alkyl group" is intended to mean a $C_{1-6}$ alkyl group which is substituted with at least one aminocarbonyl group. Examples include an aminocarbonylmethyl group, a 2-aminocarbonylethyl group, a 2-aminocarbonylpropyl group and a 4-aminocarbonylbutyl group.

The phrase "protecting group for a carboxyl group" includes, for example, a $C_{1-10}$ alkyl group, a phenyl-$C_{1-6}$ alkyl group, a nitrobenzyl group or a methoxybenzyl group (see E. Wünsch, "Synthese von Peptiden" in "Houben-Weyl Methoden der Organishen Chemie" Vol. XV/1,2 and E. Gross. J. Meienhofer, "The Peptides" Vol. 1 to Vol. 5).

The term "$C_{1-10}$ acyl group" refers to a linear or branched acyl group containing 1 to 10 carbon atoms. Examples include a formyl group, an acetyl group, a 1-methylpropanoyl group and a hexanoyl group.

The term "$C_{1-6}$ alkoxy-$C_{1-6}$ acyl group" is intended to mean a $C_{1-6}$ acyl group which is substituted with at least one $C_{1-6}$ alkoxy group. Examples include a 3-ethoxybutanoyl group, a 3-isopropoxypentanoyl group and a 4-ethoxyhexanoyl group.

The term "hydroxy-$C_{2-10}$ acyl group" is intended to mean a $C_{2-10}$ acyl group which is substituted with at least one hydroxyl group. Examples include a 4-hydroxybutanoyl group and a 2-(hydroxymethyl)butanoyl group.

The term "$C_{1-6}$ alkoxycarbonyl-$C_{1-6}$ acyl group" includes, for example, a 3-methoxycarbonylpropanoyl group or a 4-ethoxycarbonylbutanoyl group.

The term "hydroxycarbonyl-$C_{1-6}$ acyl group" includes, for example, a 3-hydroxycarbonyl-2-methylbutanoyl group or a 5-hydroxycarbonylpropanoyl group.

The phrase "protecting group for an amino group" includes, for example, a $C_{1-10}$ acyl group, a $C_{1-6}$ alkoxy-$C_{1-6}$ acyl group, a benzyloxycarbonyl group, a nitrobenzyloxycarbonyl group or a methoxybenzyloxycarbonyl group (see E. Wünsch, "Synthese von Peptiden" in "Houben-Weyl Methoden der Organishen Chemie", Vol. XV/1,2 and E. Gross, J. Meienhofer, "The Peptides" Vol. 1 to Vol. 5).

The term "$C_{2-10}$ alkenyl group" refers to a linear alkenyl group containing 2 to 10 carbon atoms, a branched alkenyl group containing 3 to 10 carbon atoms or a cyclic alkenyl group containing 5 to 10 carbon atoms, each of which alkenyl groups has at least one double bond. Examples include a 2-propenyl group, a 1-methyl-2-butenyl group, a 2-pentenyl group, a 2-methyl-2-hexenyl group and a 2-cyclopentenyl group.

The phrase "5-membered heteroaromatic ring containing one or more heteroatoms" is intended to mean an aromatic 5-membered ring containing the same or different one or more heteroatoms in the ring. Examples include thiophene, pyrrole, furan, pyrazole, isoxazole, isothiazole, imidazole, oxazole, thiazole, oxadiazole and thiadiazole.

The term "native or non-native amino acid residue" includes a residue such as glycine, alanine, valine, leucine, isoleucine, proline, phenylalanine, tyrosine, tryptophan, histidine, serine, threonine, cysteine, methionine, aspartic acid, asparagine, glutamic acid, glutamine, lysine, ornithine or arginine, with native amino acid residues being preferred.

The definition "phenyl group substituted with 1 to 5 substituents selected from the group consisting of a halogen atom, a $C_{1-10}$ alkyl group, a $C_{1-10}$ alkoxy group, a trifluoromethyl group, a phenyl group, a hydroxycarbonyl group, an amino group, a nitro group, a cyano group and a phenoxy group" is intended to mean a phenyl group substituted with 1 to 5 substituents selected from the group consisting of a fluorine atom, a chlorine atom, a bromine atom, an iodine atom, a $C_{1-10}$ alkyl group, a cyclic $C_{3-10}$ alky group, a $C_{1-10}$ alkoxy group, a cyclic $C_{3-10}$ alkoxy group, a trifluoromethyl group, a phenyl group, a hydroxycarbonyl group, an amino group, a nitro group, a cyano group and a phenoxy group. A phenyl group substituted with one substituent includes, for example, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-methylphenyl group, a 3-methylphenyl group, a 4-methylphenyl group, a 2-ethylphenyl group, a 3-ethylphenyl group, a 4-ethylphenyl group, a 2-isopropylphenyl group, a 3-isopropylphenyl group, a 4-isopropylphenyl group, a 2-cyclopropylphenyl group, a 3-cyclopropylphenyl group, a 4-cyclopropylphenyl group, a 2-cyclohexylphenyl group, a 3-cyclohexylphenyl group, a 4-cyclohexylphenyl group, a 2-methoxyphenyl group, a 3-methoxyphenyl group, a 4-methoxyphenyl group, a 2-isopropoxyphenyl group, a 3-isopropoxyphenyl group, a 4-isopropoxyphenyl group, a 2-cyclobutyloxyphenyl group, a 3-cyclobutyloxyphenyl group, a 4-cyclobutyloxyphenyl group, a 2-cyclohexyloxyphenyl group, a 3-cyclohexyloxyphenyl group, a 4-cyclohexyloxyphenyl group, a 2-trifluoromethylphenyl group, a 3-fluoromethylphenyl group, a 4-trifluoromethylphenyl group, a 2-phenylphenyl group, a 3-phenylphenyl group, a 4-phenylphenyl group, a 2-hydroxycarbonylphenyl group, a 3-hydroxycarbonylphenyl group, a 4-hydroxycarbonylphenyl group, a 2-aminophenyl group, a 3-aminophenyl group, a 4-aminophenyl group, a 2-nitrophenyl group, a 3-nitrophenyl group, a 4-nitrophenyl group, a 2-cyanophenyl group, a 3-cyanophenyl group, a 4-cyanophenyl group, a 2-phenoxyphenyl group, a 3-phenoxyphenyl group or a 4-phenoxyphenyl group. A phenyl group substituted with two substituents includes, for example, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3-dichlorophenyl group, a 2,4-dichlorophenyl group, a 2,5-dichlorophenyl group, a 2,6-dichlorophenyl group, a 3,4-dichlorophenyl group, a 3,5-dichlorophenyl group, a 2,3-dibromophenyl group, a 2,4-dibromophenyl group, a 2,5-dibromophenyl group, a 2,6-dibromophenyl group, a 3,4-dibromophenyl group, a 3,5-dibromophenyl group, a 2,3-diiodophenyl group, a 2,4-diiodophenyl group, a 2,5-diiodophenyl group, a 2,6-diiodophenyl group, a 3,4-diiodophenyl group, a 3,5-diiodophenyl group, a 3-chloro-4-fluorophenyl group, a 4-chloro-3-fluorophenyl group, a 3-bromo-4-fluorophenyl group, a 4-bromo-3-fluorophenyl group, a 4-bromo-3-chlorophenyl group, a 3-bromo-4-chlorophenyl group, a 3-chloro-4-methylphenyl group, a 4-chloro-3-methylphenyl group, a 3-fluoro-4-methylphenyl group, a 4-fluoro-3-methylphenyl group, a 3-fluoro-4-methoxyphenyl group, a 4-fluoro-3-methoxyphenyl group, a 3-bromo-4-methoxyphenyl group, a 4-bromo-3-methoxyphenyl group, a 3-chloro-4-phenoxyphenyl group, a 4-chloro-3-phenoxyphenyl group, a 3-chloro-4-nitophenyl group, a 4-chloro- 3-nitrophenyl group, a 4-bromo-3-nitrophenyl group, a 3-bromo-4-nitrophenyl group, a 3-amino-4-bromophenyl group, a 4-amino-3-bromophenyl group, a 3-bromo-4-hydroxycarbonyl group, a 4-bromo-3-hydroxycarbonylphenyl group, a 4-fluoro-3-hydroxycarbonyl group, a 3-fluoro-4-hydroxycarbonylphenyl group, a 4-fluoro-3-hydroxycarbonyl group, a 3-cyano-4-fluorophenyl group, a 3-cyano-4-fluorophenyl group, a 4-cyano-3-methylphenyl group, a 3-cyano-4-methylphenyl group, a 3-cyano-4-methoxyphenyl group or a 4-cyano-3-methoxyphenyl group. A phenyl group substituted with three substituents includes, for example, a 2,3,4-trifluorophenyl group, a 3,4,5-trifluorophenyl group, a 3,4,5-trichlorophenyl group, a 3,5-dichloro-4-methoxyphenyl group or a 3,5-dibromo-4-methoxyphenyl group. A phenyl group substituted with four substituents includes, for example, a 2,5-dibromo-3,4-dimethoxyphenyl group or a 3,4-dibromo-2,5-dimethoxyphenyl group. A phenyl group substituted with five substituents includes, for example, a 2,3,4,5,6-pentafluorophenyl group.

The definition "$R^4$ and $R^5$ may together form a cyclic structure" includes, for example, a cyclopropyl group, a cyclobutyl group, a cyclopentyl group, a cyclohexyl group, a cycloheptyl group, a cyclooctyl group, a cyclopentenyl group, a cyclohexenyl group, a cycloheptenyl group, a cyclooctenyl group, an oxacyclobutyl group, an oxacyclopentyl group, an oxacyclohexyl group, an oxacycloheptyl group, an oxacyclooctyl group, an azacyclobutyl group, an azacyclopentyl group, an azacyclohexyl group, an azacycloheptyl group or an azacyclooctyl group.

In addition, the term "pharmaceutically acceptable salt" as used herein includes, for example, a salt with a mineral acid such as sulfuric acid, hydrochloric acid or phosphoric acid, a salt with an organic acid such as acetic acid, oxalic acid, lactic acid, tartaric acid, fumaric acid, maleic acid, methanesulfonic acid or benzenesulfonic acid, a salt with an amine such as trimethylamine or methylamine, or a salt with a metal ion such as sodium ion, potassium ion or calcium ion.

A compound of Formula [I] has five asymmetric carbon atoms in its bicyclo[3.1.0]hexane ring. Configurations preferred for the present invention are optically active forms having absolute structures represented by Formulae [II] and [III], but they may be present in the form of an enantiomer or an enantiomer mixture including a racemate. Namely, the compound of the present invention encompasses all its optically active forms represented by the following Formulae [II] and [III] and their enantiomer mixtures including racemates and diastereomer mixtures.

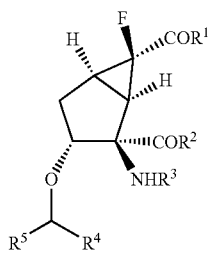

[II]

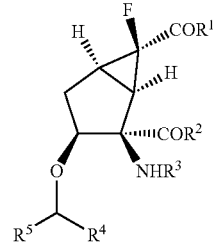

[III]

The compound of the present invention can also be present as a hydrate or a solvate with an organic solvent.

Further, when the compounds of Formula [I], [II] or [III], wherein one or both of $R^1$ and $R^2$ represent other than a hydroxyl group or $R^3$ represents other than a hydrogen atom are ester or amide derivatives, these derivatives have no effect on group II metabotropic glutamate receptors. However, such ester and amide derivatives will be hydrolyzed in the body and hence converted into 2-amino-3-alkoxy-6-fluorobicyclo[3.1.0]hexane-2,6-dicarboxylic acid derivatives capable of acting on group II metabotropic glutamate receptors. Thus, these ester and amide derivatives are extremely useful because they serve as prodrugs.

The compound of the present invention represented by Formula [I] can be provided as shown in the production schemes below. In the schemes, $R^1$, $R^2$, $R^3$, $R^4$, $R^5$, $R^6$, $R^7$, $R^8$ and $R^9$ are as defined above; $R^{10}$ represents an aryl- or alkyl-sulfonyl group such as a mesyl group, a phenylsulfonyl group, a tosyl group or a trifluoromethylsulfonyl group, a benzoyl group or a 4-nitrobenzoyl group; $R^{11}$, $R^{12}$, $R^{13}$ and $R^{14}$, which may be the same or different, each represent a $C_{1-10}$ alkoxy group, a phenoxy group, a naphthyloxy group, a $C_{1-6}$ alkoxy group which is substituted with one or two phenyl groups, a $C_{1-6}$ alkoxy-$C_{1-6}$ alkoxy group or a hydroxy-$C_{2-6}$ alkoxy group; and $R^{15}$ represents an amino group, an amino group in which one or two hydrogen atoms are substituted with the same or different $C_{1-6}$ alkyl groups, an amino group in which one or two hydrogen atoms are substituted with the same or different $C_{1-6}$ alkoxy-$C_{1-6}$ alkyl groups, an amino group in which one or two hydrogen atoms are substituted with the same or different hydroxy-$C_{2-6}$ alkyl groups, an amino group in which one or two hydrogen atoms are substituted with the same or different $C_{1-6}$ alkoxycarbonyl-$C_{1-6}$ alkyl groups, or $NR^6$—$CHR^7$-A-$CO_2R^8$.

First, Intermediate (6) which is required to synthesize Compound [I] of the present invention can be prepared as follows.

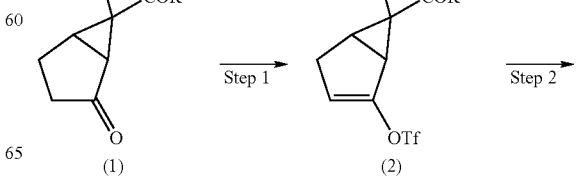

-continued

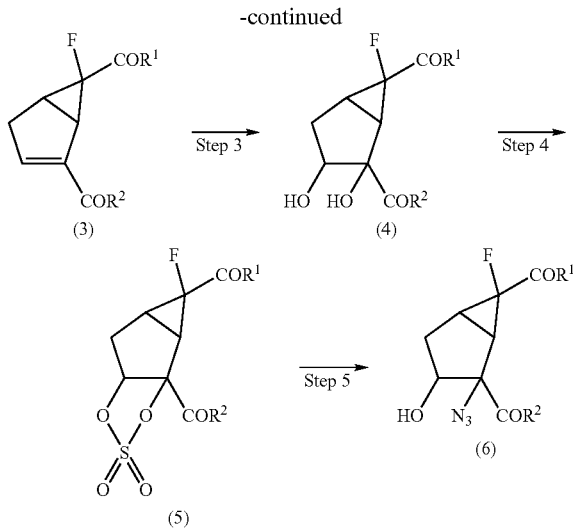

Step 1: In an inert solvent and in the presence of a base, for example, Compound (1) may be reacted with a trifluoromethanesulfonylating agent such as trifluoromethanesulfonic anhydride or N-phenyl-bis(trifluoromethanesulfonimide) to give Compound (2). Examples of an inert solvent available for use include hydrocarbon solvents such as benzene, toluene and hexane, halogenated solvents such as dichloromethane, chloroform and carbon tetrachloride, ether solvents such as tetrahydrofuran, diethyl ether and 1,2-dimethoxyethane, as well as acetonitrile, or mixtures thereof. Examples of a base available for use include amines such as triethylamine, N-methylmorpholine, diisopropylethylamine and pyridine, inorganic bases such as potassium hydride and sodium hydride, metal amides such as lithium diisopropylamide, potassium bis(trimethylsilyl)amide and lithium hexamethyldisilazane, as well as metal alcoholates such as sodium methoxide and potassium t-butoxide.

Step 2: In an inert solvent and in the presence of a transition metal catalyst, for example, Compound (2) may be reacted with carbon monoxide and $R^2OH$ in the presence of an organic base such as triethylamine, N-methylmorpholine, diisopropylethylamine or pyridine or an inorganic base such as potassium carbonate or sodium bicarbonate to give Compound (3) (see Tetrahedron Letters 26, 1109(1985)). As used herein, a transition metal catalyst includes, e.g., a zero-valent palladium reagent, which may be prepared in the reaction system using divalent palladium such as palladium(II) acetate and a ligand such as triphenyl- phosphine or 2,2'-bis(diphenylphosphino)-1,1-binaphthyl (BINAP). Alternatively, it is also possible to directly use a zero-valent palladium reagent such as tetrakis(triphenyl-phosphine)palladium(0). Examples of an inert solvent available for use include hydrocarbon solvents such as benzene, toluene and hexane, ether solvents such as tetrahydrofuran, diethyl ether and 1,2-dimethoxyethane, as well as acetonitrile, N,N-dimethylformamide, or mixtures thereof.

Step 3: In an inert solvent, for example, Compound (3) may be oxidized into diol through common diol formation using osmium tetroxide or the like (see M. Hudlicky, "Oxidations in Organic Chemistry") or Sharpless asymmetric cis-dihydroxylation using AD-mix as a regent (Sharpless AD)(see Tetrahedron Asymmetry 4, 133 (1993), J. Org. Chem. 57, 2768(1992), J. Org. Chem. 61, 2582 (1996)), thereby giving Compound (4). Examples of an inert solvent available for use include alcohol solvents such as t-butyl alcohol, hydrocarbon solvents such as benzene, toluene and hexane, ether solvents such as tetrahydrofuran, diethyl ether and 1,2-dimethoxyethane, as well as acetonitrile, acetone, N,N-dimethylformamide, water, or mixtures thereof.

Step 4: For example, Compound (4) may be reacted with thionyl chloride in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane), acetonitrile or any mixture thereof and in the presence or absence of an organic base (e.g., triethylamine, N-methylmorpholine, diisopropylethylamine, pyridine) or an inorganic base (e.g., potassium carbonate, sodium bicarbonate). This reaction is followed by oxidation using a common oxidizing agent such as hydrogen peroxide, OXONE® or ruthenium trichloride/sodium metaperiodate (see M. Hudlicky, "Oxidations in Organic Chemistry") in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane), acetonitrile, acetone, water or any mixture thereof, thereby giving Compound (5).

Step 5: For example, Compound (5) may be reacted with sodium azide in an inert solvent such as an ether solvent (e.g., tetrahydrofuran), a ketone (e.g., acetone), N,N-dimethylformamide, water or any mixture thereof, followed by hydrolysis to give Compound (6) (see J. Am. Chem. Soc. 110, 7538(1988)).

Intermediate (9) which is required to synthesize the compound of the present invention having the relative stereochemical configuration represented by Formula [III] can be prepared from Compound (7) having the following relative configuration among those possible for Intermediate (6).

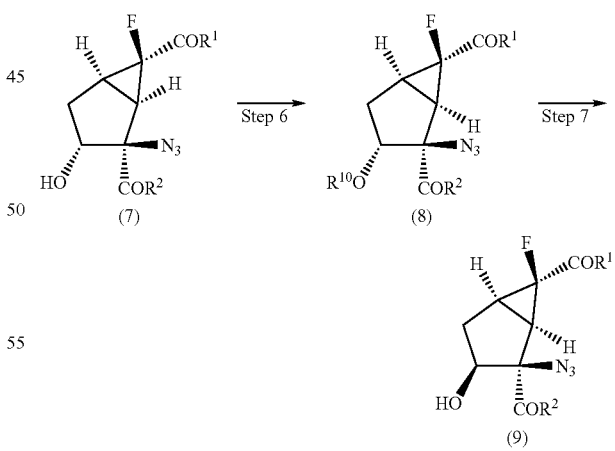

Step 6: For example, the hydroxyl group of Compound (7) in which $R^1$ and $R^2$ represent other than a hydroxyl group may be reacted with a trifluoromethanesulfonylating agent such as trifluoromethanesulfonic anhydride or N-phenyl-bis(trifluoromethanesulfonimide) or an alkyl- or aryl-sulfonylating agent such as methanesulfonic chloride, benzenesulfonic chloride or toluenesulfonic chloride in an inert solvent such as a hydrocarbon solvent (e.g., benzene, toluene, hexane, cyclohexane), a halogenated solvent (e.g., dichloromethane, chloroform, carbon tetrachloride), an ether solvent (e.g., tetrahydrofuran, diethyl ether, 1,2-dimethoxyethane), an amide (e.g., N,N-dimethylformamide, N-methyl-2-pyrrolidinone), dimethyl sulfoxide or any mixture thereof and in the presence of an inorganic base (e.g., sodium hydride, potassium hydride, potassium carbonate, sodium carbonate, sodium hydroxide, potassium hydroxide), a metal amide (e.g., lithium bis(trimethylsilyl)amide, lithium diisopropylamide, sodium amide), an organic base (e.g., triethylamine, pyridine, diisopropylethylamine, 4-(N,N-dimethylamino)pyridine, 2,6-di-t-butylpyridine) or a base (e.g., potassium t-butoxide), thereby giving Compound (8).

Step 7: For example, Compound (8) may be reacted with an alkali hydroxide such as potassium hydroxide or sodium hydroxide, a nitrite salt such as potassium nitrite (see Tetrahedron Lett., 3183 (1975)) or potassium superoxide (see Tetrahedron Lett. 34, 8029 (1993)) in an inert solvent such as a hydrocarbon solvent (e.g., benzene, toluene, hexane, cyclohexane), a halogenated solvent (e.g., dichloromethane, chloroform, carbon tetrachloride), an ether solvent (e.g., tetrahydrofuran, diethyl ether, 1,2-dimethoxyethane), an amide (e.g., N,N-dimethylformamide, N-methyl-2-pyrrolidinone), an alcohol solvent (e.g., dimethyl sulfoxide, methanol, ethanol), water or any mixture thereof and in the presence or absence of crown ether, thereby giving Intermediate (9).

Alternatively, Compound (7) may be directly converted into Compound (9) through the Mitsunobu reaction with a benzoic acid derivative in the presence of a dehydrocondensing agent such as diethyl azodicarboxylate and triphenylphosphine (see D. L. Hughes, OR, 42, 335 (1992)).

Intermediate (6) prepared above can be converted into Compound [I] of the present invention through the following Steps 8, 9 and 10.

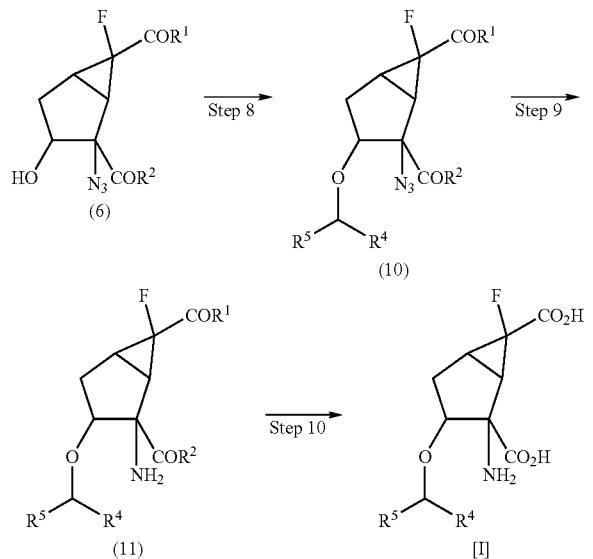

Step 8: For example, the hydroxyl group of Compound (6) in which $R^1$ and $R^2$ represent other than a hydroxyl group may be reacted with a compound of the formula $R^4R^5CHX$ (wherein X represents a 2,2,2-trichloroacetimidoyloxy group) in an inert solvent such as a hydrocarbon solvent (e.g., benzene, toluene, hexane, cyclohexane), a halogenated solvent (e.g., dichloromethane, chloroform, carbon tetrachloride), an ether solvent (e.g., tetrahydrofuran, diethyl ether, 1,2-dimethoxyethane) or any mixture thereof and in the presence of a Brönsted acid catalyst (e.g., trifluoromethanesulfonic acid, trifluoroacetic acid, hydrogen chloride) or a Lewis acid catalyst (e.g., boron trifluoride/diethyl ether complex, zinc chloride, tin chloride, trimethylsilyl/trifluoromethanesulfonate), thereby giving Compound (10) (see J. Chem. Soc. Perkin Trans. 1, 2247(1985), Synthesis, 568 (1987)).

Alternatively, for example, the hydroxyl group of Compound (6) in which $R^1$ and $R^2$ represent other than a hydroxyl group may also be reacted with a compound of the formula $R^4R^5CHX$ (wherein X represents other than a 2,2,2-trichloroacetimidoyloxy group) in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane), an amide (e.g., N,N-dimethylformamide, N-methyl-2-pyrrolidinone), dimethyl sulfoxide or any mixture thereof and in the presence of an inorganic base (e.g., sodium hydride, potassium hydride, potassium carbonate, sodium carbonate, sodium hydroxide, potassium hydroxide), a metal amide (e.g., lithium bis(trimethylsilyl)amide, lithium diisopropylamide, sodium amide), an organic base (e.g., triethylamine, diisopropylethylamine, 4-(N,N-dimethylamino)pyridine, 2,6-di-t-butylpyridine) or a base (e.g., potassium t-butoxide), thereby giving Compound (10). In this case, X is a leaving group and intended to mean a halogen atom, tosylsulfonate, trifluoromethanesulfonate, tolylsulfonate, etc.

Step 9: Compound (10) can be converted into Compound (11) of the present invention, for example, through common reduction of an azide group typified by the Staudinger reaction with triethyl phosphite, trimethylphosphine, tributylphosphine, triphenylphosphine or the like in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane), acetonitrile, acetone, water or any mixture thereof (see Bull. Chem. Soc. Fr., 815 (1985)); hydrogenation in the presence of a metal catalyst such as palladium/carbon or palladium black in an inert solvent such as an alcohol (e.g., ethanol, methanol), an ester (e.g., ethyl acetate), N,N-dimethylformamide, water or any mixture thereof; or hydride reduction with lithium aminoborohydride or the like (see A. F. Abdel-Magid, "Reductions in Organic Synthesis").

Step 10: The moieties $COR^1$ and $COR^2$ in Compound (11) may be converted into carboxylic acids through common hydrolysis (see T. W. Greene, P. G. M. Wuts, "Protective Groups in Organic Synthesis") to give Compound (I) of the present invention.

Compounds (13) and (14) of the present invention, which take the form of a monoester or monoamide derivative, can be prepared from Compound (11) or (12) through the following Steps 11 and 12.

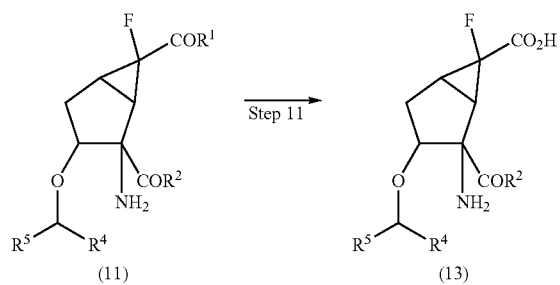

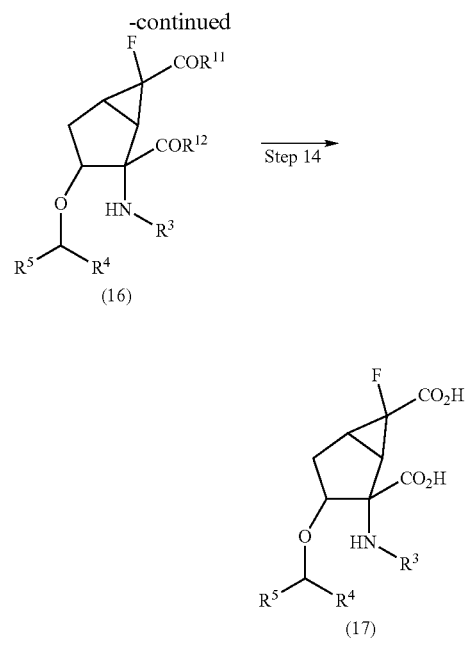

Step 11: The moiety COR$^1$ in Compound (11) may be converted into a carboxylic acid through common hydrolysis for a short period of time or at low temperature (see T. W. Greene, P. G. M. Wuts, "Protective Groups in Organic Synthesis") to give Compound (13) of the present invention.

Step 12: The carboxylic acid moiety on the 6-position carbon of Compound (12) may be subjected to common esterification (see T. W. Greene, P. G. M. Wuts, "Protective Groups in Organic Synthesis") or common peptide bond formation for amino acids in the presence of a compound represented by R$^{15}$—H (see E. Gross. J. Meienhofer, "The Peptides" and J. P. Greenstein, M. Witntz, "Chemistry of the Amino Acids") to form an ester or amide bond, thereby giving Compound (14) of the present invention.

Amide derivatives (17) and (22) can be prepared from Compound (15) or (18) through the following Steps 13, 14, 15, 16, 17 and 18.

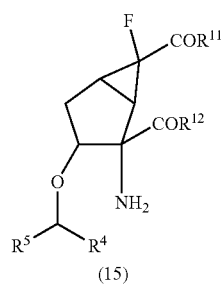

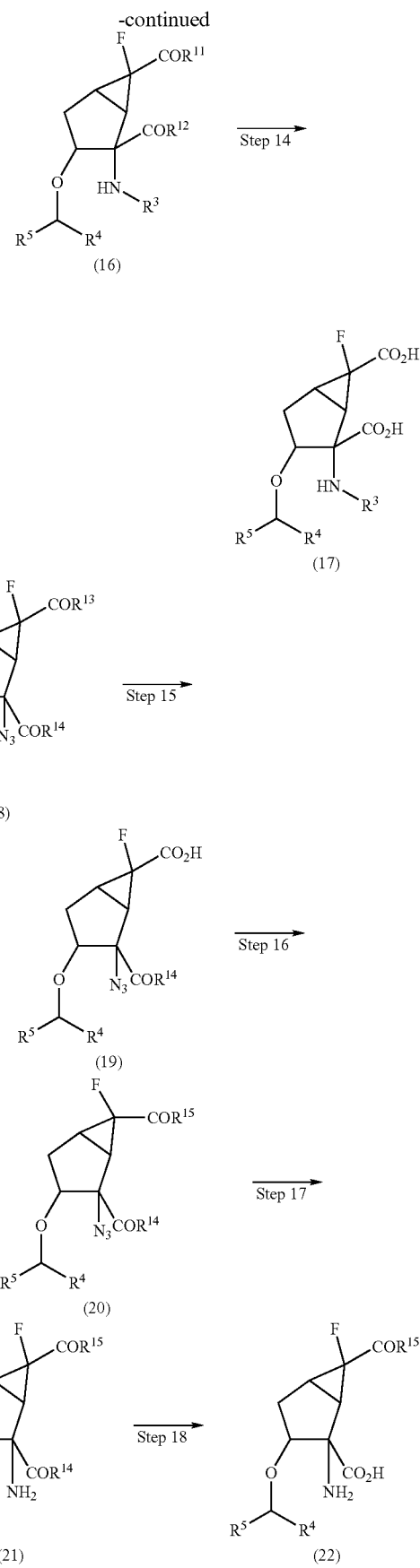

15

Step 13: For example, the amino group of Compound (15) may be reacted with a compound of the formula $R^3X$ or $R^3OR^3$ in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane), an amide (e.g., N,N-dimethylformamide, N-methyl-2-pyrrolidinone), dimethyl sulfoxide or any mixture thereof and in the presence or absence of an organic base such as triethylamine, pyridine, morpholine, diisopropylethylamine, 4-(N,N-dimethylamino)pyridine or 2,6-di-t-butylpyridine, thereby giving Compound (16). In the above formula, X is a leaving group and includes, for example, a halogen atom, an ethoxycarbonyloxy group or a phenoxycarbonyloxy group. Alternatively, Compound (16) can also be prepared by common amide bond formation with a compound of the formula $R^3OH$ (see E. Gross, J. Meienhofer, "The Peptides" and J. P. Greenstein, M. Witntz, "Chemistry of the Amino Acids", Vol. 2).

Step 14: Common deprotection (see T. W. Greene, P. G. M. Wuts, "Protective Groups in Organic Synthesis") may be performed on Compound (16) to convert its ester moieties into carboxylic acids and, when $R^3$ is $COCHR^6NHR^7$, to remove the protecting group $R^7$ to give an amino group, thereby giving a 2-amide derivative (17).

Step 15: The ester bond on the 6-position carbon of Compound (18) may be subjected to common hydrolysis for a short period of time or at low temperature (see T. W. Greene, P. G. M. Wuts, "Protective Groups in Organic Synthesis"), thereby giving Compound (19).

Step 16: The carboxylic acid moiety of Compound (19) may be subjected to common peptide bond formation for amino acids in the presence of a compound represented by $R^{15}$—H (see E. Gross, J. Meienhofer, "The Peptides" and J. P. Greenstein, M. Witntz, "Chemistry of the Amino Acids"), thereby giving Compound (20).

Step 17: Compound (20) can be converted into Compound (21), e.g., through common reduction of an azide group typified by the Staudinger reaction with triethyl phosphate, trimethylphosphine, tributylphosphine, triphenylphosphine or the like in an inert solvent such as a hydrocarbon solvent (e.g., benzene, toluene, hexane), a halogenated solvent (e.g., dichloromethane, chloroform, carbon tetrachloride), an ether solvent (e.g., tetrahydrofuran, diethyl ether, 1,2-dimethoxyethane), acetonitrile, acetone, water or any mixture thereof (see Bull. Chem. Soc. Fr., 815(1985)); hydrogenation in the presence of a metal catalyst such as palladium/carbon or palladium black in an inert solvent such as an alcohol (e.g., ethanol, methanol), an ester (e.g., ethyl acetate), N,N-dimethylformamide, water or any mixture thereof; or hydride reduction with lithium aminoborohydride or the like (see A. F. Abdel-Magid "Reductions in Organic Synthesis").

Step 18: An ester bond of Compound (21) may be subjected to common hydrolysis (see T. W. Greene, P. G. M. Wuts, "Protective Groups in Organic Synthesis"), thereby giving Compound (22) of the present invention.

As used herein, the phrase "compound having an antagonistic effect on group II metabotropic glutamate receptors" is intended to mean a compound that shows a dose-dependent inhibitory effect in receptor binding assay and has the mGluR2/R3 affinity, equivalent to or higher than glutamic acid, as assayed using mGluR2- and mGluR3-expressing cells according to Mol. Pharmacol., 53, 228–233 (1998), and that antagonizes the inhibitory effect of glutamic acid on forskolin-stimulated cAMP levels, as measured with a cAMP assay kit. Alternatively, it is intended to mean a compound that antagonizes glutamic acid-induced GTPγS binding, as measured by GTPγS binding assay.

The compound of the present invention may be formulated into a pharmaceutical preparation in combination with one or more pharmaceutically acceptable carriers, excipients and diluents. Examples of these carriers, excipients and diluents include water, lactose, dextrose, fructose, sucrose, sorbitol, mannitol, polyethylene glycol, propylene glycol, starch, gum, gelatin, alginate, calcium silicate, calcium phosphate, cellulose, water syrup, methylcellulose, polyvinylpyrrolidone, alkyl parahydroxybenzoates, talc, magnesium stearate, stearic acid, glycerine, as well as various oils such as sesame oil, olive oil and soybean oil.

After being mixed with these carriers, excipients or diluents and, if necessary, commonly used additives such as extenders, binders, disintegrating agents, pH regulators and solubilizers, the compound of the present invention may be formulated using common techniques into oral or parenteral preparations such as tablets, pills, capsules, granules, powders, solutions, emulsions, suspensions, ointments, injections or skin patches, and particularly formulated as an antagonist of group II metabotropic glutamate receptors.

Although the compound of the present invention may be orally or parenterally administered to adult patients in an amount of 0.01 to 500 mg as a single dose or in divided doses per day, oral administration is preferred in terms of easy medication and drug efficacy. It should be noted that the amount of the compound to be administered may also be increased or decreased as appropriate for the type of disease to be treated, the age, body weight and condition of a patient, etc.

BEST MODE FOR CARRYING OUT THE INVENTION

Figure 1:
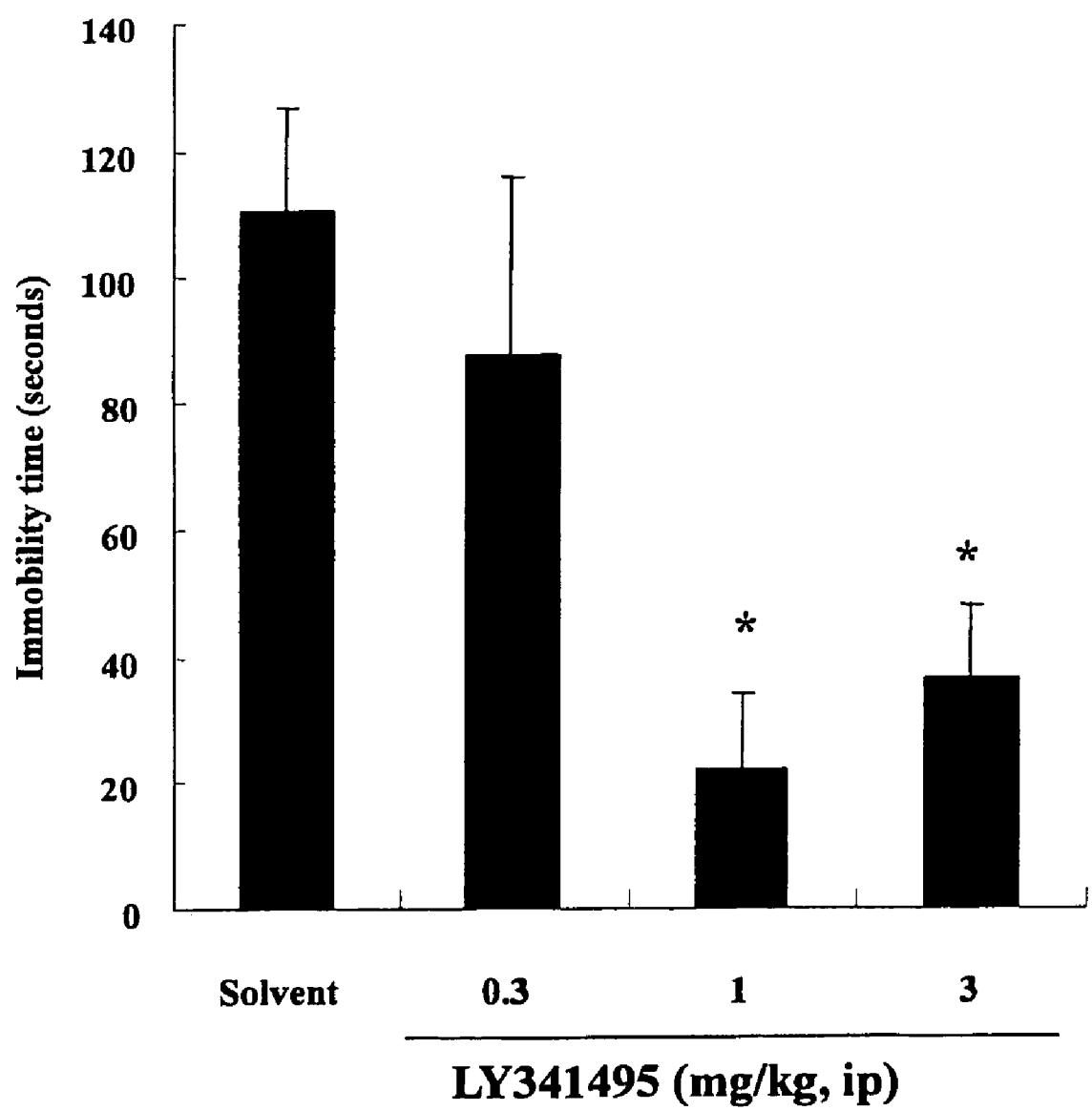
FIGS. 1 and 2 are graphs showing the immobility time in the forced swimming test, measured for rats administered with the known group II metabotropic glutamate receptor antagonist LY341495 (Journal of Medicinal Chemistry 1998, 41, 358–378) and Compound 34 of the present invention, respectively, to evaluate the antidepressant effect of these compounds.

The present invention will be further described in more detail in the following examples and test examples, which are not intended to limit the scope of the invention.

Reference Example 1

Synthesis of (1R,2R,3R,5R,6R)-2-azide-3-hydroxy-6-fluorobicyclo[3.1.0]hexane-2,6-dicarboxylic acid 2-benzyl ester 6-ethyl ester (1) A solution of diisopropylamine (7.83 g) in tetrahydrofuran (84 mL) was cooled to 0° C. and a 2.47 M hexane solution of butyllithium (28.8 mL) was added thereto, followed by stirring for 15 minutes. After this solution was cooled to −62° C., a solution of (1R,5R,6R)-6-fluoro-2-oxobicyclo[3.1.0]hexane-6-carboxylic acid ethyl ester (12.0 g) in tetrahydrofuran (40 mL) was added dropwise while maintaining a temperature of −62° C. to −58° C. After 1 hour, a solution of N-phenyl-bis(trifluoromethanesulfonimide)(25.3 g) in tetrahydrofuran (84 mL) was added dropwise over 15 minutes while maintaining a temperature of −62° C. to −60° C. The reaction solution was warmed to room temperature without heating and then stirred for an additional 1 hour. After addition of saturated aqueous sodium bicarbonate, the reaction mixture was extracted with diethyl ether. The organic layer was washed with water and saturated aqueous sodium chloride, and then dried over anhydrous magnesium sulfate. After the drying agent was filtered off, the filtrate was concentrated under reduced pressure and the resulting residue was purified by column chromatography (silica gel: Wako gel C200 (Wako Pure Chemical Industry Ltd.), developing solvent: hexane/ethyl acetate =20/1). The (1R,5R,6R)-6-fluoro-2-trifluoromethanesulfonyloxybicyclo[3.1.0]hex-2-ene-6-carboxylic acid ethyl ester thus prepared was immediately dissolved in N,N-dimethylformamide (195 mL). To this solution, palladium acetate (389 mg), triphenylphosphine (910 mg), benzyl alcohol (12.5 g) and triethylamine (11.7 g) were added and stirred under a carbon monoxide atmosphere at room temperature for 4.5 hours. After addition of 1N hydrochloric acid, the reaction mixture was extracted twice with diethyl ether. The combined organic layers were washed with saturated aqueous sodium bicarbonate and saturated aqueous sodium chloride, and then dried over anhydrous magnesium sulfate. After the drying agent was filtered off, the filtrate was concentrated under reduced pressure and the resulting residue was purified by column chromatography (silica gel: Wako gel C200 (Wako Pure Chemical Industry Ltd.), developing solvent: hexane/ethyl acetate=10/1 to 1/1) to give (1R,5R,6R)-6-fluorobicyclo[3.1.0]hex-2-ene-2,6-dicarboxylic acid 2-benzyl ester 6-ethyl ester (6.42 g).

mp 90–91° C.

(2) AD-mix-β (29.3 g, Aldlich) and methanesulfonamide (5.96 g) were added to (1R,5R,6R)-6-fluorobicyclo[3.1.0]hex-2-ene-2,6-dicarboxylic acid 2-benzyl ester 6-ethyl ester (6.36 g) suspended in t-butanol (150 mL) and water (150 mL), followed by stirring at 40° C. for 5 days. After addition of sodium bisulfite, the reaction mixture was stirred at room temperature for 15 minutes, diluted with water and then extracted three times with ethyl acetate. The combined organic layers were washed with saturated aqueous sodium chloride and then dried over anhydrous magnesium sulfate. After the drying agent was filtered off, the filtrate was concentrated under reduced pressure and the resulting residue was purified by column chromatography (silica gel: Wako gel C200, developing solvent: hexane/ethyl acetate=10/1 to 3/2) to give (1R,2S,3R,5R,6R)-6-fluoro-2,3-dihydroxybicyclo[3.1.0]hexane-2,6-dicarboxylic acid 2-benzyl ester 6-ethyl ester (4.21 g).

$^1$H-NMR (300 MHz, CDCl$_3$) δ (ppm); 1.29(3H, t, J=7.2 Hz), 2.06–2.21(2H, m), 2.30(1H, dd, J=7.6, 2.6 Hz), 2.47 (1H, dd, J=7.6, 13.2 Hz), 2.50(1H, dd, J=1.2, 9.2 Hz), 4.02(1H, s), 4.24(2H, q, J=7.2 Hz), 4.34–4.46(1H, m), 5.23(1H, d, J=12.5 Hz), 5.28(1H, d, J=12.5 Hz), 7.27–7.42 (5H, m)

MS(ESI)(Pos)m/z; 361(M+Na)$^+$.

$[α]_D^{29}$=−45.8° (C=0.202%, chloroform)

(3) A solution of (1R,2S,3R,5R,6R)-6-fluoro-2,3-dihydroxybicyclo[3.1.0]hexane-2,6-dicarboxylic acid 2-benzyl ester 6-ethyl ester (3.96 g) in dichloromethane (20 mL) was cooled to 4° C. and thionyl chloride (1.70 mL) was added thereto, followed by stirring at 40° C. for 13 hours. After the solvent and excess reagents were distilled off under reduced pressure, the resulting residue was dissolved in carbon tetrachloride (12 mL), acetonitrile (12 mL) and water (20 mL). To this solution, sodium metaperiodate (3.76 g) and ruthenium trichloride hydrate (500 mg) were added and stirred at room temperature for 20 minutes. After addition of water, the reaction mixture was extracted three times with diethyl ether. The combined organic layers were washed with saturated aqueous sodium chloride and then dried over anhydrous magnesium sulfate. After the drying agent was filtered off, the filtrate was concentrated under reduced pressure and the resulting residue was purified by column chromatography (silica gel: Wako gel C200, developing solvent: hexane/ethyl acetate=5/1 to 2/1) to give (1R,1aR,1bS,4aR,5aR)-1-fluoro-3,3-dioxotetrahydro-2,4-dioxa-3λ$^6$-thiacyclopropa[a]pentalene-1,1b-dicarboxylic acid 1b-benzyl ester 1-ethyl ester (4.11 g).

$^1$H-NMR (300 MHz, CDCl$_3$) δ (ppm); 1.29(3H, t, J=7.2 Hz), 2.53–2.61(1H, m), 2.72(1H, ddd, J=0.9, 7.6, 15.2 Hz), 2.78–2.89 (1H, m), 2.83(1H, dd, J=2.3, 7.2 Hz), 4.19–4.31 (2H, m), 5.26(1H, d, J=12.1 Hz), 5.33(1H, d, J=12.1 Hz), 5.45(1H, dt, J=3.8, 7.6 Hz), 7.28–7.43(5H,m)

MS(ESI)(Pos)m/z; 423(M+Na)$^+$ $[α]_D^{30}$=+31.3° (C=0.203%, chloroform)

(4) Sodium azide (1.09 g) was added to (1R,1aR,1bS,4aR,5aR)-1-fluoro-3,3-dioxotetrahydro-2,4-dioxa-3λ$^6$-thiacyclopropa[a]pentalene-1,1b-dicarboxylic acid 1b-benzyl ester 1-ethyl ester (3.73 g) dissolved in N,N-dimethylformamide (37 mL) and water (3.7 mL), followed by stirring at 50° C. for 14 hours. After the solvent was distilled off under reduced pressure, the resulting residue was dissolved in diethyl ether (187 mL) and water (5.2 mL). To this solution, 20% sulfuric acid (15 mL) was added and stirred at room temperature for 8 hours. After addition of water, the reaction mixture was extracted three times with diethyl ether. The combined organic layers were washed with saturated aqueous sodium chloride and then dried over anhydrous magnesium sulfate. After the drying agent was filtered off, the filtrate was concentrated under reduced pressure and the resulting residue was purified by column chromatography (silica gel: Wako gel C200, developing solvent: hexane/ethyl acetate=5/1 to 1/1) to give (1R,2R,3R,5R,6R)-2-azide-3-hydroxy-6-fluorobicyclo[3.1.0]hexane-2,6-dicarboxylic acid 2-benzyl ester 6-ethyl ester (3.02 g).

$^1$H-NMR (300 MHz, CDCl$_3$) δ (ppm); 1.32(3H, t, J=7.2 Hz), 2.18–2.54(5H, m), 4.22–4.36(1H, m), 4.26(2H, q, J=7.2 Hz), 5.27(1H, d, J=12.2 Hz), 5.35(1H, d, J=12.2 Hz), 7.31–7.45(5H, m)

MS(ESI)(Pos)m/z; 386(M+Na)$^+$ $[α]D^{30}$=−50.2° (C=0.212%, chloroform)

EXAMPLE 1

Synthesis of (1R,2R,3R,5R,6R)-2-amino-3-methoxy-6-fluorobicyclo[3.1.0]hexane-2,6-dicarboxylic acid (1) (1R,2R,3R,5R,6R)-2-Azide-3-hydroxy-6-fluorobicyclo[3.1.0]hexane-2,6-dicarboxylic acid 2-benzyl ester 6-ethyl ester (500 mg) was dissolved in dichloromethane (0.5 mL). To this solution, 2,6-di-t-butylpyridine (158 mg) and methyl trifluoromethanesulfonate (113 mg) were added and stirred at room temperature for 4 days. The reaction mixture was poured into 1N hydrochloric acid and extracted three times with diethyl ether. The combined organic layers were washed with saturated aqueous sodium chloride and then dried over anhydrous magnesium sulfate. After the drying agent was filtered off, the filtrate was concentrated under reduced pressure and the resulting residue was purified by column chromatography (silica gel: Wako gel C200, developing solvent: hexane/ethyl acetate=9/1) to give (1R,2R,3R,5R,6R)-2-azide-3-methoxy-6-fluorobicyclo[3.1.0]hexane-2,6-dicarboxylic acid 2-benzyl ester 6-ethyl ester (42.0 mg).

$^1$H-NMR (300 MHz, CDCl$_3$) δ (ppm); 1.32(3H, t, J=7.2 Hz), 2.20–2.50(4H, m), 3.32(3H, s), 3.78–3.86(1H, m), 4.26(2H, q, J=7.2 Hz), 5.26(1H, d, J=12.3 Hz), 5.34(1H, d, J=12.3 Hz), 7.30–7.42(5H, m)

MS(ESI)(Pos)m/z; 400(M+Na)$^+$ (2) (1R,2R,3R,5R,6R)-2-Azide-3-methoxy-6-fluorobicyclo[3.1.0]hexane-2,6-dicarboxylic acid 2-benzyl ester 6-ethyl ester (280 mg) was dissolved in acetic acid (4 mL) and water (1 mL). To this solution, 10% palladium/carbon (28 mg) was added and stirred under a hydrogen atmosphere at room temperature for 18 hours. After the catalyst was filtered off, the filtrate was concentrated under reduced pressure. The resulting residue was then dissolved in 10% hydrochloric acid (8 mL) and heated at reflux for 1.5 hours. After the solvent was distilled off under reduced pressure, the resulting residue was purified on an ion-exchange resin (AG 50W-X8 Resin (H-type), developing solvent: water, 50% aqueous tetrahydrofuran, 10% aqueous pyridine) to give (1R,2R,3R,5R,6R)-2-amino-3-methoxy-6-fluorobicyclo[3.1.0]hexane-2,6-dicarboxylic acid (117 mg).

EXAMPLE 2

Synthesis of (1R,2R,3R,5R,6R)-2-amino-3-(4-fluorobenzyloxy)-6-fluorobicyclo[3.1.0]hexane-2,6-dicarboxylic acid 2-benzyl ester 6-ethyl ester and (1R,2R,3R,5R,6R)-2-amino-3-(4-fluorobenzyloxy)-6-fluorobicyclo[3.1.0]hexane-2,6-dicarboxylic acid (1) Sodium hydride (79.0 mg, 60% in oil) was washed twice with hexane and suspended in diethyl ether (1.9 mL), followed by dropwise addition of 4-fluorobenzyl alcohol (2.50 g) dissolved in diethyl ether (2.9 mL). After stirring at room temperature for 20 minutes, trichloroacetonitrile (2.70 g) was added dropwise while cooling on salt/ice. Stirring was continued at this temperature for 15 minutes, on ice for 15 minutes, on a water bath for 20 minutes, and then at room temperature for 20 minutes. After the reaction solution was concentrated under reduced pressure, pentane (1.9 mL) and methanol (75 μL) were added to the resulting residue and stirred vigorously at room temperature for 15 minutes. After inorganic salts were filtered off, the filtrate was concentrated under reduced pressure to give crude 4-fluorobenzyl-2,2,2-trichloroacetimidate (5.28 g).

The crude 4-fluorobenzyl-2,2,2-trichloroacetimidate (3.40 g) and (1R,2R,3R,5R,6R)-2-azide-3-hydroxy-6-fluorobicyclo[3.1.0]hexane-2,6-dicarboxylic acid 2-benzyl ester 6-ethyl ester (3.04 g) were dissolved in dichloromethane (9.2 mL) and cyclohexane (18.4 mL). This solution was cooled on an ice bath, followed by addition of trifluoromethanesulfonic acid (110 μL). After stirring at room temperature for 16 hours, inorganic salts were filtered off and saturated aqueous sodium bicarbonate was added while cooling on ice. After the reaction mixture was extracted twice with chloroform, the combined organic layers were washed with saturated aqueous sodium chloride and dried over anhydrous sodium sulfate. After the drying agent was filtered off, the filtrate was concentrated under reduced pressure and the resulting residue was purified by column chromatography (silica gel: Wako gel C200, developing solvent: hexane/ethyl acetate=10/1 to 5/1) to give (1R,2R,3R,5R,6R)-2-azide-3-(4-fluorobenzyloxy)-6-fluorobicyclo[3.1.0]hexane-2,6-dicarboxylic acid 2-benzyl ester 6-ethyl ester (1.94 g).

$^1$H-NMR (200 MHz, CDCl$_3$) δ (ppm); 1.32(3H, t, J=7.0 Hz), 2.20–2.42(4H, m), 3.96–4.06(1H, m), 4.27(2H, q, J=7.0 Hz), 4.40(1H, d, J=11.5 Hz), 4.59(1H, d, J=11.5 Hz), 5.20 (1H, d, J=12.1 Hz), 5.34(1H, d, J=12.1 Hz), 6.92–7.37(9H, m)

MS(ESI)(Pos)m/z; 494(M+Na)$^+$ (2) (1R,2R,3R,5R,6R)-2-Azide-3-(4-fluorobenzyloxy)-6-fluorobicyclo[3.1.0]hexane-2,6-dicarboxylic acid 2-benzyl ester 6-ethyl ester (521 mg) was dissolved in tetrahydrofuran (16 mL) and water (1.6 mL). To this solution, a solution of 1M trimethylphosphine in tetrahydrofuran (1.20 mL) was added and stirred at room temperature for 18 hours. The reaction mixture was diluted with diethyl ether, washed with saturated aqueous sodium bicarbonate and saturated aqueous sodium chloride, and then dried over anhydrous sodium sulfate. After the drying agent was filtered off, the filtrate was concentrated under reduced pressure and the resulting residue was purified by column chromatography (silica gel: Wako gel C200, developing solvent: hexane/ethyl acetate=2/1) to give (1R,2R,3R,5R,6R)-2-amino-3-(4-fluorobenzyloxy)-6-fluorobicyclo[3.1.0]hexane-2,6-dicarboxylic acid 2-benzyl ester 6-ethyl ester (338 mg).

(3) Lithium hydroxide hydrate (72.0 mg) was added to (1R,2R,3R, 5R,6R)-2-amino-3-(4-fluorobenzyloxy)-6-fluorobicyclo[3.1.0]hexane-2,6-dicarboxylic acid 2-benzyl ester 6-ethyl ester (304 mg) dissolved in tetrahydrofuran (6 mL) and water (3 mL), followed by stirring at room temperature for 31 hours. After the solvent was distilled off under reduced pressure, the resulting residue was purified on an ion-exchange resin (AG 50W-X8 Resin (H-type), developing solvent: water, 50% aqueous tetrahydrofuran, 10% aqueous pyridine) to give (1R,2R, 3R,5R,6R)-2-amino-3-(4-fluorobenzyloxy)-6-fluorobicyclo[3.1.0]hexane-2,6-dicarboxylic acid (195 mg).

EXAMPLE 3

Synthesis of (1R,2R,3R,5R,6R)-2-amino-3-((R*)-1-(naphthalen-2-yl)ethoxy)-6-fluorobicyclo[3.1.0]hexane-2,6-dicarboxylic acid 2-benzyl ester 6-ethyl ester, (1R,2R,3R,5R,6R)-9-amino-3-((S*)-1-(naphthalen-2-yl)ethoxy)-6-fluorobicyclo[3.1.0]hexane-2,6-dicarboxylic acid 2-benzyl ester 6-ethyl ester, (1R,2R,3R,5R,6R)-2-amino-3-((R*)-1-(naphthalen-2-yl)ethoxy)-6-fluorobicyclo[3.1.0]hexane-2,6-dicarboxylic acid and (1R,2R,3R,5R,6R)-2-amino-3-((S*)-1-(naphthalen-2-yl)ethoxy)-6-fluorobicyclo[3.1.0]hexane-2,6-dicarboxylic acid (1) Sodium hydride (23.0 mg, 60% in oil) was washed twice with hexane and suspended in tetrahydrofuran (0.8 mL), followed by dropwise addition of 1-(naphthalen-2-yl)ethanol (1.00 g) dissolved in tetrahydrofuran (1.2 mL). After stirring at room temperature for 20 minutes, trichloroacetonitrile (0.58 mL) was added dropwise while cooling on salt/ice. Stirring was continued at this temperature for 20 minutes, on ice for 20 minutes, on a water bath for 30 minutes, and then at room temperature for 50 minutes. After the reaction solution was concentrated under reduced pressure, pentane (5 mL), methanol (19 μL) and tetrahydrofuran (0.5 mL) were added to the resulting residue and stirred vigorously at room temperature for 10 minutes. After inorganic salts were filtered off, the filtrate was concentrated under reduced pressure to give crude 1-(naphthalen-2-yl)ethyl-2,2,2-trichloroacetimidate (1.84 g).

The crude 1-(naphthalen-2-yl)ethyl-2,2,2-trichloroacetimidate (590 mg) and (1R,2R,3R,5R,6R)-2-azide-3-hydroxy-6-fluorobicyclo[3.1.0]hexane-2,6-dicarboxylic acid 2-benzyl ester 6-ethyl ester (450 mg) were dissolved in dichloromethane (1.5 mL) and cyclohexane (3.0 mL), followed by addition of trifluoromethanesulfonic acid (17 μL). After stirring at room temperature for 1 hour, inorganic salts were filtered off and saturated aqueous sodium bicarbonate was added while cooling on ice. After the reaction mixture was extracted twice with chloroform, the combined organic layers were washed with saturated aqueous sodium chloride and dried over anhydrous sodium sulfate. After the drying agent was filtered off, the filtrate was concentrated under reduced pressure and the resulting residue was purified by column chromatography (silica gel: Wako gel C200, developing solvent: hexane/ethyl acetate=13/1 to 5/1) and (silica gel: M.S. GEL SIL D-75-60A (Dokai Chemical Industries Co., Ltd.), developing solvent: hexane/ethyl acetate=13/1) to give (1R,2R,3R,5R,6R)-2-azide-3-((R*)-1-(naphthalen-2-yl)-ethoxy)-6-fluorobicyclo[3.1.0]hexane-2,6-dicarboxylic acid 2-benzyl ester 6-ethyl ester (271 mg, Rf value: 0.55, developing solvent: hexane/ethyl acetate=3/1, TLC: silica gel 60$F_{254}$) and (1R,2R,3R,5R,6R)-2-azide-3-((S*)-1-(naphthalen-2-yl)ethoxy)-6-fluorobicyclo[3.1.0]hexane-2, 6-dicarboxylic acid 2-benzyl ester 6-ethyl ester (301 mg, Rf value: 0.49, developing solvent: hexane/ethyl acetate=3/1, TLC: silica gel 60$F_{254}$).

(1R,2R,3R,5R,6R)-2-Azide-3-((R*) -1-(naphthalen-2-yl)ethoxy)-6-fluorobicyclo[3.1.0]hexane-2,6-dicarboxylic acid 2-benzyl ester 6-ethyl ester $^1$H-NMR (200 MHz, CDCl$_3$) δ (ppm); 1.26(3H, t, J=7.3 Hz), 1.35(3H, d, J=6.6 Hz), 1.92–2.37(4H, m), 3.85–3.95 (1H, m), 4.20(2H, q, J=7.3 Hz), 4.77(1H, q, J=6.6 Hz), 5.27(1H, d, J=12.2 Hz), 5.47(1H, d, J=12.2 Hz), 7.31–7.85 (12H, m)

MS(ESI)(Pos)m/s; 540(M+Na)$^+$.

(1R,2R,3R,5R,6R)-2-Azide-3-((S*)-1-(naphthalen-2-yl)ethoxy)-6-fluorobicyclo[3.1.0]hexane-2,6-dicarboxylic acid 2-benzyl ester 6-ethyl ester:

$^1$H-NMR (200 MHz, CDCl$_3$) δ (ppm); 1.27(3H, t, J=7.3 Hz), 1.40(3H, d, J=6.4 Hz), 2.24–2.49(4H, m), 3.91–4.01 (1H, m), 4.22(2H, q, J=7.3 Hz), 4.61(1H, q, J=6.4 Hz), 5.12(1H, d, J=12.3 Hz), 5.32(1H, d, J=12.3 Hz), 7.31–7.83 (12H, m)

MS(ESI)(Pos)m/s; 540(M+Na)$^+$ (2) Starting with (1R,2R,3R,5R,6R)-2-azide-3-((R*)-1-(naphthalen-2-yl)ethoxy)-6-fluorobicyclo[3.1.0]hexane-2,6-dicarboxylic acid 2-benzyl ester 6-ethyl ester (266 mg) and (1R,2R,3R,5R,6R)-2-azide-3-((S*)-1-(naphthalen-2-yl)ethoxy)-6-fluorobicyclo[3.1.0]hexane-2,6-dicarboxylic acid 2-benzyl ester 6-ethyl ester (238 mg), the same procedure as shown in Example 2(2) was repeated to give (1R,2R,3R,5R,6R)-2-amino-3-( (R*)-1-(naphthalen-2-yl)ethoxy)-6-fluorobicyclo[3.1.0]hexane-2,6-dicarboxylic acid 2-benzyl ester 6-ethyl ester (164 mg) and (1R,2R,3R,5R,6R)-2-amino-3-((S*)-1-(naphthalen-2-yl) ethoxy)-6-fluorobicyclo[3.1.0]hexane-2,6-dicarboxylic acid 2-benzyl ester 6-ethyl ester (153 mg), respectively.

(3) Starting with (1R,2R,3R,5R,6R)-2-amino-3-((R*)-1-(naphthalen-2-yl)ethoxy)-6-fluorobicyclo[3.1.0]hexane-2,6-dicarboxylic acid 2-benzyl ester 6-ethyl ester (158 mg) and (1R,2R,3R,5,R6R)-2-amino-3-((S*)-1-(naphthalen-2-yl)ethoxy)-6-fluorobicyclo[3.1.0]hexane-2,6-dicarboxylic acid 2-benzyl ester 6-ethyl ester (148 mg), the same procedure as shown in Example 2(3) was repeated to give (1R,2R,3R,5R,6R)-2-amino-3-((R*)-1-(naphthalen-2-yl)ethoxy)-6-fluorobicyclo[3.1.0]hexane-2,6-dicarboxylic acid (96.0 mg) and (1R,2R,3R,5R,6R)-2-amino-3-((S*)-1-(naphthalen-2-yl)ethoxy)-6-fluorobicyclo[3.1.0]hexane-2,6-dicarboxylic acid (72.0 mg).

EXAMPLE 4

Synthesis of (1R,2R,3R,5R,6R)-2-amino-3-propyloxy-6-fluorobicyclo[3.1.0]hexane-2,6-dicarboxylic acid (1) (1R,2R,3R,5R,6R)-2-Amino-3-(2-propenyloxy)-6-fluorobicyclo[3.1.0]hexane-2,6-dicarboxylic acid (40 mg) was dissolved in water (1 mL). To this solution, 10% palladium/carbon (4 mg) was added and stirred under a hydrogen atmosphere at room temperature for 2 days. After the catalyst was filtered off, the filtrate was concentrated under reduced pressure, followed by addition of tetrahydrofuran (1 mL) and heating at reflux for 1 hour. The reaction mixture was stirred at room temperature for an additional 3 hours, filtered to remove any solids, and then purified on an ion-exchange resin (AG 50W-X8 Resin (H-type), developing solvent: water, 50% aqueous tetrahydrofuran, 10% aqueous pyridine) to give (1R,2R,3R,5R,6R)-2-amino-3-propyloxy-6-fluorobicyclo[3.1.0] hexane-2,6-dicarboxylic acid (30 mg).

EXAMPLE 5

Synthesis of (1R,2R,3R,5R,6R)-2-amino-3-cyclopentyloxy-6-fluorobicyclo[3.1.0]hexane-2,6-dicarboxylic acid (1) Starting with crude 2-cyclopentenyl-2,2,2-trichloroacetimidate (375 mg) prepared from 2-cyclopenten-1-ol and (1R,2R,3R,5R,6R)-2-azide-3-hydroxy-6-fluorobicyclo [3.1.0]hexane-2,6-dicarboxylic acid 2-benzyl ester 6-ethyl ester (650 mg), the same procedure as shown in Example 2(1) was repeated to give (1R,2R,3R,5R,6R)-2-azide-3-(2-cyclopentenyloxy)-6-fluorobicyclo[3.1.0]hexane-2,6-dicarboxylic acid 2-benzyl ester 6-ethyl ester (339 mg).

$^1$H-NMR (200 MHz, CDCl$_3$) δ (ppm); 1.32 (3 H, t, J=7.3 Hz), 1.90–2.52 (8 H, m), 3.94–4.14 (1 H, m), 4.27 (2 H, q, J=7.3 Hz), 4.52–4.79 (1 H, m), 5.15–5.41 (2 H, m), 5.58–5.82 (1 H, m), 5.88–6.04 (1 H, m), 7.30–7.46 (5 H, m).

MS(ESI)(Pos)m/z; 452 (M+Na)$^+$ (2) (1R,2R,3R,5R,6R)-2-Azide-3-(2-cyclopentenyloxy)-6-fluorobicyclo[3.1.0]hexane-2,6-dicarboxylic acid 2-benzyl ester 6-ethyl ester (331 mg) was dissolved in acetic acid (18 mL) and water (6 mL). To this solution, 10% palladium/carbon (39 mg) was added and stirred under a hydrogen atmosphere at room temperature for 24 hours. After the catalyst was filtered off, the filtrate was concentrated under reduced pressure. The resulting residue was dissolved in tetrahydrofuran (7.36 mL) and water (3.53 mL), followed by addition of lithium hydroxide hydrate (80 mg) and stirring at room temperature for 4 hours.

After the solvent was distilled off under reduced pressure, the resulting residue was purified on an ion-exchange resin (AG 50W-X8 Resin (H-type), developing solvent: water, 50% aqueous tetrahydrofuran, 10% aqueous pyridine) to give (1R,2R,3R,5R,6R)-2-amino-3-cyclopentyloxy-6-fluorobicyclo[3.1.0]hexane-2,6-dicarboxylic acid (61 mg).

EXAMPLE 6

Synthesis of (1R,2R,3R,5R,6R)-2-amino-3-(3-nitrobenzyloxy)-6-fluorobicyclo[3.1.0]hexane-2,6-dicarboxylic acid diethyl ester, (1R,2R,3R,5R,6R)-2-amino-3-(3-aminobenzyloxy)-6-fluorobicyclo[3.1.0]hexane-2,6-dicarboxylic acid diethyl ester and (1R,2R,3R,5R,6R)-2-amino-3-(3-aminobenzyloxy)-6-fluorobicyclo[3.1.0]hexane-2,6-dicarboxylic acid (1) Starting with crude 3-nitrobenzyl-2,2,2-trichloroacetimidate (562 mg) prepared from 3-nitrobenzyl alcohol and (1R,2R,3R,5R,6R)-2-azide-3-hydroxy-6-fluorobicyclo[3.1.0]hexane-2,6-dicarboxylic acid diethyl ester (380 mg), the same procedure as shown in Example 2(1) was repeated to give (1R,2R,3R,5R,6R)-2-azide-3-(3-nitrobenzyloxy)-6-fluorobicyclo[3.1.0]hexane-2,6-dicarboxylic acid diethyl ester (279 mg).

$^1$H-NMR (200 MHz, CDCl$_3$) δ (ppm); 1.32 (3 H, t, J=7.2 Hz), 1.34 (3 H, t, J=7.2 Hz), 2.22–2.42 (2 H, m), 2.50 (2 H, dd, J=2.7, 7.8 Hz), 3.94–4.10 (1 H, m), 4.20–4.46 (4 H, m), 4.58 (1 H, d, J=12.1 Hz), 4.80 (1 H, d, J=12.1 Hz) 7.44–7.66 (2 H, m), 8.03–8.24 (2 H, m).

MS(ESI)(Pos)m/z; 459 (M+Na)$^+$ (2) Starting with (1R,2R,3R,5R,6R)-2-azide-3-(3-nitrobenzyloxy)-6-fluorobicyclo[3.1.0]hexane-2,6-dicarboxylic acid diethyl ester (275 mg), the same procedure as shown in Example 2(2) was repeated to give (1R,2R,3R,5R,6R)-2-amino-3-(3-nitrobenzyloxy)-6-fluorobicyclo[3.1.0]hexane-2,6-dicarboxylic acid diethyl ester (120 mg).

(3) (1R,2R,3R,5R,6R)-2-Amino-3-(3-nitrobenzyloxy)-6-fluorobicyclo[3.1.0]hexane-2,6-dicarboxylic acid diethyl ester (120 mg) was dissolved in acetic acid (0.21 mL). To this solution, zinc powder (101 mg) was added and stirred at room temperature for 3 hours. The reaction mixture was filtered to remove any solids, followed by addition of ice-cold saturated sodium bicarbonate. After the reaction mixture was extracted twice with ethyl acetate, the combined organic layers were washed with 0.5 M aqueous sodium carbonate and saturated aqueous sodium chloride, and then dried over anhydrous sodium sulfate. After the drying agent was filtered off, the filtrate was concentrated under reduced pressure and the resulting residue was purified by column chromatography (silica gel: Wako gel C200, developing solvent: chloroform/ethanol=30/1) to give (1R,2R,3R,5R,6R)-2-amino-3-(3-aminobenzyloxy)-6-fluorobicyclo[3.1.0]hexane-2,6-dicarboxylic acid diethyl ester (96 mg).

(4) Starting with (1R,2R,3R,5R,6R)-2-amino-3-(3-aminobenzyloxy)-6-fluorobicyclo[3.1.0]hexane-2,6-dicarboxylic acid diethyl ester (90 mg), the same procedure as shown in Example 2(3) was repeated to give (1R,2R,3R,5R,6R)-2-amino-3-(3-aminobenzyloxy)-6-fluorobicyclo[3.1.0]hexane-2,6-dicarboxylic acid (60 mg).

EXAMPLE 7

Synthesis of (1R,2R,3S,5R,6R)-2-azide-3-hydroxy-6-fluorobicyclo[3.1.0]hexane-2,6-dicarboxylic acid 2,6-diethyl ester (1) (1R,2R,3R,5R,6R)-2-Azide-3-hydroxy-6-fluorobicyclo[3.1.0]hexane-2,6-dicarboxylic acid 2,6-diethyl ester (120 mg) was dissolved in dichloromethane (20 mL). To this solution, trifluoromethanesulfonic anhydride (78 μL) in dichloromethane (0.4 mL) was added dropwise at –75° C. under a nitrogen atmosphere and stirred on ice for 1.5 hours. Pyridine (48 μL) and trifluoromethanesulfonic anhydride (39 μL) in dichloromethane (0.2 mL) were added dropwise at –75° C., followed by stirring on ice for 25 minutes. After addition of ether (10 mL), the reaction mixture was filtered to remove any solids. The filtrate was concentrated under reduced pressure and the resulting residue was purified by column chromatography (silica gel: Wako gel C200, developing solvent: hexane/ethyl acetate=5/1) to give (1R,2R,3R,5R,6R)-2-azide-3-trifluoromethanesulfonyloxy-6-fluorobicyclo[3.1.0]hexane-2,6-dicarboxylic acid 2,6-diethyl ester (166 mg).

$^1$H-NMR (200 MHz, CDCl$_3$) δ (ppm); 1.35 (3 H, t, J=7.0 Hz), 1.38 (3 H, t, J=7.0 Hz), 2.35–2.50 (2 H, m), 2.62–2.86 (2 H, m), 4.31 (2 H, q, J=7.0 Hz), 4.27–4.55 (2 H, m), 4.94–5.10 (1 H, m)

MS(FAB) (Pos)m/z; 434 (M+H)$^+$ $[α]_D^{26}$=–31.2° (C=0.43%, chloroform)

(2) (1R,2R,3R,5R,6R)-2-Azide-3-trifluoromethanesulfonyloxy-6-fluorobicyclo[3.1.0]hexane-2,6-dicarboxylic acid 2,6-diethyl ester (701 mg) was dissolved in N,N-dimethylformamide (6.9 mL). To this solution, potassium nitrite (688 mg) and 18-crown-6 (428 mg) were added and stirred under a nitrogen atmosphere at room temperature for 1.5 days and then at 45° C. for 3.5 days. After addition of water, the reaction mixture was extracted twice with ethyl acetate. The combined organic layers were washed with saturated aqueous sodium chloride and then dried over anhydrous sodium sulfate. After the drying agent was filtered off, the filtrate was concentrated under reduced pressure and the resulting residue was purified by column chromatography (silica gel: Wako gel C200, developing solvent: hexane/ethyl acetate=5/1) to give (1R,2R,3S,5R,6R)-2-azide-3-hydroxy-6-fluorobicyclo[3.1.0]hexane-2,6-dicarboxylic acid 2,6-diethyl ester (388 mg).

$^1$H-NMR (200 MHz, CDCl$_3$) δ (ppm); 1.34 (3 H, t, J=7.0 Hz), 1.36 (3 H, t, J=7.0 Hz), 2.16 (1 H, dd, J=2.9 Hz, 14.9 Hz), 2.17–2.30 (1 H, m), 2.44 (1 H, dd, J=3.1 Hz, 8.1 Hz), 2.61 Hz (1 H, dd, J=12.3 Hz, 16.0 Hz), 2.80–2.99 (1 H, m), 4.29 (2 H, q, J=7.0 Hz), 4.34 (2 H, q, J=7.0 Hz), 4.48–4.64 (1 H, m)

MS(ESI)(Pos)m/z; 324 (M+Na)$^+$ $[α]_D^{25}$=+6.4° (C=0.96%, chloroform)

EXAMPLE 8

Synthesis of (1R,2R,3R,5R,6R)-2-amino-3-(3,4-dichlorobenzyloxy)-6-fluorobicyclo[3.1.0]hexane-2,6-dicarboxylic acid 2,6-diethyl ester and (1R,2R,3R,5R,6R)-2-amino-3-(3,4-dichlorobenzyloxy)-6-fluorobicyclo[3.1.0]hexane-2,6-dicarboxylic acid 2-ethyl ester (1) Starting with crude 3,4-dichlorobenzyl-2,2,2-trichloroacetimidate (3.17 g) prepared from 3,4-dichlorobenzyl alcohol and (1R,2R,3R,5R,6R)-2-azide-3-hydroxy-6-fluorobicyclo[3.1.0]hexane-2,6-dicarboxylic acid diethyl ester (1.98 g), the same procedure as shown in Example 2(1) was repeated to give (1R,2R,3R,5R,6R)-2-azide-3-(3,4-dichlorobenzyloxy)-6-fluorobicyclo[3.1.0]hexane-2,6-dicarboxylic acid diethyl ester (1.16 g).

$^1$H-NMR (200 MHz, CDCl$_3$) δ (ppm); 1.31 (3 H, t, J=7.3 Hz), 1.33 (3H, t, J=7.3 Hz), 2.22–2.52 (4 H, m), 3.91–4.05 (1 H, m), 4.29 (2 H, q, J=7.3 Hz), 4.18–4.44 (2 H, m), 4.42 (1 H, d, J=11.9 Hz), 4.64 (1 H, d, J=11.9 Hz), 7.06–7.14 (1 H, m), 7.34–7.50 (2 H, m).

MS(ESI)(Pos)m/z; 482 (M+Na)$^+$ $[α]_D^{28}$=−12.6° (C=1.14%, chloroform)

(2) Starting with (1R,2R,3R,5R,6R)-2-azide-3-(3,4-dichlorobenzyloxy)-6-fluorobicyclo[3.1.0]hexane-2,6-dicarboxylic acid diethyl ester (1.11 g), the same procedure as shown in Example 2(2) was repeated to give (1R,2R,3R,5R,6R)-2-amino-3-(3,4-dichlorobenzyloxy)-6-fluorobicyclo[3.1.0]hexane-2,6-dicarboxylic acid diethyl ester (878 mg).

(3) (1R,2R,3R,5R,6R)-2-Amino-3-(3,4-dichlorobenzyloxy)-6-fluorobicyclo[3.1.0]hexane-2,6-carboxylic acid 2-ethyl ester (150 mg) was dissolved in tetrahydrofuran (3.5 mL) and water (1.7 mL). To this solution, lithium hydroxide hydrate (17.8 mg) was added and stirred on ice for 2 hours. After addition of 1N hydrochloric acid (0.45 mL), the reaction mixture was diluted with water to a total volume of 50 mL and purified on an ion-exchange resin (AG 50W-X8 Resin (H-type), developing solvent: water, 50% aqueous tetrahydrofuran, 10% aqueous pyridine) to give (1R,2R,3R,5R,6R)-2-amino-3-(3,4-dichlorobenzyloxy)-6-fluorobicyclo[3.1.0]hexane-2,6-carboxylic acid 2-ethyl ester (107 mg).

EXAMPLE 9

Synthesis of (1R,2R,3R,5R,6R)-2-amino-3-(3,4-dichlorobenzyloxy)-6-fluorobicyclo[3.1.0]hexane-2,6-carboxylic acid 6-ethyl ester hydrochloride (1) Starting with (1R,2R,3R,5R,6R)-2-amino-3-(3,4-dichlorobenzyloxy)-6-fluorobicyclo[3.1.0]hexane-2,6-dicarboxylic acid diethyl ester (304 mg), the same procedure as shown in Example 2(3) was repeated to give (1R,2R,3R,5R,6R)-2-amino-3-(3,4-dichlorobenzyloxy)-6-fluorobicyclo[3.1.0]hexane-2,6-dicarboxylic acid (195 mg).

(2) (1R,2R,3R,5R,6R)-2-Amino-3-(3,4-dichlorobenzyloxy)-6-fluorobicyclo[3.1.0]hexane-2,6-dicarboxylic acid (114 mg) was dissolved in ethanol (1.1 mL). To this solution, thionyl chloride (88 μL) was added at room temperature under a nitrogen atmosphere and then stirred at 50° C. for 1 hour. After the reaction mixture was filtered to remove any solids, the filtrate was concentrated under reduced pressure. Isopropyl ether (1.38 mL) was added to the resulting residue, which was then stirred at room temperature for 17 hours and filtered to collect solids. The solids were washed with isopropyl ether to give (1R,2R,3R,5R,6R)-2-amino-3-(3,4-dichlorobenzyloxy)-6-fluorobicyclo[3.1.0]hexane-2,6-dicarboxylic acid 6-ethyl ester hydrochloride (114 mg).

EXAMPLE 10

Synthesis of (1R,2R,3R,5R,6R)-2-[(2'S)-(2'-aminopropionyl)amino]-3-(3,4-dichlorobenzyloxy)-6-fluorobicyclo[3.1.0]hexane-2,6-dicarboxylic acid hydrochloride (1) N-t-Butoxycarbonyl-L-alanine (316 mg) was dissolved in dichloromethane (6.9 mL). To this solution, N-methylmorpholine (184 μL) and isobutyl chloroformate (218 μL) were added at −14° C. under a nitrogen atmosphere and stirred for 1 minute. (1R,2R,3R,5R,6R)-2-Amino-3-(3,4-dichlorobenzyloxy)-6-fluorobicyclo[3.1.0]hexane-2,6-dicarboxylic acid diethyl ester (691 mg) was dissolved in dichloromethane (6.9 mL) and added dropwise to the reaction mixture, followed by stirring at room temperature for 30 minutes. The reaction solution was washed twice with 1N hydrochloric acid and dried over anhydrous sodium sulfate. After the drying agent was filtered off, the filtrate was concentrated under reduced pressure and the resulting residue was purified by column chromatography (silica gel: Wako gel C200, developing solvent: hexane/ethyl acetate=2/1) to give (1R,2R,3R,5R,6R)-2-[(2'S)-(2'-t-butoxycarbonylaminopropionyl)amino]-3-(3,4-dichlorobenzyloxy)-6-fluorobicyclo[3.1.0]hexane-2,6-dicarboxylic acid diethyl ester (902 mg).

$^1$H-NMR (200 MHz, CDCl$_3$) δ (ppm); 1.25 (3 H, t, J=7.1 Hz), 1.28 (3 H, t, J=7.1 Hz), 1.34 (3 H, d, J=7.0 Hz), 1.39 (9 H, s), 2.18–2.31 (1 H, m), 2.32–2.54 (2 H, m), 3.08 (1 H, dd, J=2.9 Hz, 7.9 Hz), 3.86–4.04 (1 H, m), 4.06–4.16 (5 H, m), 4.42 (1 H, d, J=11.6 Hz), 4.65 (1 H, d, J=11.6 Hz), 4.76–4.96 (1 H, m), 7.06–7.24 (1 H, m), 7.12 (1 H, dd, J=2.0 Hz, 8.1 Hz), 7.39 (1 H, d, J=2.0 Hz), 7.40 (1 H, d, J=8.1 Hz)

MS(ESI)(Nega)m/z; 630 (M−H)$^−$ $[α]_D^{24}$=−33.6° (C=0.42%, chloroform)

(2) (1R,2R,3R,5R,6R)-2-[(2'S)-(2'-t-Butoxycarbonylaminopropionyl)amino]-3-(3,4-dichlorobenzyloxy)-6-fluorobicyclo[3.1.0]hexane-2,6-dicarboxylic acid diethyl ester (45.5 mg) was dissolved in tetrahydrofuran (6 mL). To this solution, 2.5 M aqueous lithium hydroxide (6 mL) was added and stirred at room temperature for 2 days. The reaction solution was extracted three times with ethyl acetate and the combined organic layers were dried over anhydrous sodium sulfate. After the drying agent was filtered off, the filtrate was concentrated under reduced pressure to give crude (1R,2R,3R,5R,6R)-2-[(2'S)-(2'-t-butoxycarbonylaminopropionyl)amino]-3-(3,4-chlorobenzyloxy)-6-fluorobicyclo[3.1.0]hexane-2,6-dicarboxylic acid 6-lithium-2-ethyl ester (470 mg).

The crude (1R,2R,3R,5R,6R)-2-[(2'S)-(2'-t-butyloxyaminopropionyl)amino]-3-(3,4-chlorobenzyloxy)-6-fluorobicyclo[3.1.0]hexane-2,6-dicarboxylic acid 6-lithium 2-ethyl ester (375 mg) was dissolved in water (7.5 mL). To this solution, lithium hydroxide hydrate (135 mg) was added at room temperature and then stirred at 45° C. for 8 days. The reaction solution was washed ten times with ethyl acetate, adjusted to pH 2 with 1N hydrochloric acid while cooling on ice, and then extracted three times with ethyl acetate. The combined organic layers were washed with saturated aqueous sodium chloride and dried over anhydrous sodium sulfate. After the drying agent was filtered off, the filtrate was concentrated under reduced pressure.

While cooling on ice, a solution of 4M hydrogen chloride in ethyl acetate (4.6 mL) was added to the resulting residue, followed by stirring at room temperature for 15 hours. The precipitated solids were collected by filtration and washed with ethyl acetate to give (1R,2R,3R,5R,6R)-2-[(2'S)-(2'- aminopropionyl)amino]-3-(3,4-dichlorobenzyloxy)-6-fluorobicyclo[3.1.0]hexane-2,6-dicarboxylic acid hydrochloride (138 mg).

EXAMPLE 11

Synthesis of (1R,2R,3R,5R,6R)-2-amino-3-(3,4-dichlorobenzyloxy)-6-[(1'S)-(1'-hydroxycarbonyl-3'-methylbutylcarbamoyl)]-6-fluorobicyclo[3.1.0]hexane-2-carboxylic acid (1) (1R,2R,3R,5R,6R)-2-Azide-3-(3,4-dichlorobenzyloxy)-6-fluorobicyclo[3.1.0]hexane-2,6-dicarboxylic acid diethyl ester (854 mg) and leucine ethyl ester hydrochloride (464 mg) were dissolved in N,N-dimethylformamide (8.5 mL). To this solution, N-methylmorpholine (261 μL) was added at room temperature, followed by addition of 1-hydroxybenzotriazole (378 mg) and 1-ethyl-3-(3-dimethylaminopropyl)carbodiimide (464 mg) while cooling on ice. Stirring was continued at room temperature for 12 hours. After addition of ethyl acetate, the reaction mixture was washed with 1N hydrochloric acid and saturated aqueous sodium chloride, and then dried over anhydrous sodium sulfate. After the drying agent was filtered off, the filtrate was concentrated under reduced pressure. The resulting residue was purified by column chromatography (silica gel: Wako gel C200, developing solvent: hexane/ethyl acetate=8/1to give (1R,2R,3R,5R6R)-2-azide-3-(3,4-dichlorobenzyloxy)-6-[(1'S)-(1'-ethoxycarbonyl-3'-methylbutylcarbamoyl)]-6-fluorobicyclo[3.1.0]hexane-2-carboxylic acid ethyl ester (998 mg).

$^1$H-NMR (200 MHz, CDCl$_3$) δ (ppm); 0.96 (6 H, d, J=5.5 Hz), 1.29 (3 H, t, J=7.0 Hz), 1.30 (3 H, t, J=7.0 Hz), 1.52–1.80 (3 H, m), 2.26–2.57 (4 H, m), 3.86–4.02 (1 H, m), 4.22 (2 H, q, J=7.0 Hz), 4.10–4.38 (2 H, m), 4.42 (1 H, d, J=12.2 Hz), 4.50–4.66 (1 H, m), 4.65 (1 H, d, J=12.2 Hz), 6.79 (1 H, d, J=8.1 Hz), 7.11 (1 H, dd, J=2.0 Hz, 8.1 Hz), 7.38 (1 H, d, J=2.0 Hz), 7.40 (1 H, d, J=8.1 Hz)

MS(ESI)(Nega)m/z; 571 (M–H)$^-$ $[α]_D^{28}$=–20.0° (C=0.39%, chloroform)

(2) Starting with (1R,2R,3R,5R,6R)-2-azide-3-(3,4-dichlorobenzyloxy)-6-[(1'S)-(1'-ethoxycarbonyl-3'-methylbutylcarbamoyl)]-6-fluorobicyclo[3.1.0]hexane-2-carboxylic acid ethyl ester (996 mg), the same procedure as shown in Example 2(2) was repeated to give (1R,2R,3R,5R,6R)-2-amino-3-(3,4-dichlorobenzyloxy)-6-[(1'S)-(1'-ethoxycarbonyl-3'-methylbutylcarbamoyl)]-6-fluorobicyclo[3.1.0]hexane-2-carboxylic acid ethyl ester.

$^1$H-NMR (200 MHz, CDCl$_3$) δ (ppm); 0.96 (6 H, d, J=5.9 Hz), 1.29 (6 H, t, J=7.1 Hz), 1.52–1.77 (3 H, m), 1.85 (2 H, s), 2.10–2.28 (2 H, m), 2.36–2.48 (2 H, m), 3.69–3.87 (1 H, m), 4.21 (2 H, q, J=7.1 Hz), 4.15–4.36 (2 H, m), 4.45 (1 H, d, J=12.1 Hz), 4.64 (1 H, d, J=12.1), 4.55–4.69 (1 H, m), 6.77 (1 H, dd, J=3.4, 8.0), 7.10 (1 H, dd, J=1.8 Hz, 8.4 Hz), 7.38 (1 H, d, J=1.8 Hz), 7.39 (1 H, d, J=8.4 Hz)

MS(ESI)(Nega)m/z; 545 (M–H)$^-$ $[α]_D^{22}$=+2.4° (C=0.65%, chloroform)

(3) Starting with (1R,2R,3R,5R,6R)-2-amino-3-(3,4-dichlorobenzyloxy)-6-[(1'S)-(1'-ethoxycarbonyl-3'-methylbutylcarbamoyl)]-6-fluorobicyclo[3.1.0]hexane-2-carboxylic acid ethyl ester (400 mg), the same procedure as shown in Example 2(3) was repeated to give (1R,2R,3R,5R,6R)-2-amino-3-(3,4-dichlorobenzyloxy)-6-[(1'S)-(1'-hydroxycarbonyl-3'-methylbutylcarbamoyl)]-6-fluorobicyclo[3.1.0]hexane-2-carboxylic acid (250 mg).

Table 1 below summarizes chemical structures and physical data of the compounds prepared in Examples 1, 2, 3, 4, 5, 6, 8, 9, 10 and 11 as well as compounds prepared in a similar manner.

TABLE 1

[Structure: bicyclic compound with F, COR¹, COR², NHR³, OR⁴/R⁵ substituents at position 3]

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 1 | OH | OH | H | H | H | R | [α]$_D^{24}$ = −58.0 (C = 0.43%) | >199 | ESI(Nega) 232(M − H)⁻ | 2.33–2.44(3H, m), 2.63(1H, dd, J=7.9, 13.1Hz), 3.36(3H, s), 3.96(1H, dd, J=7.1, 13.1Hz). | Ex. 1 |
| 2 | OH | OH | H | H | H | S | [α]$_D^{21}$ = −49.7 (C = 0.20%) | >171 | ESI(Nega) 232(M − H)⁻ | 2.04–2.15(1H, m), 2.27–2.38(1H, m), 2.39–2.47(1H, m), 2.76–2.93(1H, m), 3.35(3H, s), 4.28–4.38(1H, m). | Ex. 1 |
| 3 | OH | OH | H | Et | H | R | | >165 | ESI(Nega) 260(M − H)⁻ | 0.85(3H, t, J=7.5Hz), 1.43–1.64(2H, m), 2.22–2.30(2H, m), 2.34–2.47(1H, m), 2.58(1H, dd, J=7.8, 13.5Hz), 3.38–3.60(2H, m), 3.99–4.08(1H, m). | Ex. 4 |
| 4 | OH | OH | H | —CH₂CH₂CH₂CH₂— | | R | [α]$_D^{26}$ = −24.8 (C = 0.33%) | >170 | ESI(Nega) 286(M − H)⁻ | 1.38–1.84(8H, m), 2.22–2.30(2H, m), 2.32–2.44(1H, m), 2.54(1H, dd, J=8.0, 13.6Hz), | Ex. 5 |

TABLE 1-continued

![structure: bicyclic compound with F, COR¹, H, COR², NHR³ substituents and O-CHR⁴R⁵ group at position 3]

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 5 | OH | OH | H | —CH=CH₂ | H | R | [α]$_D^{29}$ = −34.1 (C = 1.01%) | >248 | ESI(Nega) 258(M − H)⁻ | 3.97–4.13(2H, m), 2.22–2.44(3H, m), 2.58(1H, dd, J=7.5, 13.6Hz), 4.01–4.10(3H, m), 5.24(1H, d, J=10.4Hz), 5.31(1H, d, J=17.3Hz), 5.81–5.98(1H, m). | Ex. 2 |
| 6 | OH | OH | H | phenyl | H | R | | >226 | ESI(Nega) 308(M − H)⁻ | 2.24–2.57(4H, m), 4.04–4.14(1H, m), 4.56(1H, d, J=11.5Hz), 4.62(1H, d, J=11.5Hz), 7.41(5H, s). | Ex. 2 |
| 7 | OH | OH | H | —(CH₂)₂-phenyl | H | R | [α]$_D^{26}$ = −43.4 (C = 0.14%) | >230 | ESI(Nega) 336(M − H)⁻ | 1.78–1.93(2H, m), 2.23–2.30(2H, m), 2.31–2.46(1H, m), 2.54(1H, dd, J=7.39, 13.4Hz), 2.61–2.72(1H, m), 3.40–3.61(2H, m), 3.94–4.05(1H, m), 7.22–7.43(5H, m). | Ex. 1 |
| 8 | OH | OH | H | 3-methylphenyl | H | R | [α]$_D^{29}$ = −21.3 (C = 0.47%) | >215 | ESI(Nega) 322(M − H)⁻ | 2.24–2.27(2H, m), 2.35(3H, s), 2.37–2.54(2H, m), 4.08(1H, dd, J=7.6, 12.7Hz), 4.52(1H, d, J=11.5Hz), 4.59(1H, d, J=11.5Hz), 7.20–7.36(4H, m). | Ex. 2 |

TABLE 1-continued

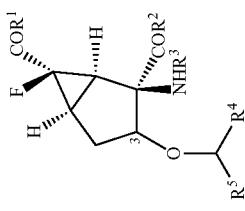

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 9 | OH | OH | H | 2-methylbiphenyl | H | R | $[\alpha]_D^{26} = -25.6$ (C = 0.16%) | >180 | ESI(Nega) 384(M − H)⁻ | 2.20–2.27(4H, m), 3.84–3.90(1H, m), 4.46(1H, d, J=11.0Hz), 4.55(1H, d, J=11.0Hz), 7.34–7.58(9H, m). | Ex. 2 |
| 10 | OH | OH | H | 3-methylbiphenyl | H | R | | >180 | ESI(Nega) 384(M − H)⁻ | 2.27–2.57(4H, m), 4.06–4.19(1H, m), 4.60–4.76(2H, m), 7.41–7.74(9H, m). | Ex. 2 |
| 11 | OH | OH | H | 4-methylbiphenyl | H | R | $[\alpha]_D^{26} = +6.87$ (C = 0.34%) | >215 | ESI(Nega) 384(M − H)⁻ | 2.23–2.60(4H, m), 4.03–4.15(1H, m), 4.60–4.74(2H, m), 7.40–7.77(9H, m). | Ex. 2 |
| 12 | OH | OH | H | 3-(trifluoromethyl)phenyl-methyl | H | R | $[\alpha]_D^{28} = -12.6$ (C = 0.57%) | >220 | ESI(Nega) 376(M − H)⁻ | 2.28–2.54(4H, m), 4.08–4.15(1H, m), 4.62(1H, d, J=12.1Hz), 4.70(1H, d, J=12.1Hz), 7.55–7.71(4H, m). | Ex. 2 |

TABLE 1-continued

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 13 | OH | OH | H | 3-methoxyphenyl (m-OMe-C₆H₄-) | H | R | $[\alpha]_D^{24} = -8.4$ (C = 0.07%) | >165 | ESI(Nega) 338(M − H)⁻ | 2.24–2.46(3H, m), 2.51(1H, dd, J=7.5, 13.6Hz), 3.85(3H, s), 4.09(1H, dt, J=5.0, 7.5Hz), 4.54(1H, d, J=11.7Hz), 4.61(1H, d, J=11.7Hz), 6.95–7.15(3H, m), 7.38(1H, t, J=8.1Hz). | Ex. 2 |
| 14 | OH | OH | H | 3-phenoxyphenyl (m-PhO-C₆H₄-) | H | R | $[\alpha]_D^{27} = -9.4$ (C = 0.36%) | >180 | ESI(Nega) 400(M − H)⁻ | 2.26–2.49(4H, m), 4.03–4.09(1H, m), 4.53(1H, d, J=12.0Hz), 4.61(1H, d, J=12.0Hz), 7.05–7.26(6H, m), 7.40–7.48(3H, m). | Ex. 2 |
| 15 | OH | OH | H | 3-cyanophenyl (m-CN-C₆H₄-) | H | R | $[\alpha]_D^{28} = -11.8$ (C = 0.32%) | >184 | ESI(Nega) 333(M − H)⁻ | 2.26–2.54(4H, m), 4.09–4.13(1H, m), 4.59(1H, d, J=12.0Hz), 4.46(1H, d, J=12.0Hz), 7.50(1H, t, J=7.9Hz), 7.68(1H, d, J=7.9Hz), 7.73(1H, d, J=7.9Hz), 7.76(1H, s). | Ex. 2 |

TABLE 1-continued

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 16 | OH | OH | H | 3-CO₂H-phenyl | H | R | $[\alpha]_D^{26} = -13.6$ (C = 0.23%) | >195 | ESI(Nega) 352(M − H)⁻ | 2.25–2.34(2H, m), 2.36–2.0(2H, m), 4.04–4.18(1H, m), 4.57–4.73(2H, m), 7.40–7.64(2H, m), 7.83–7.93(2H, m). | Ex. 2 |
| 17 | OH | OH | H | 3-NO₂-phenyl | H | R | $[\alpha]_D^{26} = -14.1$ (C = 0.24%) | >234 | ESI(Nega) 353(M − H)⁻ | 2.24–2.34(2H, m), 2.36–2.62(2H, m), 4.08–4.20(1H, m), 4.64–4.80(2H, m), 7.64–7.68(1H, m), 7.76–7.84(1H, m), 8.18–8.28(2H, m). | Ex. 2 |
| 18 | OH | OH | H | 3-NH₂-phenyl | H | R | $[\alpha]_D^{28} = -19.1$ (C = 0.26%, H₂O) | >190 | ESI(Nega) 323(M − H)⁻ | 2.23–2.32(2H, m), 2.34–2.60(2H, m), 4.05–4.13(1H, m), 4.48–4.66(2H, m), 7.00–7.14(3H, m), 7.32–7.41(1H, m). | Ex. 6 |
| 19 | OH | OH | H | 4-F-phenyl | H | R | $[\alpha]_D^{29} = -18.9$ (C = 0.61%) | >239 | ESI(Nega) 326(M − H)⁻ | 2.29–2.54(4H, m), 4.07–4.14(1H, m), 4.53(1H, d, J=11.5Hz), 4.60(1H, d, J=11.5Hz), 7.11–7.18(2H, m), 7.37–7.42(2H, m). | Ex. 2 |

TABLE 1-continued

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 20 | OH | OH | H | 2-chlorophenyl | H | R | | >195 | ESI(Nega) 342(M − H)⁻ | 2.22–2.49(3H, m), 2.57(1H, dd, J=7.5, 13.5Hz), 4.15–4.21(1H, m), 4.66–4.82(2H, m), 7.33–7.50(4H, m). | Ex. 2 |
| 21 | OH | OH | H | 3-chlorophenyl | H | R | [α]ᴅ²⁷ = −12.5 (C = 0.63%) | >220 | ESI(Nega) 342(M − H)⁻ | 2.23–2.56(4H, m), 4.06–4.13(1H, m), 4.55(1H, d, J=12.1Hz), 4.63(1H, d, J=12.1Hz), 7.31–7.44(4H, m). | Ex. 2 |
| 22 | OH | OH | H | 4-chlorophenyl | H | R | [α]ᴅ²⁹ = −8.0 (C = 0.53%) | >220 | ESI(Nega) 342(M − H)⁻ | 2.29–2.54(4H, m), 4.05–4.12(1H, m), 4.54(1H, d, J=11.7Hz), 4.61(1H, d, J=11.7Hz), 7.35–7.44(4H, m). | Ex. 2 |
| 23 | OH | OH | H | 3-bromophenyl | H | R | [α]ᴅ²⁹ = −11.7 (C = 0.33%) | >250 | FAB(Nega) 386(M − H)⁻ | 2.20–2.48(3H, m), 2.51(1H, dd, J=7.5, 13.5Hz), 4.04–4.12(1H, m), 4.54(1H, d, J=12.1Hz), 4.61(1H, d, J=12.1Hz), 7.30–7.59(4H, m). | Ex. 2 |
| 24 | OH | OH | H | 2,3-difluorophenyl | H | R | [α]ᴅ²⁶ = −18.9 (C = 0.21%) | >180 | ESI(Nega) 344(M − H)⁻ | 2.29–2.56(4H, m), 4.09–4.16(1H, m), 4.63–4.76(2H, m), 7.14–7.31(3H, m). | Ex. 2 |

TABLE 1-continued

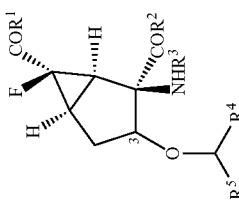

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 25 | OH | OH | H | 2,4-difluorophenyl | H | R | $[\alpha]_D^{27} = -8.7$ (C = 0.48%) | >170 | ESI(Nega) 344(M − H)⁻ | 2.22–2.55(4H, m), 4.10–4.17(1H, m), 4.60(1H, d, J=11.7Hz), 4.65(1H, d, J=11.7Hz), 6.94–7.02(2H, m), 7.40–7.48(1H, m). | Ex. 2 |
| 26 | OH | OH | H | 2,5-difluorophenyl | H | R |  | >200 | ESI(Nega) 344(M − H)⁻ | 2.22–2.57(4H, m), 4.09–4.15(1H, m), 4.52–4.74(2H, m), 7.07–7.24(3H, m). | Ex. 2 |
| 27 | OH | OH | H | 2,3-difluorophenyl | H | R | $[\alpha]_D^{26} = -5.1$ (C = 0.26%) | >180 | ESI(Nega) 344(M − H)⁻ | 2.27–2.53(4H, m), 4.08–4.15(1H, m), 4.64–4.77(2H, m), 6.98–7.07(2H, m), 7.37–7.47(1H, m). | Ex. 2 |
| 28 | OH | OH | H | 3,5-difluorophenyl | H | R | $[\alpha]_D^{27} = -16.0$ (C = 1.07%) | >220 | ESI(Nega) 344(M − H)⁻ | 2.25–2.46(3H, m), 2.51(1H, dd, J=7.8, 12.8Hz), 4.10(1H, dd, J=6.6, 12.8Hz), 4.52(1H, d, J=11.7Hz), 4.59(1H, d, J=11.7Hz), 7.16–7.37(3H, m). | Ex. 2 |

TABLE 1-continued

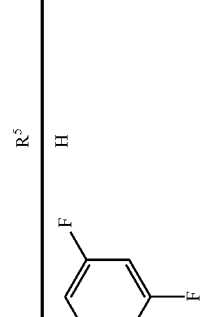

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 29 | OH | OH | H | 3,5-difluorophenyl | H | R | $[\alpha]_D^{27} = -14.4$ (C = 1.08%) | >185 | ESI(Nega) 344(M − H)⁻ | 2.22–2.58(4H, m), 4.07–4.14(1H, m), 4.55(1H, d, J=12.7Hz), 4.62(1H, d, J=12.7Hz), 6.87–7.01(3H, m). | Ex. 2 |
| 30 | OH | OH | H | 2,3-dichlorophenyl | H | R | $[\alpha]_D^{25} = -37.8$ (C = 0.40%) | >210 | ESI(Nega) 376(M − H)⁻ | 2.28–2.62(4H, m), 4.13–4.23(1H, m), 4.70–4.85(2H, m), 7.31–7.56(3H, m). | Ex. 2 |
| 31 | OH | OH | H | 2,4-dichlorophenyl | H | R | $[\alpha]_D^{24} = -21.1$ (C = 0.25%) | >215 | ESI(Nega) 376(M − H)⁻ | 2.28–2.60(4H, m), 4.13–4.19(1H, m), 4.62–4.84(2H, m), 7.37–7.54(3H, m). | Ex. 2 |
| 32 | OH | OH | H | 3,4-dichlorophenyl | H | R | | >195 | ESI(Nega) 376(M − H)⁻ | 2.22–2.62(4H, m), 4.15–4.20(1H, m), 4.62–4.85(2H, m), 7.32–7.56(3H, m). | Ex. 2 |
| 33 | OH | OH | H | 2,6-dichlorophenyl | H | R | $[\alpha]_D^{26} = -18.9$ (C = 0.42%) | >195 | ESI(Nega) 376(M − H)⁻ | 2.22–2.59(4H, m), 4.17–4.24(1H, m), 4.76–5.45(2H, m), 4.96(1H, d, J=10.9Hz), 7.29–7.48(3H, m). | Ex. 2 |

TABLE 1-continued

[Structure: bicyclic core with F, COR¹, H, COR², NHR³ substituents, and position 3 bearing O-CHR⁴R⁵]

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 34 | OH | OH | H | 3,4-dichlorophenyl | H | R | $[\alpha]_D^{27} = -10.0$ (C = 1.02%) | >230 | FAB(Nega) 376(M − H)⁻ | 2.28–2.45(3H, m), 2.50(1H, dd, J=7.6, 13.4Hz), 4.05–4.11(1H, m), 4.52(1H, d, J=12.1Hz), 4.60(1H, d, J=12.1Hz), 7.26–7.58(3H, m). | Ex. 2 |
| 35 | OH | OH | H | 3,4-dichlorophenyl | H | S | $[\alpha]_D^{27} = -28.3$ (C = 0.33%) | >243 | ESI(Nega) 376(M − H)⁻ | 2.06(1H, dd, J=4.3, 14.8Hz), 2.18–2.30(1H, m), 2.30–2.40(1H, m), 2.65–2.83(1H, m), 4.48–4.58(3H, m), 7.29(1H, d, J=7.9Hz), 7.54(1H, d, J=7.9Hz), 7.56(1H, s). | Ex. 2 |
| 36 | OH | OH | H | 3,5-dichlorophenyl | H | R | $[\alpha]_D^{27} = -9.4$ (C = 0.38%) | >180 | ESI(Nega) 376(M − H)⁻ | 2.22–2.55(4H, m), 4.05–4.12(1H, m), 4.52(1H, d, J=12.4Hz), 4.60(1H, d, J=12.4Hz), 7.34–7.44(3H, m). | Ex. 2 |
| 37 | OH | OH | H | 3-chloro-5-fluorophenyl | H | R | $[\alpha]_D^{27} = -8.7$ (C = 0.43%) | >276 | ESI(Nega) 360(M − H)⁻ | 2.22–2.45(3H, m), 2.51(1H, dd, J=7.6, 13.4Hz), 4.02–4.20(1H, m), 4.54(1H, d, J=12.1Hz), 4.61(1H, d, J=12.1Hz), 7.13–7.20(1H, m), 7.22–7.30(1H, m), 7.44–7.53(1H, m). | Ex. 2 |

TABLE 1-continued
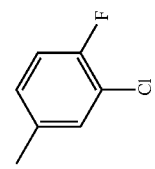
| Compound No. | R¹ | R² | R³ | R⁴ | R⁵ | 3-abs. conf. | Specific rotation (1 N aq. NaOH) | m.p.(° C.) decomposition | MS | ¹H NMR(D$_2$O)δ(ppm) | Syn. proc. |
|---|---|---|---|---|---|---|---|---|---|---|---|
| 38 | OH | OH | H | 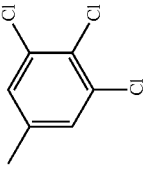 | H | R | [α]$_D^{25}$ = −17.6 (C = 0.45%) | >174 | ESI(Nega) 360(M − H)⁻ | 2.23–2.30(2H, m), 2.33–2.46(1H, m), 2.53(1H, dd, J=7.8, 13.7Hz), 4.06–4.18(1H, m), 4.62–4.73(2H, m), 7.16–7.23(1H,m), 7.35–7.43(1H, m), 7.45–7.53(1H, m). | Ex. 2 |
| 39 | OH | OH | H | 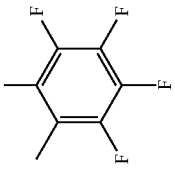 | H | R | [α]$_D^{29}$ = −4.1 (C = 0.39%) | >189 | ESI(Nega) 410(M − )⁻ | 2.28–2.29(2H, m), 2.36–2.43(1H, m), 2.50(1H, dd, J=13.4, 7.3Hz), 4.05–4.11(1H, m), 4.51(1H, d, J=13.4Hz), 4.59(1H, d,J=13.4Hz), 7.51(2H, s). | Ex. 2 |
| 40 | OH | OH | H | (pentafluorophenyl CH) | H | R | | >250 | ESI(Nega) 398(M − H)⁻ | 2.22–2.58(4H, m), 4.07–4.14(1H, m), 4.64–4.82(2H, m). | Ex. 2 |

TABLE 1-continued

![Structure: bicyclic cyclopropane-fused cyclopentane with F, COR¹, H, COR², NHR³ substituents and OCH(R⁴)(R⁵) at position 3]

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 41 | OH | OH | H | 1-naphthyl | H | R | $[\alpha]_D^{26} = -25.7$ (C = 0.19%) | >185 | ESI(Nega) 358(M − H)⁻ | 2.23–2.48(4H, m), 4.15–4.21(1H, m), 5.02(1H, d, J=11.9Hz), 5.09(1H, d, J=11.9Hz), 7.50–7.68(4H, m), 7.94–8.05(2H, m), 8.15(1H, d, J=8.1Hz). | Ex. 2 |
| 42 | OH | OH | H | 2-naphthyl | H | R | $[\alpha]_D^{30} = +5.7$ (C = 0.50%) | >210 | ESI(Nega) 358(M − H)⁻ | 2.25–2.55(4H, m), 4.10–4.19(1H, m), 4.73–4.84(2H, m), 7.58–7.61(3H, m), 7.92–7.99(4H, m). | Ex. 2 |
| 43 | OH | OH | H | 2-thienyl | H | R | $[\alpha]_D^{28} = -11.6$ (C = 0.36%) | >212 | ESI(Nega) 314(M − H)⁻ | 2.28–2.51(4H, m), 4.09–4.13(1H, m), 4.77–4.79(2H, m), 7.50(1H, dd, J=7.9Hz), 7.68(1H, d, J=7.9Hz), 7.73(1H, d, J=7.9Hz), 7.76(1H, s). | Ex. 2 |
| 44 | OH | OH | H | Me | n-Pr | R | — | >170 | ESI(Nega) 288(M − H)⁻ | 0.80–0.94(3H, m), 1.06–1.16(3H, m), 1.20–1.42(3H, m), 1.42–1.58(1H, m), 2.18–2.30(2H, m), 2.32–2.48(1H, m), 2.48–2.60(1H, m), 3.43–3.63(1H, m), 4.03–4.18(1H, m). | Ex. 5 |

TABLE 1-continued

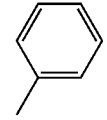

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 45 | OH | OH | H | 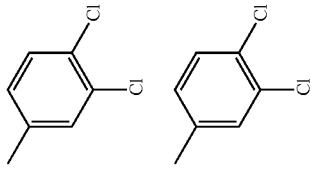 | Me | R | — | >190 | ESI(Nega) 322(M − H)⁻ | 1.39(3H×²/₁₂, d, J=6.5Hz), 1.42(3H×⁷/₁₂, d, J=6.5Hz), 2.14–2.63(4H, m), 3.76–3.85(1H×⁷/₁₂, m), 3.88–3.97(1H×⁵/₁₂, m), 4.53–4.70(1H,m), 7.35–7.50(5H, m). | Ex. 2 |
| 46 | OH | OH | H | 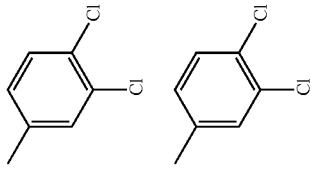 | Me(R*) | R | $[\alpha]_D^{27} = +94.2$ (C = 0.95%) | >186 | ESI(Nega) 390(M − H)⁻ | 1.36(3H, t, J=6.1Hz), 2.10–2.39(4H, m), 3.84–3.97(1H, m), 4.59(1H, q, J=6.1Hz), 7.24(1H, d, J=7.2Hz), 7.53(1H, s), 7.55(1H,d, J=7.2Hz). | Ex. 3 |
| 47 | OH | OH | H | 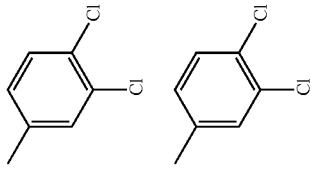 | Me(S*) | R | $[\alpha]_D^{27} = -62.1$ (C = 1.39%) | >167 | ESI(Nega) 390(M − H)⁻ | 1.38(3H, d, J=6.4Hz), 2.21(1H, dd, J=2.7, 7.8Hz), 2.24–2.32(1H, m), 2.39–2.59(2H, m), 3.73–3.86(1H, m), 4.54(1H, q,J=6.4Hz), 7.30(1H, d, J=8.2Hz), 7.55(1H, d, J=8.2Hz), 7.56(1H, s). | Ex. 3 |

TABLE 1-continued

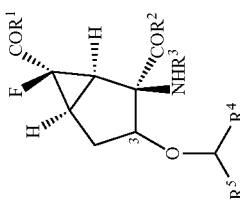

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 48 | OH | OH | H |  3,4-diCl-phenyl | Et(R*) | R | $[\alpha]_D^{28} = +68.4$ (C = 1.04%) | >165 | ESI(Nega) 404(M − H)⁻ | 0.78(3H, t, J=7.2Hz), 1.50–1.68(1H, m), 1.70–1.89(1H, m), 2.03–2.37(4H, m), 2.38–2.62(2H, m), 3.83–3.95(1H, m), 4.34(1H, t, J=6.8Hz), 7.26(1H, d, J=8.2Hz), 7.51(1H, s), 7.55(1H, d, J=8.2Hz). | Ex. 3 |
| 49 | OH | OH | H | 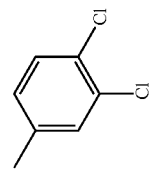 3,4-diCl-phenyl | Et(S*) | R | $[\alpha]_D^{29} = -71.6$ (C = 1.21%) | >170 | ESI(Nega) 404(M − H)⁻ | 0.81(3H, t, J=7.3Hz), 1.52–1.70(1H, m), 1.70–1.90(1H, m), 2.06–2.36(2H, m), 2.38–2.62(2H, m), 3.70–3.82(1H, m), 4.28(1H, t, J=6.7Hz), 7.30(1H, d, J=8.2Hz), 7.56(1H, s), 7.57(1H, d, J=8.2Hz). | Ex. 3 |
| 50 | OH | OH | H | 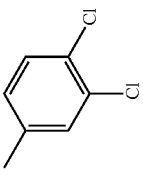 3,4-diCl-phenyl | n-Pr(R*) | R | $[\alpha]_D^{28} = -63.3$ (C = 1.07%) | >190 | ESI(Nega) 418(M − H)⁻ | 0.86(3H, t, J=7.2Hz), 1.12–1.40(2H, m), 1.46–1.64(1H, m), 1.70–1.86(1H, m), 2.12–2.34(2H, m), 2.38–2.64(2H, m), 3.68–3.83(1H, m), 4.36(1H, t, J=6.6Hz), 7.30(1H, d, J=8.4Hz), 7.53–7.60(2H, m). | Ex. 3 |

TABLE 1-continued

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 51 | OH | OH | H | 3,4-dichlorophenyl | n-Pr(S*) | R | $[\alpha]_D^{30} = +63.9$ (C = 0.82%) | >188 | ESI(Nega) 418(M − H)⁻ | 0.84(3H, t, J=7.4Hz), 1.04–1.38(2H, m), 1.42–1.64(1H, m), 1.70–1.86(1H, m), 2.00–2.39(4H, m), 3.83–3.98(1H, m), 4.42(1H, t, J=6.8Hz), 7.27(1H, d, J=9.5Hz), 7.50–7.59(2H, m). | Ex. 3 |
| 52 | OH | OH | H | phenyl | phenyl | R | $[\alpha]_D^{26} = -29.8$ (C = 1.04%) | >230 | ESI(Nega) 384(M − H)⁻ | 2.23–2.53(4H, m), 4.01–4.08(1H, m), 5.61(1H, s), 7.35–7.44(1H, m). | Ex. 2 |
| 53 | OH | OH | H | 4-fluorophenyl | 4-fluorophenyl | R | $[\alpha]_D^{24} = -24.5$ (C = 1.05%) | >190 | ESI(Nega) 420(M − H)⁻ | 2.25–2.42(4H, m), 3.99–4.06(1H, m), 5.61(1H, s), 7.10–7.17(4H, m), 7.37–7.43(4H, m). | Ex. 2 |
| 54 | OH | OH | H | 4-chlorophenyl | 4-chlorophenyl | R | | >215 | ESI(Nega) 452(M − H)⁻ | 2.25–2.49(4H, m), 3.98–4.07(1H, m), 5.59(1H, s), 7.34–7.44(8H, m). | Ex. 2 |
| 55 | OH | OH | H | 4-chlorophenyl | 4-chlorophenyl | S | $[\alpha]_D^{27} = -25.3$ (C = 0.30%) | >260 | ESI(Nega) 452(M − H)⁻ | 1.98–2.12(1H, m), 2.14–2.26(1H, m), 2.29–2.39(1H, m), 2.55–2.72(1H, m), 4.46–4.60(1H, m), 5.58(1H, s), 7.33–7.47(8H, m). | Ex. 2 |

TABLE 1-continued
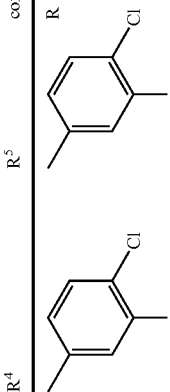
| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 56 | OH | OH | H |  | 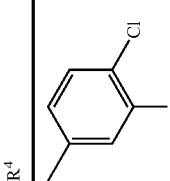 | R | $[\alpha]_D^{31} = -5.1$ (C = 0.42%) | >206 | ESI(Nega) 520(M − H)⁻ | 2.26–2.47(4H, m), 3.96–4.10(1H, m), 5.57(1H, s), 7.31(1H, d, J=8.2Hz), 7.53(1H, d, J=8.2Hz), 7.55(1H, s). | Ex. 2 |
| 57 | OH | OH | H | 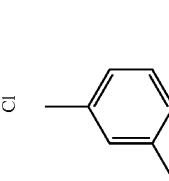 | Me(R*) | R | $[\alpha]_D^{22} = +72.4$ (C = 0.52%) | >185 | ESI(Nega) 372(M − H)⁻ | 1.47(3H, d, J=6.4Hz), 2.05(1H, dd, J=7.6, 13.8Hz), 2.10–2.16(1H, m), 2.24–2.38(2H, m), 3.96(1H, dt, J=5.0, 7.6Hz), 4.75–4.80(1H, m), 7.51–7.60(3H, m), 7.84(1H, s), 7.93–7.98(3H, m). | Ex. 3 |
| 58 | OH | OH | H |  | Me(S*) | R | $[\alpha]_D^{22} = -36.1$ (C = 0.49%) | >188 | ESI(Nega) 372(M − H)⁻ | 1.49(3H, d, J=6.4Hz), 2.20(1H, dd, J=2.0, 7.8Hz), 2.27–2.31(1H, m), 2.45–2.62(2H, m), 3.81(1H, dd, J=7.5, 12.5Hz), 4.71–4.80(1H, m), 7.55–7.62(3H, m), 7.89–8.01(4H, m). | Ex. 3 |

TABLE 1-continued
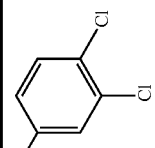
| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 59 | OEt | OEt | H | 3,4-dichlorophenyl | H | R | $[\alpha]_D^{26}$ = +12.9 (C = 0.60%, CHCl₃) | oil | ESI(Pos) 434(M + H)⁺ | 1.30(3H, t, J=7.3Hz), 1.31(3H, t, J=7.3Hz), 2.10–2.29(2H, m), 2.30–2.54(2H, m), 3.68–3.73(1H, m), 4.14–4.42(4H, m), 4.47(1H, d, J=12.1Hz), 4.64(1H, d, J=12.1Hz), 7.09(1H, dd, J=8.4, 1.8Hz), 7.37(1H, d, J=1.8Hz), 7.39(1H, d, J=8.4Hz). | Ex. 8 |
| 60*¹ | OEt | OH | H | 3,4-dichlorophenyl | H | R | $[\alpha]_D^{29}$ = −8.1 (C = 0.24%) | >158 | ESI(Nega) 404(M − H)⁻ | 1.29(3H, t, J=6.9Hz), 2.34–2.50(2H, m), 2.52–2.68(2H, m), 4.05–4.18(1H, m), 4.20–4.34(1H, m), 4.48–4.63(1H, m), 7.15–7.20(1H, m), 7.47(1H, d, J=7.3Hz), 7.52(1H, s). | Ex. 8 |

TABLE 1-continued

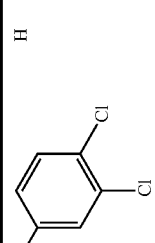

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 61 | OH | OEt | H | 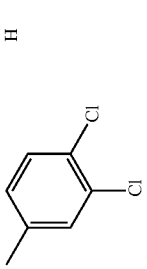 | H | R | $[\alpha]_D^{28} = -24.8$ (C = 0.35%) | >233 | ESI(Nega) 404(M − H)⁻ | 1.31(3H, t, J=7.3Hz), 2.26(1H, dd, J=7.9, 2.4Hz), 2.30–2.33(1H, m), 2.44–2.49(1H, m), 2.55(1H, dd, J=13.4, 7.32Hz), 4.08–4.12(1H, m), 4.29–4.42(2H, m), 4.51(1H, d, J=12.8Hz), 4.54(1H, d, J=12.8Hz), 7.22(1H, d, J=8.5Hz), 7.49(1H, d, J=8.5Hz), 7.50(1H, s). | Ex. 9 |
| 62 | OH | OH | H | (3,4-dichlorophenyl) | H | R | $[\alpha]_D^{25} = -7.6$ (C = 0.46%) | >190 | ESI(Nega) 489(M − H)⁻ | 0.89–0.94(6H, m), 1.62–1.71(3H, m), 2.37–2.39(2H, m), 2.44–2.49(1H, m), 2.55(1H, dd, J=7.9, 14.0Hz), 4.10–4.14(1H, m), 4.29–4.32(1H, m), 4.54(1H, d, J=11.6Hz), 4.61(1H, d, J=11.6Hz), 5.30(1H, d, J=8.4Hz), 7.55(1H, d, J=8.4Hz), 7.56(1H, s). | Ex. 11 |

Compound 62 R¹: structure with Me, Me, H, COOH, N—H (N-methyl leucine-like group)

TABLE 1-continued

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 63*¹ | OH | H | H | (S)-CH(Me)(NH₂)C(O)– group (Me, NH₂ on chiral carbon, C=O linker) | H | R | $[\alpha]_D^{26} = -56.7$ (C = 0.22%) | >260 | ESI(Nega) 447(M − H)⁻ | 1.49(3H, d, J=6.8Hz), 2.07–2.18(1H, m), 2.21–2.38(1H, m), 2.44–2.56(1H, m), 2.75–2.83(1H, m), 4.02–4.22(2H, m), 4.50(1H, d, J=11.3Hz), 4.71(1H, d, J=11.3Hz), 7.29(1H, d, J=7.8Hz), 7.50–7.58(2H, m). | Ex. 10 |
| 64 | OEt | OBn | H | —CH=CH₂ | H | R | $[\alpha]_D^{26} = -17.4$ (C = 0.04%, CHCl₃) | oil | ESI(Pos) 400(M + H)⁺ | 1.30(3H, t, J=7.3Hz), 2.06–2.52(4H, m), 3.64–3.82(1H, m), 3.92–4.14(2H, m), 4.24(2H, q, J=7.3Hz), 5.08–5.37(4H, m), 5.66–5.85(1H, m), 7.30–7.48(5H, m). | Ex. 2 |
| 65 | OEt | OBn | H | phenyl | H | R |  | oil | ESI(Pos) 450(M + Na)⁺ | 1.29(3H, t, J=7.2Hz), 2.08–2.15(1H, m), 2.22–2.28(1H, m), 2.35–2.44(1H, m), 3.70–3.82(1H, m), 4.23(2H, q, J=7.2Hz), 4.51(1H, d, J=11.7Hz), 4.61(1H, d, J=11.7Hz), 5.19(1H, d, J=12.8Hz), 5.30(1H, d, J=12.5Hz), 7.20–7.38(10H, m). | Ex. 2 |

TABLE 1-continued

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 66 | OEt | OEt | H | (phenyl) | H | R | [α]$_D^{28}$ = −2.2 (C = 0.31%, CHCl₃) | oil | ESI(Pos) 366(M + H)⁺ | 1.20–1.38(6H, m), 2.08–2.48(4H, m), 3.68–3.85(1H, m), 4.15–4.40(4H, m), 4.44–4.65(2H, m), 7.21–7.42(5H, m). | Ex. 2 |
| 67 | OEt | OEt | H | —(CH₂)₂—(phenyl) | H | R | [α]$_D^{24}$ = −16.0 (C = 0.47%, CHCl₃) | oil | ESI(Pos) 416(M + Na)⁺ | 1.25–1.39(6H, m), 1.72–2.70(8H, m), 3.34–3.70(3H, m), 4.14–4.44(4H, m), 7.12–7.34(5H, m). | Ex. 1 |
| 68 | OEt | OBn | H | (3-methylphenyl) | H | R | | oil | ESI(Pos) 464 (M + Na)⁺ | 1.29(3H, t, J=7.2Hz), 2.08–2.45(4H, m), 2.32(3H, s), 3.74–3.82(1H, m), 4.23(2H, q, J=7.2Hz), 4.47(1H, d, J=11.7Hz), 4.58(1H, d, J=11.7Hz), 5.20(1H, d, J=12.4Hz), 5.30(1H, d, J=12.4Hz), 6.98–7.40(9H, m). | Ex. 2 |
| 69 | OEt | OBn | H | (2-phenylphenyl) | H | R | | oil | ESI(Pos) 526 (M + Na)⁺ | 1.20–1.35(3H, m), 2.08–2.35(4H, m), 3.85–4.00(1H, m), 4.27(2H, q, J=7.2Hz), 4.30–4.55(2H, m), 5.20(1H, d, J=12.2Hz), 5.34(1H, d, J=12.2Hz), 7.26–7.58(14H, m). | Ex. 2 |

TABLE 1-continued

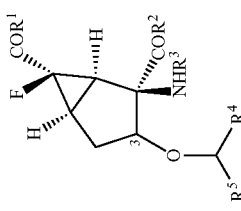

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 70 | OEt | OBn | H | ![3-biphenyl-CH2] | H | R | | oil | ESI(Pos) 526 (M + Na)⁺ | 1.20–1.33(3H, m), 2.10–2.50(4H, m), 3.75–3.88(1H, m), 4.16–4.30(2H, m), 4.57(1H, d, J=11.8Hz), 4.69(1H, d, J=11.8Hz), 5.19(1H, d, J=12.4Hz), 5.30(1H, d, J=12.4Hz), 7.16–7.58(14H, m). | Ex. 2 |
| 71 | OEt | OBn | H | ![4-biphenyl-CH2] | H | R | | oil | ESI(Pos) 526 (M + Na)⁺ | 1.22–1.34(3H, m), 2.08–2.50(4H, m), 3.74–3.88(1H, m), 4.19–4.28(2H, m), 4.55(1H, d, J=11.7Hz), 4.68(1H, d, J=11.7Hz), 5.20(1H, d, J=12.4Hz), 5.32(1H, d, J=12.4Hz), 7.20–7.62(14H, m). | Ex. 2 |
| 72 | OEt | OBn | H | ![3-CF3-benzyl] | H | R | | oil | ESI(Pos) 518 (M + Na)⁺ | 1.20–1.35(3H, m), 2.10–2.45(4H, m), 3.73–4.85(1H, m), 4.24(2H, q, J=7.2Hz), 4.54(1H, d, J=12.0Hz), 4.70(1H, d, J=12.0Hz), 5.19(1H, d, J=12.4Hz), 5.29(1H, d, J=12.4Hz), 7.26–7.51(9H, m). | Ex. 2 |

TABLE 1-continued

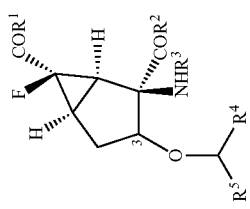

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 73 | OEt | OBn | H | 3-methylphenyl-OMe | H | R | | oil | ESI(Pos) 480(M + Na)⁺ | 1.20–1.40(3H, m), 2.05–2.45(4H, m), 3.70–3.85(4H, m), 4.15–4.30(2H, m), 4.49(1H, d, J=11.7Hz), 4.58(1H, d, J=11.7Hz), 5.20(1H, d, J=12.2Hz), 5.30(1H, d, J=12.2Hz), 6.80–7.40(8H, m). | Ex. 2 |
| 74 | OEt | OBn | H | 3-methylphenyl-OPh | H | R | | oil | ESI(Pos) 542 (M + Na)⁺ | 1.30(3H, t, J=7.0Hz), 2.06–2.46(4H, m), 3.69–3.84(1H, m), 4.24(2H, q, J=7.0Hz), 4.48(1H, d, J=12.1Hz), 4.60(1H, d, J=12.1Hz), 5.14(1H, d, J=12.3Hz), 5.23(1H, d, J=12.3Hz), 6.76–7.40(14H, m). | Ex. 2 |
| 75 | OEt | OEt | H | 3-methylphenyl-CN | H | R | $[\alpha]_D^{26} = +10.9$ (C = 0.41%, CHCl₃) | oil | ESI(Pos) 413 (M + Na)⁺ | 1.21–1.38(6H, m), 2.12–2.54(4H, m), 3.71–3.88(1H, m), 4.19–4.35(4H, m), 4.55(1H, d, J=12.5Hz), 4.73(1H, d, J=12.5Hz), 7.36–7.62(4H, m). | Ex. 2 |

TABLE 1-continued

| Compound No. | R$^1$ | R$^2$ | R$^3$ | R$^4$ | R$^5$ | 3-abs. conf. | Specific rotation (1 N aq. NaOH) | m.p.(° C.) decomposition | MS | $^1$H NMR(D$_2$O)δ(ppm) | Syn. proc. |
|---|---|---|---|---|---|---|---|---|---|---|---|
| 76 | OEt | OEt | H | 3-CO$_2$Me-phenyl | H | R | [α]$_D^{27}$ = −6.0 (C = 0.66%, EtOH) | oil | ESI(Pos) 446 (M + Na)$^+$ | 1.24–1.36(6H, m), 2.12–2.29(2H, m), 2.38–2.49(2H, m), 3.70–3.86(1H, m), 3.92(3H, s), 4.14–4.42(4H, m), 4.56(1H, d, J=12.1Hz), 4.72(1H, d, J=12.1Hz), 7.33–7.52(2H, m), 7.90–8.01(2H, m). | Ex. 2 |
| 77 | OEt | OEt | H | 3-NO$_2$-phenyl | H | R | [α]$_D^{22}$ = −3.4 (C = 0.56%, CHCl$_3$) | oil | ESI(Pos) 433 (M + Na)$^+$ | 1.31(3H, t, J=7.0Hz), 1.32(3H, t, J=7.0Hz), 2.14–2.32(2H, m), 2.42–2.54(2H, m), 3.74–3.92(1H, m), 4.26(2H, q, J=7.0Hz), 4.17–4.46(2H, m), 4.62(1H, d, J=12.3Hz), 4.81(1H, d, J=12.3Hz), 7.44–7.64(2H, m), 8.09–8.20(2H, m). | Ex. 6 |
| 78 | OEt | OEt | H | 3-NH$_2$-phenyl | H | R | [α]$_D^{23}$ = −27.0 (C = 0.26%, CHCl$_3$) | oil | ESI(Pos) 403 (M + Na)$^+$ | 1.30(6H, t, J=7.1Hz), 2.04–2.28(2H, m), 2.32–2.50(2H, m), 3.68–3.82(1H, m), 4.14–4.38(4H, m), 4.44(1H, d, J=11.8Hz), 4.55(1H, d, J=11.8Hz), 6.53–6.70(3H, m), 7.02–7.18(1H, m). | Ex. 6 |

TABLE 1-continued
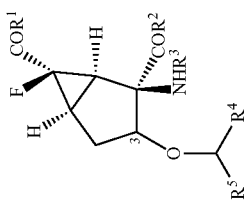
| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 79 | OEt | OBn | H | 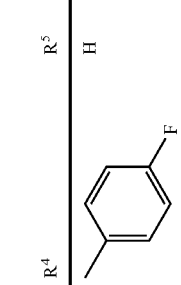 | H | R | | oil | ESI(Pos) 468 (M + Na)⁺ | 1.30(3H, t, J=7.3Hz), 2.08–2.45(4H, m), 3.70–3.85(1H, m), 4.24(2H, q, J=7.3Hz), 4.46(1H, d, J=11.5Hz), 4.59(1H, d, J=11.5Hz), 5.18(1H, d, J=12.4Hz), 5.31(1H, d, J=12.4Hz), 6.94–7.37(9H, m). | Ex. 2 |
| 80 | OEt | OBn | H | 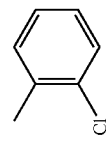 | H | R | | oil | ESI(Pos) 484 (M + Na)⁺ | 1.10–1.25(3H, m), 2.10–2.55(4H, m), 3.78–3.90(1H, m), 4.24(2H, q, J=7.2Hz), 4.55–4.70(2H, m), 5.19(1H, d, J=12.4Hz), 5.29(1H, d, J=12.4Hz), 7.19–7.35(9H, m). | Ex. 2 |
| 81 | OEt | OBn | H | (3-Cl-phenyl) | H | R | | oil | ESI(Pos) 484 (M + Na)⁺ | 1.20–1.35(3H, m), 2.10–2.45(4H, m), 3.70–3.85(1H, m), 4.24(2H, q, J=7.2Hz), 4.47(1H, d, J=12.0Hz), 4.60(1H, d, J=12.0Hz), 5.19(1H, d, J=12.3Hz), 5.31(1H, d, J=12.3Hz), 7.22–7.36(9H, m). | Ex. 2 |

TABLE 1-continued

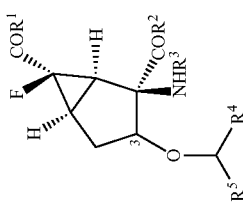

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 82 | OEt | OBn | H | 4-Cl-phenyl | H | R | | oil | ESI(Pos) 484 (M + Na)⁺ | 1.30(3H, t, J=7.1Hz), 2.12–2.16(1H, m), 2.24–2.27(1H, m), 2.36–2.41(2H, m), 3.73–3.81(1H, m), 4.24(2H, q, J=7.1Hz), 4.45(1H, d, J=11.7Hz), 4.58(1H, d, J=11.7Hz), 5.17(1H, d, J=12.3Hz), 5.29(1H, d, J=12.3Hz), 7.12–7.35(9H, m). | Ex. 2 |
| 83 | OEt | OBn | H | 3-Br-phenyl | H | R | | oil | ESI(Pos) 530 (M + Na)⁺ | 1.20–1.38(3H, m), 2.08–2.47(4H, m), 3.70–3.88(1H, m), 4.18–4.30(2H, m), 4.45(1H, d, J=12.0Hz), 4.60(1H, d, J=12.0Hz), 5.18(1H, d, J=12.3Hz), 5.30(1H, d, J=12.3Hz), 7.08–7.45(9H, m). | Ex. 2 |
| 84 | OEt | OBn | H | 2,3-diF-phenyl | H | R | | oil | ESI(Pos) 464(M + H)⁺ | 1.20–1.35(3H, m), 2.10–2.50(4H, m), 3.75–3.88(1H, m), 4.24(2H, q, J=7.2Hz), 4.55–4.73(2H, m), 5.18(1H, d, J=12.4Hz), 5.29(1H, d, J=12.4Hz), 6.98–7.36(8H, m). | Ex. 2 |

TABLE 1-continued
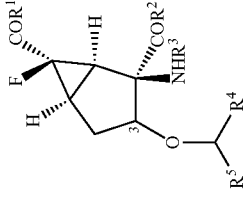
| Compound No. | R¹ | R² | R³ | R⁴ | R⁵ | 3-abs. conf. | Specific rotation (1 N aq. NaOH) | m.p.(° C.) decomposition | MS | ¹H NMR(D$_2$O)δ(ppm) | Syn. proc. |
|---|---|---|---|---|---|---|---|---|---|---|---|
| 85 | OEt | OBn | H | 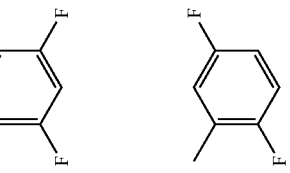 | H | R | | oil | ESI(Pos) 518(M + H)⁺ | 1.20–1.35(3H, m), 2.10–2.50(4H, m), 3.73–3.85(1H, m), 4.24(2H, q, J=7.2Hz), 4.45–4.65(2H, m), 5.17(1H, d, J=12.4Hz), 5.28(1H, d, J=12.4Hz), 6.73–6.81(2H, m), 7.21–7.35(6H, m). | Ex. 2 |
| 86 | OEt | OBn | H | 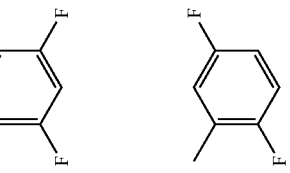 | H | R | | oil | ESI(Pos) 46(M + H)⁺ | 1.20–1.35(3H, m), 2.10–2.55(4H, m), 3.75–3.88(1H, m), 4.15–4.30(2H, m), 4.54(1H, d, J=12.7Hz), 4.63(1H, d, J=12.7Hz), 5.19(1H, d, J=12.4Hz), 5.31(1H, d, J=12.4Hz), 6.90–7.37(8H, m). | Ex. 2 |
| 87 | OEt | OBn | H | 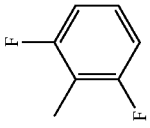 | H | R | | oil | ESI(Pos) 486(M + Na)⁺ | 1.10–1.33(3H, m), 2.08–2.45(4H, m), 3.73–3.88(1H, m), 4.18–4.28(2H, m), 4.60(1H, d, J=12.0Hz), 4.73(1H, d, J=12.0Hz), 5.18(1H, d, J=12.3Hz), 5.28(1H, d, J=12.3Hz), 6.88(2H, t, J=7.5Hz), 7.20–7.40(6H, m). | Ex. 2 |

TABLE 1-continued

[Structure: bicyclic compound with F, COR¹, H, COR², NHR³, and O-CHR⁴R⁵ substituent at position 3]

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 88 | OEt | OBn | H | 3,4-difluorophenyl | H | R | | oil | ESI(Pos) 486 (M + Na)⁺ | 1.20–1.35(3H, m), 2.10–2.50(4H, m), 3.70–3.83(1H, m), 4.18–4.30(2H, m), 4.38–4.60(2H, m), 5.20(1H, d, J=12.2Hz), 5.32(1H, d, J=12.2Hz), 6.93–7.34(8H, m). | Ex. 2 |
| 89 | OEt | OBn | H | 3,5-difluorophenyl | H | R | | oil | ESI(Pos) 486 (M + Na)⁺ | 1.18–1.38(3H, m), 2.09–2.50(4H, m), 3.68–3.85(1H, m), 4.15–4.32(2H, m), 4.40–4.68(2H, m), 5.12–5.18(2H, m), 6.60–6.80(2H, m), 7.20–7.45(6H, m). | Ex. 2 |
| 90 | OEt | OBn | H | 2,3-dichlorophenyl | H | R | | oil | ESI(Pos) 518 (M + Na)⁺ | 1.22–1.36(3H, m), 2.12–2.58(4H, m), 3.80–3.90(1H, m), 4.19–4.30(2H, m), 4.52–4.70(2H, m), 5.12–5.35(2H, m), 7.06–7.43(8H, m). | Ex. 2 |
| 91 | OEt | OBn | H | 2,4-dichlorophenyl | H | R | | oil | ESI(Pos) 496(M + H)⁺ | 1.19–1.40(3H, m), 2.10–2.58(4H, m), 3.65–3.90(1H, m), 4.15–4.35(2H, m), 4.52–4.58(2H, m), 5.16(1H, d, J=12.5Hz), 5.30(1H, d, J=12.5Hz), 7.10–7.30(8H, m). | Ex. 2 |

TABLE 1-continued

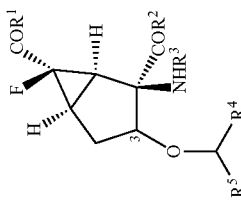

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 92 | OEt | OBn | H | 2,5-dichlorophenyl (Cl at 2,5) | H | R | | oil | ESI(Pos) 518 (M + Na)⁺ | 1.23–1.38(3H, m), 2.10–2.58(4H, m), 3.80–3.90(1H, m), 4.20–4.33(2H, m), 4.48–4.70(2H, m), 5.15–5.38(2H, m), 7.13–7.43(8H, m). | Ex. 2 |
| 93 | OEt | OBn | H | 2,3-dichlorophenyl | H | R | | oil | | 1.23–1.33(3H, m), 2.05–2.50(4H, m), 3.80–3.90(1H, m), 4.23(2H, q, J=7.2Hz), 4.76(1H, d, J=10.7Hz), 4.87(1H, d, J=10.7Hz), 5.16(1H, d, J=12.4Hz), 5.25(1H, d, J=12.4Hz), 7.15–7.34(8H, m). | Ex. 2 |
| 94 | OEt | OBn | H | 3,5-dichlorophenyl | H | R | | oil | ESI(Pos) 496(M + H)⁺ | 1.20–1.35(3H, m), 2.05–2.50(4H, m), 3.68–3.85(1H, m), 4.18–4.35(2H, m), 4.38–4.65(2H, m), 5.05–5.38(2H, m), 7.05–7.45(8H, m). | Ex. 2 |
| 95 | OEt | OEt | H | 3,4-dichlorophenyl | H | S | [α]D²² = +11.6 (C = 0.50%, CHCl₃) | oil | ESI(Pos) 456 (M + Na)⁺ | 1.24–1.40(6H, m), 2.02–2.28(2H, m), 2.51–2.80(2H, m), 3.98–4.08(1H, m), 4.18–4.34(4H, m), 4.43(1H, d, J=12.5Hz), 4.53(1H, d,J=12.5Hz), 7.10–71.9(2H, m), 7.36–7.45(2H, m). | Ex. 2 |

TABLE 1-continued

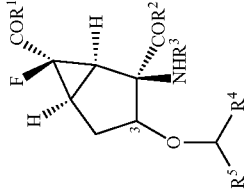

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 96 | OEt | OBn | H | 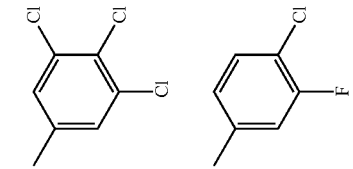 | H | R | $[\alpha]_D^{28} = -1.5$ (C = 1.15%, CHCl₃) | oil | ESI(Pos) 480(M + H)⁺ | 1.30(3H, t, J=7.3Hz), 2.06–2.54(4H, m), 3.73–3.92(1H, m), 4.24(2H, q, J=7.3Hz), 4.53–4.72(2H, m), 5.17(1H, d, J=12.3Hz), 5.30(1H, d, J=12.3Hz), 6.94–7.40(8H, m). | Ex. 2 |
| 97 | OEt | OEt | H | | H | R | | oil | ESI(Pos) 490 (M + Na)⁺ | 1.32(6H, t, J=7.1Hz), 2.18–2.46(4H, m), 3.70–3.85(1H, m), 4.15–4.40(4H, m), 4.45(1H, d, J=12.3Hz), 4.64(1H, d, J=12.3Hz), 7.29(1H, s), 7.32(1H, s). | Ex. 2 |
| 98 | OEt | OBn | H | | H | R | $[\alpha]_D^{29} = +11.9$ (C = 1.05%, CHCl₃) | oil | ESI(Pos) 480(M + H)⁺ | 1.31(3H, t, J=7.3Hz), 2.10–2.48(4H, m), 3.72–3.86(1H, m), 4.25(2H, q, J=7.3Hz), 4.44(1H, d, J=12.1Hz), 4.60(1H, d, J=12.1Hz), 5.18(1H, d, J=12.1Hz), 5.32(1H, d, J=12.1Hz), 6.86–7.06(2H, m), 7.28–7.38(6H, m). | Ex. 2 |

TABLE 1-continued

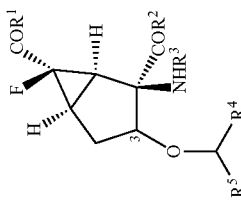

| Compound No. | R$^1$ | R$^2$ | R$^3$ | R$^4$ | R$^5$ | 3-abs. conf. | Specific rotation (1 N aq. NaOH) | m.p.(° C.) decomposition | MS | $^1$H NMR(D$_2$O)δ(ppm) | Syn. proc. |
|---|---|---|---|---|---|---|---|---|---|---|---|
| 99 | OEt | OEt | H | pentafluorophenyl | H | R | [α]$_D^{26}$ = +4.5 (C = 0.44%, CHCl$_3$) | oil | ESI(Pos) 456(M + H)$^+$ | 1.20–1.39(6H, m), 2.10–2.54(4H, m), 3.70–3.86(1H, m), 4.16–4.40(4H, m), 4.52–4.82(2H, m). | Ex. 2 |
| 100 | OEt | OBn | H | 1-naphthyl | H | R | | oil | ESI(Pos) 500 (M + Na)$^+$ | 1.20–1.32(3H, m), 2.05–2.40(4H, m), 3.80–3.91(1H, m), 4.18–4.28(2H, m), 4.95(1H, d, J=12.0Hz), 5.03(1H, d, J=12.0Hz), 5.15(1H, d, J=12.4Hz), 5.26(1H, d, J=12.4Hz), 7.20–7.54(9H, m), 7.78–7.89(2H, m), 7.95–8.04(1H, m). | Ex. 2 |
| 101 | OEt | OBn | H | 2-naphthyl | H | R | | oil | ESI(Pos) 500 (M + Na)$^+$ | 1.20–1.35(3H, m), 2.10–2.48(4H, m), 3.80–3.90(1H, m), 4.18–4.28(2H, m), 4.66(1H, d, J=11.8Hz), 4.77(1H, d, J=11.8Hz), 5.20(1H, d, J=12.3Hz), 5.32(1H, d, J=12.3Hz), 7.22–7.83(12H, m). | Ex. 2 |

TABLE 1-continued

[Structure: bicyclic compound with F, COR¹, H, COR², NHR³, and O-CH(R⁴)(R⁵) substituent at position 3]

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 102 | OEt | OEt | H | 2-thienyl | H | R | [α]_D^25 = +1.7 (C = 0.42%, CHCl₃) | oil | ESI(Pos) 394 (M + Na)⁺ | 1.23–1.40(6H, m), 2.05–2.45(4H, m), 3.68–3.85(1H, m), 4.15–4.45(4H, m), 4.65–4.85(2H, m), 6.90–7.00(2H, m), 7.23–7.33(1H, m). | Ex. 2 |
| 103 | OEt | OEt | H | Me | n-Pr | R | — | oil | ESI(Pos) 368 (M + Na)⁺ | 0.82–0.94(3H, m), 1.02–1.10(3H, m), 1.16–1.46(10H, m), 2.06–2.44(4H, m), 3.32–3.78(2H, m), 4.12–4.40(4H, m). | Ex. 5 |
| 104 | OEt | OBn | H | 3,4-dichlorophenyl | Me(R*) | R | [α]_D^29 = +39.9 (C = 1.37%, CHCl₃) | oil | ESI(Pos) 532 (M + Na)⁺ | 1.20–1.35(6H, m), 2.00–2.40(4H, m), 3.53–3.70(1H, m), 4.22(2H, q, J=7.0Hz), 4.67(1H, q, J=6.6Hz), 5.21(1H, d, J=12.4Hz), 5.38(1H, d, J=12.4Hz), 6.99–7.45(8H, m). | Ex. 3 |
| 105 | OEt | OBn | H | 3,4-dichlorophenyl | Me(S*) | R | [α]_D^29 = −34.2 (C = 1.12%, CHCl₃) | oil | ESI(Pos) 532 (M + Na)⁺ | 1.22–1.33(6H, m), 2.08–2.50(4H, m), 3.48–3.62(1H, m), 4.22(2H, q, J=7.3Hz), 4.36(1H, q, J=6.4Hz), 5.15(1H, d, J=12.4Hz), 5.31(1H, d, J=12.4Hz), 7.04–7.46(8H, m). | Ex. 3 |

TABLE 1-continued

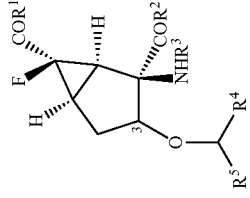

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 106 | OEt | OBn | H | 4-methylphenyl | Me | R | — | oil | ESI(Pos) 464 (M + Na)⁺ | 1.20–1.38(3H, m), 1.91–2.45(7H, m), 3.44–3.70(1H, m), 4.06–4.26(2H, m), 4.30–4.71(1H, m), 5.11–5.41(2H, m), 7.12–7.49(10H, m). | Ex. 2 |
| 107 | OEt | OBn | H | 3,4-dichlorophenyl | Et(R*) | R | $[\alpha]_D^{28} = +39.0$ (C = 1.09%, CHCl₃) | oil | ESI(Pos) 524(M + H)⁺ | 0.77(3H, t, J=7.4Hz), 1.27(3H, t, J=7.0Hz), 1.36–1.78(2H, m), 1.92–2.34(4H, m), 3.40–3.66(1H, m), 4.21(2H, q, J=7.0Hz), 4.37(1H, t, J=6.6Hz), 5.21(1H, d,J=12.4Hz), 5.39(1H, d, J=12.4Hz), 6.94–7.03(1H, m), 7.24–7.50(7H, m). | Ex. 3 |
| 108 | OEt | OBn | H | 3,4-dichlorophenyl | Et(S*) | R | $[\alpha]_D^{27} = -47.7$ (C = 1.05%, CHCl₃) | oil | ESI(Pos) 546 (M + Na)⁺ | 0.77(3H, t, J=7.5Hz), 1.27(3H, t, J=7.0Hz), 1.42–1.70(2H, m), 2.08–2.48(4H, m), 3.41–3.57(1H, m), 3.98–4.09(1H, m), 4.21(2H, q, J=7.0Hz), 5.17–5.32(2H, m), 7.03–7.13(1H, m), 7.29–7.49(7H, m). | Ex. 3 |

TABLE 1-continued

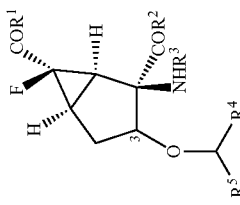

| Compound No. | R¹ | R² | R³ | R⁴ | R⁵ | 3-abs. conf. | Specific rotation (1 N aq. NaOH) | m.p.(° C.) decomposition | MS | ¹H NMR(D$_2$O)δ(ppm) | Syn. proc. |
|---|---|---|---|---|---|---|---|---|---|---|---|
| 109 | OEt | OBn | H | 3,4-dichlorophenyl | n-Pr(R*) | R | $[\alpha]_D^{26} = -40.7$ (C = 1.16%, CHCl$_3$) | oil | ESI(Pos) 560 (M + Na)⁺ | 0.84(3H, t, J=7.3Hz), 1.08–1.50(7H, m), 2.08–2.50(4H, m), 3.35–3.58(1H, m), 4.03–4.34(3H, m), 5.23(2H, s), 7.07–7.12(1H, m), 7.27–7.48(7H, m). | Ex. 3 |
| 110 | OEt | OBn | H | 3,4-dichlorophenyl | n-Pr(S*) | R | $[\alpha]_D^{27} = +39.0$ (C = 0.96%, CHCl$_3$) | oil | ESI(Pos) 560 (M + Na)⁺ | 0.84(3H, t, J=7.0Hz), 1.06–1.46(7H, m), 1.88–2.36(4H, m), 3.48–3.72(1H, m), 4.06–4.28(2H, m), 4.36–4.47(1H, m), 5.20(1H, d, J=12.3Hz), 5.40(1H, d, J=12.3Hz), 7.23–7.28(1H, m), 7.31–7.50(7H, m). | Ex. 3 |
| 111 | OEt | OBn | H | phenyl | phenyl | R | | oil | ESI(Pos) 526 (M + Na)⁺ | 1.27(3H, t, J=7.2Hz), 2.01–2.44(4H, m), 3.70–3.82(1H, m), 4.20(2H, q, J=7.2Hz), 5.12(1H, d, J=12.4Hz), 5.30(1H, d, J=12.4Hz), 5.47(1H, s), 7.17–7.41(15H, m). | Ex. 2 |

TABLE 1-continued
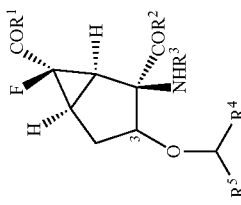
| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 112 | OEt | OBn | H | 4-F-C₆H₄ | 4-F-C₆H₄ | R | | oil | ESI(Pos) 562 (M + Na)⁺ | 1.23–1.33(3H, m), 2.08–2.40(4H, m), 3.65–3.80(1H, m), 4.16–4.28(2H, m), 5.13(1H, d, J=12.3Hz), 5.29(1H, d, J=12.3Hz), 5.47(1H, s), 6.92–6.99(4H, m), 7.12–7.19(4H, m), 7.31(5H, s). | Ex. 2 |
| 113 | OEt | OBn | H | 4-Cl-C₆H₄ | 4-Cl-C₆H₄ | R | | oil | ESI(Pos) 594 (M + Na)⁺ | 1.23–1.33(3H, m), 2.05–2.40(4H, m), 3.68–3.76(1H, m), 4.21(2H, q, J=7.2Hz), 5.12(1H, d, J=12.4Hz), 5.28(1H, d, J=12.4Hz), 5.47(1H, s), 7.09–7.31(13H, m). | Ex. 2 |
| 114 | OEt | OEt | H | 4-Cl-C₆H₄ | 4-Cl-C₆H₄ | S | [α]_D^{26} = −19.1 (C = 0.47%, CHCl₃) | oil | ESI(Pos) 532 (M + Na)⁺ | 1.12–1.39(6H, m), 1.80–2.28(2H, m), 2.41–2.69(2H, m), 3.92–4.08(1H, m), 4.09–4.34(4H, m), 5.39(1H, s), 7.10–7.37(8H, m). | Ex. 2 |

TABLE 1-continued

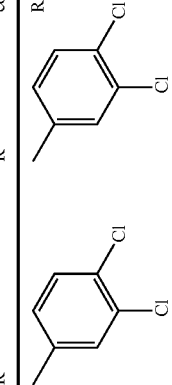

| Compound No. | R¹ | R² | R³ | R⁴ | R⁵ | 3-abs. conf. | Specific rotation (1 N aq. NaOH) | m.p.(° C.) decomposition | MS | ¹H NMR(D₂O)δ(ppm) | Syn. proc. |
|---|---|---|---|---|---|---|---|---|---|---|---|
| 115 | OEt | OBn | H | 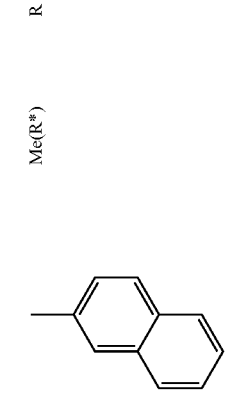 | 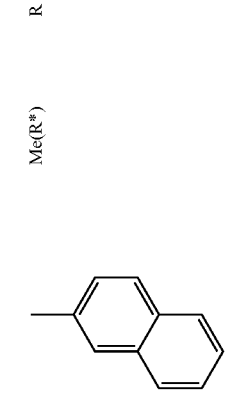 | R | $[\alpha]_D^{30} = +41.0$ (C = 0.69%, CHCl₃) | oil | ESI(Pos) 640(M + H)⁺ | 1.28(3H, t, J=7.3Hz), 2.01–2.51(4H, m), 3.62–3.80(1H, m), 4.22(2H, q, J=7.3Hz), 5.13(1H, d, J=12.1Hz), 5.29(1H, d, J=12.1Hz), 5.52(1H, s), 6.92–7.08(2H, m), 7.20–7.28(9H, m). | Ex. 2 |
| 116 | OEt | OBn | H | 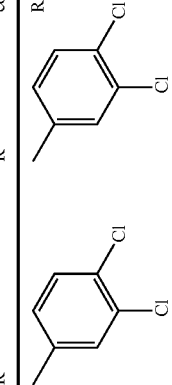 | Me(R*) | R | | oil | ESI(Pos) 514 (M + Na)⁺ | 1.24(3H, t, J=7.0Hz), 1.37(3H, d, J=6.4Hz), 1.98–2.37(4H, m), 3.64–3.75(1H, m), 4.18(2H, q, J=7.0Hz), 7.84(1H, q, J=6.4Hz), 5.23(1H, d, J=12.3Hz), 5.42(1H, d, J=12.3Hz), 7.32–7.84(12H, m). | Ex. 3 |
| 117 | OEt | OBn | H | 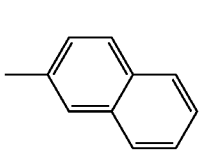 | Me(S*) | R | | oil | ESI(Pos) 514 (M + Na)⁺ | 1.24(3H, t, J=7.0Hz), 1.39(3H, d, J=6.6Hz), 2.07–2.53(4H, m), 3.51–3.62(1H, m), 4.18(2H, q, J=7.0Hz), 4.53(1H, q, J=6.6Hz), 5.18(1H, d, J=12.4Hz), 5.35(1H, d, J=12.4Hz), 7.34–7.84(12H, m). | Ex. 3 |

*¹hydrochloride

Test Example 1

Antagonistic Effect of Test Drugs on cAMP Accumulation in CHO Cells Modified to Stably Express Metabotropic Glutamate Receptor mGluR2

Using Dulbecco's modified Eagle's medium with 10% dialyzed fetal bovine serum [1% proline, 50 units/ml penicillin, 50 µg/ml streptomycin, 2 mM L-glutamine (added before use)], CHO cells modified to stably express metabotropic glutamate receptor mGluR2 were seeded in 96-well plates at a ratio of $1.26 \times 10^4$ cells/well/0.32 cm$^2$/150 µl and grown at 37° C. under 5% $CO_2$ for 2 days. The medium was then replaced by L-glutamine-free medium, and after 4 hours, the supernatant was removed by aspiration. PBS(+)-IBMX (10 mM PBS(−), 1 mM $MgCl_2$, 1 mM $CaCl_2$, 1 mM IBMX) was added in 150 µl aliquots and the plates were incubated for 20 minutes at 37° C. under 5% $CO_2$. After the supernatant was removed again by aspiration, PBS(+)-IBMX containing $10^{-5}$ M forskolin, 30 µM glutamic acid and $10^{-10}$ to $10^{-4}$ M test drug was added in 60 µL aliquots and the plates were incubated for 15 minutes at 37° C. under 5% $CO_2$ to study the antagonistic effect of test drugs on the glutamic acid-induced inhibition of forskolin-stimulated cAMP accumulation (Control experiments were conducted without adding test drugs. (Tanabe et al., Neuron, 8, 169–179 (1992)). After addition of ice-cold ethanol (100 µl) to stop the reaction, the supernatant was completely collected into separate plates, evaporated to dryness using an evaporator at normal temperature and then stored at −20° C. The dried samples were assayed for cAMP levels using a cAMP EIA kit (Amersham). The value of control samples was subtracted from each measured cAMP level. The $IC_{50}$ value, the concentration required for 50% antagonism of inhibitory effect of 30 µM glutamic acid of $10^{-5}$ M forskolin-stimulated cAMP level, was determined for each test drug.

The compounds of the present invention represented by Formula [I] wherein $R^1$ and $R^2$ are each a hydroxyl group and $R^3$ is a hydrogen atom, i.e., Compounds 1–58 in Table 1 showed a strong antagonistic effect ($IC_{50}$=500 nM or less), as measured by this test example. For example, Compounds 1, 6, 22, 28, 34, 42 and 52 had $IC_{50}$ values of 229 nM, 131 nM, 29.1 nM, 40.8 nM, 20.0 nM, 22.7 nM and 24.4 nM, respectively.

Test Example 2

Effect of Test Drugs on [$^3$H]MGS0008 Receptor Binding in CHO Cells Modified to Stably Express Metabotropic Glutamate Receptor mGluR2

Using Dulbecco's modified Eagle's medium with 10% dialyzed fetal bovine serum [1% proline, 50 units/ml penicillin, 50 µg/ml streptomycin, 2 mM L-glutamine (added before use)], CHO cells modified to stably express metabotropic glutamate receptor mGluR2 were seeded into T-225 flasks and grown at 37° C. under 5% $CO_2$. Upon confluency, the cells were washed twice with PBS(−), detached with a cell scraper, and centrifuged at 4° C. at 1000×g for 15 minutes to collect the cells. The resulting pellet was stored at −80° C. The pellet was thawed before use and suspended in 50 mM Tris-HCl buffer (pH 7.4). The suspension was homogenized with a homogenizer for 20 seconds and then centrifuged at 4° C. at 48,000×g for 20 minutes to obtain a pellet. The pellet was suspended again in the above buffer, homogenized, incubated at 37° C. for 15 minutes, and then centrifuged at 4° C. at 48,000×g for 20 minutes. The resulting pellet was further washed twice by centrifugation and then homogenized in 50 mM Tris-HCl buffer (2 mM $MgCl_2$, pH 7.4) to give a membrane fraction. The receptor-binding test was performed at a membrane concentration ranging from 50 to 200 µg/0.5 ml assay. After addition of a test drug and 3 nM [$^3$H]MGS0008, the membrane fraction was incubated at 25° C. for 1 hour. The reaction was stopped by suction filtration on a Whatman GF/C filter (pre-soaked in 0.3% polyethylenimine) using a Brandel cell harvester. After suction filtration, the filter was washed three times with ice-cold 50 mM Tris-HCl buffer (2 mM $MgCl_2$, pH 7.4, 3 ml). The filter thus obtained was treated with 10 ml of Aquasol-2 and allowed to stand for 6 hours or longer, followed by measuring the fluorescence activity using a Beckman LS6000 liquid scintillation counter. Non-specific binding was assayed in the presence of 10 µM LY354740 and subtracted from each measured binding level. The $IC_{50}$ value, the concentration required for 50% inhibition of the solvent-induced level of [$^3$H]MGS0008 binding, was determined for each test drug.

The compounds of the present invention represented by Formula [I] wherein $R^1$ and $R^2$ are each a hydroxyl group and $R^3$ is a hydrogen atom, i.e., Compounds 1–58 in Table 1 showed a strong binding activity to mGluR2 receptors ($IC_{50}$=100 nM or less), as measured by this test example.

Test Example 3

Evaluation of Antidepressant Effect by Forced Swimming Test in Rats (1) The animals used for this experiment were male SD rats (body weigh: 220–240 g, Charles River Japan).

(2) The test drugs used were:
LY341495 (Journal of Medicinal Chemistry 1998, 41, 358–378): (2S)-2-amino-2-((1S,2S)-2-carboxycycloprop-1-yl)-3-(9-xanthyl)propionic acid; and
Compound 34: (1R,2R,3R,5R,6R)-2-amino-3-(3,4-dichlorobenzyloxy)-6-fluorobicyclo[3.1.0]hexane-2,6-dicarboxylic acid.

(3) The forced swimming test was performed according to the method reported by Porsolt et al., with some modifications (European Journal of Pharmacology 1978, 47, 379–391). Namely, the rats were placed in a cylinder containing water 30 cm deep and forced to swim for 15 minutes. After a period of 24 hours, the rats were forced again to swim for 5 minutes (actual experiment). The immobility time in this actual experiment was measured for each rat to evaluate the antidepressant effect of test drugs.

The test groups received two intraperitoneal injections (24 hours and 1 hour before the actual experiment) of LY341495 or Compound 34 in $\frac{1}{15}$ M phosphate buffer at a dose of 0.3 mg/kg, 1 mg/kg or 3 mg/kg. The solvent group received only $\frac{1}{15}$ M phosphate buffer by intraperitoneal route.

Figure 2:
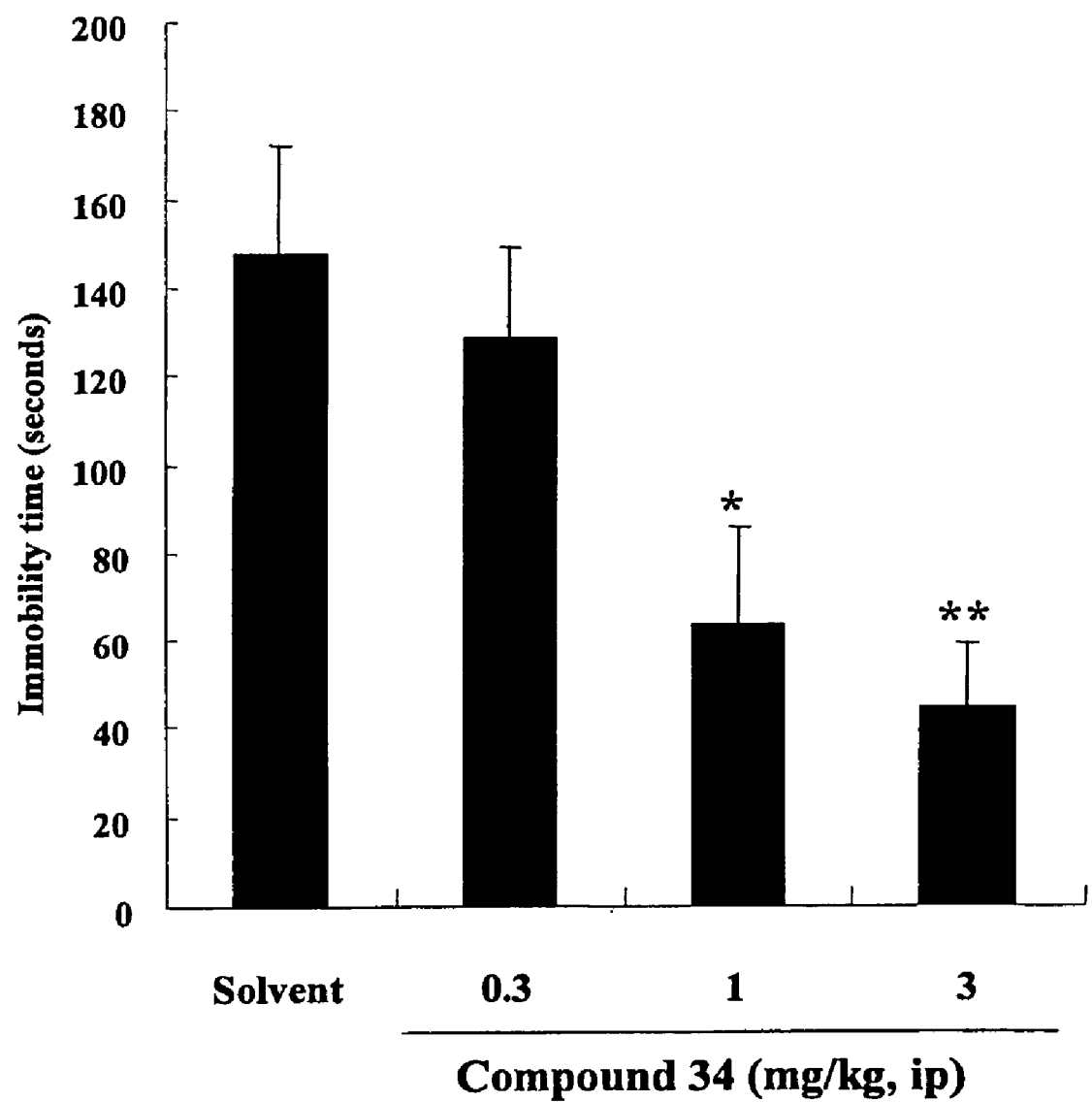

(4) The symbols * and ** in FIGS. 1 and 2 denote statistical significance at $P<0.05$ and $P<0.01$ by Dunnett's test, respectively, when compared to the solvent group receiving $\frac{1}{15}$ M phosphate buffer. Thus, FIGS. 1 and 2 indicate that when compared to the solvent group, the test groups receiving intraperitoneal injections of the test drugs, LY341495 and Compound 34, showed a significant dose-dependent reduction in immobility time and hence an excellent antidepressant effect. This indicates that a compound having an antagonistic effect on group II metabotropic glutamate receptors is useful as an antidepressant.

INDUSTRIAL APPLICABILITY

The present invention demonstrates that antagonists of metabotropic glutamate receptors are effective for depressive symptoms, thus enabling the provision of a new type of antidepressant.

In addition, one embodiment of the present invention, i.e., a 2-amino-3-alkoxy-6-fluorobicyclo[3.1.0]hexane-2,6-dicarboxylic acid derivative, or a pharmaceutically acceptable salt or hydrate thereof is a strong antagonist of metabotropic glutamate receptors. Thus, the present invention also enables the provision of a drug effective for treating and preventing psychiatric disorders such as schizophrenia, anxiety and its associated diseases, bipolar disorder and epilepsy, as well as neurological diseases such as drug dependence, cognitive disorders, Alzheimer's disease Huntington's chorea, Parkinson's disease, dyskinesia associated with muscular stiffness, cerebral ischemia, cerebral failure, myelopathy and head trauma.

What is claimed is:

1. A 2-amino-3-alkoxy-6-fluorobicyclo[3.1.0]hexane-2,6-dicarboxylic acid derivative of Formula [I]:

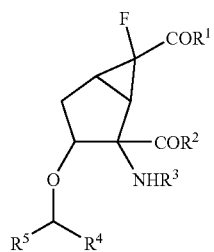

[I]

[wherein
$R^1$ and $R^2$, which may be the same or different, each represent a hydroxyl group, a $C_{1-10}$ alkoxy group, a phenoxy group, a naphthyloxy group, a $C_{1-6}$ alkoxy group which is substituted with one or two phenyl groups, a $C_{1-6}$ alkoxy-$C_{1-6}$ alkoxy group, a hydroxy-$C_{2-6}$ alkoxy group, an amino group, an amino group which is substituted with the same or different one or two $C_{1-6}$ alkyl groups, an amino group which is substituted with the same or different one or two $C_{1-6}$ alkoxy-$C_{1-6}$ alkyl groups, an amino group which is substituted with the same or different one or two hydroxy-$C_{2-6}$ alkyl groups, an amino group which is substituted with the same or different one or two $C_{1-6}$ alkoxycarbonyl-$C_{1-6}$ alkyl groups, or a native or non-native amino acid residue represented by $NR^6$—$CHR^7$-A-$CO_2R^8$ (wherein $R^6$ and $R^7$, which may be the same or different, each represent a hydrogen atom, a hydroxy-$C_{1-6}$ alkyl group, a hydroxycarbonyl-$C_{1-6}$ alkyl group, a $C_{1-10}$ alkyl group, a phenyl group, a phenyl-$C_{1-6}$ alkyl group, a hydroxyphenyl group, a hydroxyphenyl-$C_{1-6}$ alkyl group, a naphthyl group, a naphthyl-$C_{1-6}$ alkyl group, an aromatic heterocyclic $C_{1-6}$ alkyl group, a $C_{1-6}$ alkoxy-$C_{1-6}$ alkyl group, an amino-$C_{2-6}$ alkyl group, a guanidino-$C_{2-6}$ alkyl group, a mercapto-$C_{2-6}$ alkyl group, a $C_{1-6}$ alkylthio-$C_{1-6}$ alkyl group or an aminocarbonyl-$C_{1-6}$ alkyl group, or $R^6$ and $R^7$ may together represent a group capable of forming a methylene group, an ethylene group or a propylene group, or may together form a cyclic amino group; $R^8$ represents a hydrogen atom or a protecting group for a carboxyl group; and A represents a single bond, a methylene group, an ethylene group or a propylene group);

$R^3$ represents a hydrogen atom, a $C_{1-10}$ acyl group, a $C_{1-6}$ alkoxy-$C_{1-6}$ acyl group, a hydroxy-$C_{2-10}$ acyl group, a $C_{1-6}$ alkoxycarbonyl-$C_{1-6}$ acyl group, a hydroxycarbonyl-$C_{1-6}$ acyl group, or an amino acid residue represented by $R^9$—NH-A-$CHR^7$—CO (wherein $R^7$ and A are as defined above, and $R^9$ represents a hydrogen atom or a protecting group for an amino group); and $R^4$ and $R^5$, which may be the same or different, each represent a hydrogen atom, a $C_{1-10}$ alkyl group, a $C_{2-10}$ alkenyl group, a phenyl group, a naphthyl group, a 5-membered heteroaromatic ring containing one or more heteroatoms, or a phenyl group substituted with 1 to 5 substituents selected from the group consisting of a halogen atom, a $C_{1-10}$ alkyl group, a $C_{1-10}$ alkoxy group, a trifluoromethyl group, a phenyl group, a hydroxycarbonyl group, an amino group, a nitro group, a cyano group and a phenoxy group, or $R^4$ and $R^5$ may together form a cyclic structure]

or a pharmaceutically acceptable salt or hydrate thereof.

2. The 2-amino-3-alkoxy-6-fluorobicyclo[3.1.0]hexane-2,6-dicarboxylic acid derivative according to claim 1, wherein in Formula [I], $R^1$ and $R^2$ are each a hydroxyl group and $R^3$ is a hydrogen atom, or a pharmaceutically acceptable salt or hydrate thereof.

3. The 2-amino-3-alkoxy-6-fluorobicyclo[3.1.0]hexane-2,6-dicarboxylic acid derivative according to claim 1, wherein in Formula [I], $R^1$ is a hydroxyl group and $R^3$ is a hydrogen atom, or a pharmaceutically acceptable salt or hydrate thereof.

4. The 2-amino-3-alkoxy-6-fluorobicyclo[3.1.0]hexane-2,6-dicarboxylic acid derivative according to claim 1, wherein in Formula [I], $R^2$ is a hydroxyl group and $R^3$ is a hydrogen atom, or a pharmaceutically acceptable salt or hydrate thereof.

5. The 2-amino-3-alkoxy-6-fluorobicyclo[3.1.0]hexane-2,6-dicarboxylic acid derivative according to claim 1, wherein in Formula [I], $R^1$ and $R^2$ are each a hydroxyl group, or a pharmaceutically acceptable salt or hydrate thereof.

6. A 2-amino-3-alkoxy-6-fluorobicyclo[3.1.0]hexane-2,6-dicarboxylic acid derivative of Formula [II]:

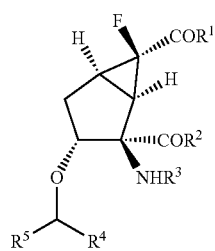

[II]

[wherein
$R^1$ and $R^2$, which may be the same or different, each represent a hydroxyl group, a $C_{1-10}$ alkoxy group, a phenoxy group, a naphthyloxy group, a $C_{1-6}$ alkoxy group which is substituted with one or two phenyl groups, a $C_{1-6}$ alkoxy-$C_{1-6}$ alkoxy group, a hydroxy-$C_{2-6}$ alkoxy group, an amino group, an amino group which is substituted with the same or different one or two $C_{1-6}$ alkyl groups, an amino group which is substituted with the same or different one or two $C_{1-6}$ alkoxy-$C_{1-6}$ alkyl groups, an amino group which is substituted with the same or different one or two hydroxy-$C_{2-6}$ alkyl groups, an amino group which is substituted with the same or different one or two $C_{1-6}$ alkoxycarbonyl-$C_{1-6}$ alkyl groups, or a native or non-native amino acid residue represented by $NR^6$—$CHR^7$-A-$CO_2R^8$ (wherein $R^6$ and $R^7$, which may be the same or different, each represent a hydrogen atom, a hydroxy-$C_{1-6}$ alkyl group, a hydroxycarbonyl-$C_{1-6}$ alkyl group, a $C_{1-10}$ alkyl group, a phenyl group, a phenyl-$C_{1-6}$ alkyl group, a hydroxyphenyl group, a hydroxyphenyl-$C_{1-6}$ alkyl group, a naphthyl group, a naphthyl-$C_{1-6}$ alkyl group, an aromatic heterocyclic $C_{1-6}$ alkyl group, a $C_{1-6}$ alkoxy-$C_{1-6}$ alkyl group, an amino-$C_{2-6}$ alkyl group, a guanidino-$C_{2-6}$ alkyl group, a mercapto-$C_{2-6}$ alkyl group, a $C_{1-6}$ alkylthio-$C_{1-6}$ alkyl group or an aminocarbonyl-$C_{1-6}$ alkyl group, or $R^6$ and $R^7$ may together represent a group capable of forming a methylene group, an ethylene group or a propylene group, or may together form a cyclic amino group; $R^8$ represents a hydrogen atom or a protecting group for a carboxyl group; and A represents a single bond, a methylene group, an ethylene group or a propylene group);

$R^3$ represents a hydrogen atom, a $C_{1-10}$ acyl group, a $C_{1-6}$ alkoxy-$C_{1-6}$ acyl group, a hydroxy-$C_{2-10}$ acyl group, a $C_{1-6}$ alkoxycarbonyl-$C_{1-6}$ acyl group, a hydroxycarbonyl-$C_{1-6}$ acyl group, or an amino acid residue represented by $R^9$—NH-A-$CHR^7$—CO (wherein $R^7$ and A are as defined above, and $R^9$ represents a hydrogen atom or a protecting group for an amino group); and $R^4$ and $R^5$, which may be the same or different, each represent a hydrogen atom, a $C_{1-10}$ alkyl group, a $C_{2-10}$ alkenyl group, a phenyl group, a naphthyl group, a 5-membered heteroaromatic ring containing one or more heteroatoms, or a phenyl group substituted with 1 to 5 substituents selected from the group consisting of a halogen atom, a $C_{1-10}$ alkyl group, a $C_{1-10}$ alkoxy group, a trifluoromethyl group, a phenyl group, a hydroxycarbonyl group, an amino group, a nitro group, a cyano group and a phenoxy group, or $R^4$ and $R^5$ may together form a cyclic structure]

or a pharmaceutically acceptable salt or hydrate thereof.

7. The 2-amino-3-alkoxy-6-fluorobicyclo[3.1.0]hexane-2,6-dicarboxylic acid derivative according to claim 6, wherein in Formula [II], $R^1$ and $R^2$ are each a hydroxyl group and $R^3$ is a hydrogen atom, or a pharmaceutically acceptable salt or hydrate thereof.

8. The 2-amino-3-alkoxy-6-fluorobicyclo[3.1.0]hexane-2,6-dicarboxylic acid derivative according to claim 6, wherein in Formula [II], $R^1$ is a hydroxyl group and $R^3$ is a hydrogen atom, or a pharmaceutically acceptable salt or hydrate thereof.

9. The 2-amino-3-alkoxy-6-fluorobicyclo[3.1.0]hexane-2,6-dicarboxylic acid derivative according to claim 6, wherein in Formula [II], $R^1$ is a hydroxyl group, $R^3$ is a hydrogen atom, and $R^2$ is a $C_{1-10}$ alkoxy group or a $C_{1-6}$ alkoxy group substituted with one phenyl group, or a pharmaceutically acceptable salt or hydrate thereof.

10. The 2-amino-3-alkoxy-6-fluorobicyclo[3.1.0]hexane-2,6-dicarboxylic acid derivative according to claim 6, wherein in Formula [II], $R^1$ is a hydroxyl group, $R^3$ is a hydrogen atom, and $R^2$ is NH—$CHR^2$—$CO_2H$, or a pharmaceutically acceptable salt or hydrate thereof.

11. The 2-amino-3-alkoxy-6-fluorobicyclo[3.1.0]hexane-2,6-dicarboxylic acid derivative according to claim 6, wherein in Formula [II], $R^2$ is a hydroxyl group and $R^3$ is a hydrogen atom, or a pharmaceutically acceptable salt or hydrate thereof.

12. The 2-amino-3-alkoxy-6-fluorobicyclo[3.1.0]hexane-2,6-dicarboxylic acid derivative according to claim 6, wherein in Formula [II], $R^2$ is a hydroxyl group, $R^3$ is a hydrogen atom, and $R^1$ is a $C_{1-10}$ alkoxy group or a $C_{1-6}$ alkoxy group substituted with one phenyl group, or a pharmaceutically acceptable salt or hydrate thereof.

13. The 2-amino-3-alkoxy-6-fluorobicyclo[3.1.0]hexane-2,6-dicarboxylic acid derivative according to claim 6, wherein in Formula [II], $R^2$ is a hydroxyl group, $R^3$ is a hydrogen atom, and $R^1$ is NH—$CHR^7$—$CO_2H$, or a pharmaceutically acceptable salt or hydrate thereof.

14. The 2-amino-3-alkoxy-6-fluorobicyclo[3.1.0]hexane-2,6-dicarboxylic acid derivative according to claim 6, wherein in Formula [II], $R^1$ and $R^2$ are each a hydroxyl group, or a pharmaceutically acceptable salt or hydrate thereof.

15. The 2-amino-3-alkoxy-6-fluorobicyclo[3.1.0]hexane-2,6-dicarboxylic acid derivative according to claim 6, wherein in Formula [II], $R^1$ and $R^2$ are each a hydroxyl group and $R^3$ is $H_2N$—$CHR^7$—CO, or a pharmaceutically acceptable salt or hydrate thereof.

16. A 2-amino-3-alkoxy-6-fluorobicyclo[3.1.0]hexane-2,6-dicarboxylic acid derivative of Formula [III]:

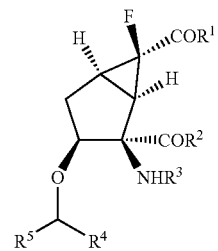

[III]

[wherein $R^1$ and $R^2$, which may be the same or different, each represent a hydroxyl group, a $C_{1-10}$ alkoxy group, a phenoxy group, a naphthyloxy group, a $C_{1-6}$ alkoxy group which is substituted with one or two phenyl groups, a $C_{1-6}$ alkoxy-$C_{1-6}$ alkoxy group, a hydroxy-$C_{2-6}$ alkoxy group, an amino group, an amino group which is substituted with the same or different one or two $C_{1-6}$ alkyl groups, an amino group which is substituted with the same or different one or two $C_{1-6}$ alkoxy-$C_{1-6}$ alkyl groups, an amino group which is substituted with the same or different one or two hydroxy-$C_{2-6}$ alkyl groups, an amino group which is substituted with the same or different one or two $C_{1-6}$ alkoxycarbonyl-$C_{1-6}$ alkyl groups, or a native or non-native amino acid residue represented by $NR^6$—$CHR^7$-A-$CO_2R^8$ (wherein $R^6$ and $R^7$, which may be the same or different, each represent a hydrogen atom, a hydroxy-$C_{1-6}$ alkyl group, a hydroxycarbonyl-$C_{1-6}$ alkyl group, a $C_{1-10}$ alkyl group, a phenyl group, a phenyl-$C_{1-6}$ alkyl group, a hydroxyphenyl group, a hydroxyphenyl-$C_{1-6}$ alkyl group, a naphthyl group, a naphthyl-$C_{1-6}$ alkyl group, an aromatic heterocyclic $C_{1-6}$ alkyl group, a $C_{1-6}$ alkoxy-$C_{1-6}$ alkyl group, an amino-$C_{2-6}$ alkyl group, a guanidino-$C_{2-6}$ alkyl group, a mercapto-$C_{2-6}$ alkyl group, a $C_{1-6}$ alkylthio-$C_{1-6}$ alkyl group or an aminocarbonyl-$C_{1-6}$ alkyl group, or $R^6$ and $R^7$ may together represent a group capable of forming a methylene group, an ethylene group or a propylene group, or may together form a cyclic amino group; $R^8$ represents a hydrogen atom or a protecting group for a carboxyl group; and A represents a single bond, a methylene group, an ethylene group or a propylene group);

$R^3$ represents a hydrogen atom, a $C_{1-10}$ acyl group, a $C_{1-6}$ alkoxy-$C_{1-6}$ acyl group, a hydroxy-$C_{2-10}$ acyl group, a $C_{1-6}$ alkoxycarbonyl-$C_{1-6}$ acyl group, a hydroxycarbonyl-$C_{1-6}$ acyl group, or an amino acid residue represented by $R^9$—NH-A-CHR$^7$—CO (wherein $R^7$ and A are as defined above, and $R^9$ represents a hydrogen atom or a protecting group for an amino group); and $R^4$ and $R^5$, which may be the same or different, each represent a hydrogen atom, a $C_{1-10}$ alkyl group, a $C_{2-10}$ alkenyl group, a phenyl group, a naphthyl group, a 5-membered heteroaromatic ring containing one or more heteroatoms, or a phenyl group substituted with 1 to 5 substituents selected from the group consisting of a halogen atom, a $C_{1-10}$ alkyl group, a $C_{1-10}$ alkoxy group, a trifluoromethyl group, a phenyl group, a hydroxycarbonyl group, an amino group, a nitro group, a cyano group and a phenoxy group, or $R^4$ and $R^5$ may together form a cyclic structure]

or a pharmaceutically acceptable salt or hydrate thereof.

17. The 2-amino-3-alkoxy-6-fluorobicyclo[3.1.0]hexane-2,6-dicarboxylic acid derivative according to claim 16, wherein in Formula [III], $R^1$ and $R^2$ are each a hydroxyl group and $R^3$ is a hydrogen atom, or a pharmaceutically acceptable salt or hydrate thereof.

18. The 2-amino-3-alkoxy-6-fluorobicyclo[3.1.0]hexane-2,6-dicarboxylic acid derivative according to claim 16, wherein in Formula [III], $R^1$ is a hydroxyl group and $R^3$ is a hydrogen atom, or a pharmaceutically acceptable salt or hydrate thereof.

19. The 2-amino-3-alkoxy-6-fluorobicyclo[3.1.0]hexane-2,6-dicarboxylic acid derivative according to claim 16, wherein in Formula [III], $R^1$ is a hydroxyl group, $R^3$ is a hydrogen atom, and $R^2$ is a $C_{1-10}$ alkoxy group or a $C_{1-6}$ alkoxy group substituted with one phenyl group, or a pharmaceutically acceptable salt or hydrate thereof.

20. The 2-amino-3-alkoxy-6-fluorobicyclo[3.1.0]hexane-2,6-dicarboxylic acid derivative according to claim 16, wherein in Formula [III], $R^1$ is a hydroxyl group, $R^3$ is a hydrogen atom, and $R^2$ NH—CHR$^7$—CO$_2$H, or a pharmaceutically acceptable salt or hydrate thereof.

21. The 2-amino-3-alkoxy-6-fluorobicyclo[3.1.0]hexane-2,6-dicarboxylic acid derivative according to claim 16, wherein in Formula [III], $R^2$ is a hydroxyl group and $R^3$ is a hydrogen atom, or a pharmaceutically acceptable salt or hydrate thereof.

22. The 2-amino-3-alkoxy-6-fluorobicyclo[3.1.0]hexane-2,6-dicarboxylic acid derivative according to claim 16, wherein in Formula [III], $R^2$ is a hydroxyl group, $R^3$ is a hydrogen atom, and $R^1$ is a $C_{1-10}$ alkoxy group or a $C_{1-6}$ alkoxy group substituted with one phenyl group, or a pharmaceutically acceptable salt or hydrate thereof.

23. The 2-amino-3-alkoxy-6-fluorobicyclo[3.1.0]hexane-2,6-dicarboxylic acid derivative according to claim 16, wherein in Formula [III], $R^2$ is a hydroxyl group, $R^3$ is a hydrogen atom, and $R^1$ is HN—CHR$^7$—CO$_2$H, or a pharmaceutically acceptable salt or hydrate thereof.

24. The 2-amino-3-alkoxy-6-fluorobicyclo[3.1.0]hexane-2,6-dicarboxylic acid derivative according to claim 16, wherein in Formula [III], $R^1$ and $R^2$ are each a hydroxyl group, or a pharmaceutically acceptable salt or hydrate thereof.

25. The 2-amino-3-alkoxy-6-fluorobicyclo[3.1.0]hexane-2,6-dicarboxylic acid derivative according to claim 16, wherein in Formula [III], $R^1$ and $R^2$ are each a hydroxyl group and $R^3$ is NH$_2$—CHR$^7$—CO, or a pharmaceutically acceptable salt or hydrate thereof.

26. A pharmaceutical preparation comprising one or more pharmaceutically acceptable carriers, excipients or diluents and the compound according to any one of claims 1 to 25.

27. A drug comprising the compound according to any one of claims 1 to 25 as an active ingredient.

28. The drug according to claim 27, which is an antagonist of group II metabotropic glutamate receptors.

* * * * *